US010501555B2

(12) United States Patent
Guerra et al.

(10) Patent No.: US 10,501,555 B2
(45) Date of Patent: Dec. 10, 2019

(54) HUMANIZED ANTI-TROP-2 MONOCLONAL ANTIBODIES AND USES THEREOF

(71) Applicant: ABRUZZO THERANOSTIC S.R.L., Lanciano (CH) (IT)

(72) Inventors: Emanuela Guerra, Cepagatti Pescara (IT); Saverio Alberti, Lanciano Chieti (IT)

(73) Assignee: ABRUZZO THERANOSTIC S.R.L., Lanciano (CH) (IT)

( * ) Notice: Subject to any disclaimer, the term of this patent is extended or adjusted under 35 U.S.C. 154(b) by 0 days.

(21) Appl. No.: 15/532,598

(22) PCT Filed: Dec. 4, 2015

(86) PCT No.: PCT/EP2015/078672
§ 371 (c)(1),
(2) Date: Jun. 2, 2017

(87) PCT Pub. No.: WO2016/087651
PCT Pub. Date: Jun. 9, 2016

(65) Prior Publication Data
US 2018/0002437 A1    Jan. 4, 2018

(30) Foreign Application Priority Data

Dec. 4, 2014 (IT) .......................... CH2014A0032 A

(51) Int. Cl.
*A61K 39/395* (2006.01)
*C07K 16/30* (2006.01)
*A61K 39/00* (2006.01)

(52) U.S. Cl.
CPC ............ *C07K 16/30* (2013.01); *A61K 39/395* (2013.01); *A61K 2039/505* (2013.01); *C07K 2317/24* (2013.01); *C07K 2317/33* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| 8,715,662 B2 * | 5/2014 | Alberti .................. C07K 16/28 424/138.1 |
| 2004/0001825 A1 | 1/2004 | Govindan et al. |
| 2007/0212350 A1 | 9/2007 | Govindan et al. |
| 2008/0131363 A1 | 6/2008 | Govindan et al. |

FOREIGN PATENT DOCUMENTS

| CN | 102827282 A | 12/2012 |
| EP | 2573120 A1 | 3/2013 |
| EP | 2594589 A1 | 5/2013 |
| EP | 2799452 A1 | 11/2014 |
| WO | 03074566 A2 | 9/2003 |
| WO | 2008144891 A1 | 12/2008 |
| WO | WO 2010089782 * | 2/2009 |
| WO | 2010089782 A1 | 8/2010 |
| WO | 2011145744 A1 | 11/2011 |
| WO | 2013068946 A2 | 5/2013 |
| WO | 2015047510 A1 | 4/2015 |

OTHER PUBLICATIONS

Maynard (Annual Review Biomedical Engineering, 2000, 2:339-376).*
Cardillo et al., "Humanized Anti-Trop-2 IgG-SN-38 Conjugate for Effective Treatment of Diverse Epithelial Cancers: Preclinical Studies in Human Cancer Xenograft Models and Monkeys", Clinical Cancer Research, 2011, vol. 17, No. 10, pp. 3157-3169.
Raji et al., "Uterine and ovarian carcinosarcomas overexpressing Trop-2 are sensitive to hRS7, a humanized anti-Trop-2 antibody", Journal of Experimental & Clinical Cancer Research, 2011, vol. 30, No. 1, pp. 1-8.
Gershoni et al., "The First Step in Developing Epitope-Based Vaccines", Biodrugs, 2007, vol. 21, No. 3, pp. 145-156.
International Search Report and Written Opinion for International Application No. PCT/EP2015/078672 (12 pages) (dated Mar. 14, 2016).

* cited by examiner

*Primary Examiner* — Laura B Goddard
(74) *Attorney, Agent, or Firm* — Lucas & Mercanti, LLP

(57) ABSTRACT

The present invention refers to humanized anti-Trop-2 antibodies and their fragments, derivatives and conjugates that are able to recognise and bind with high affinity distinct regions of the Trop-2 molecule. The present invention also teaches the use of such antibodies and of pharmaceutical compositions thereof for diagnosis and therapy of human pathologies, in particular cancer.

18 Claims, 37 Drawing Sheets

Figure 30:
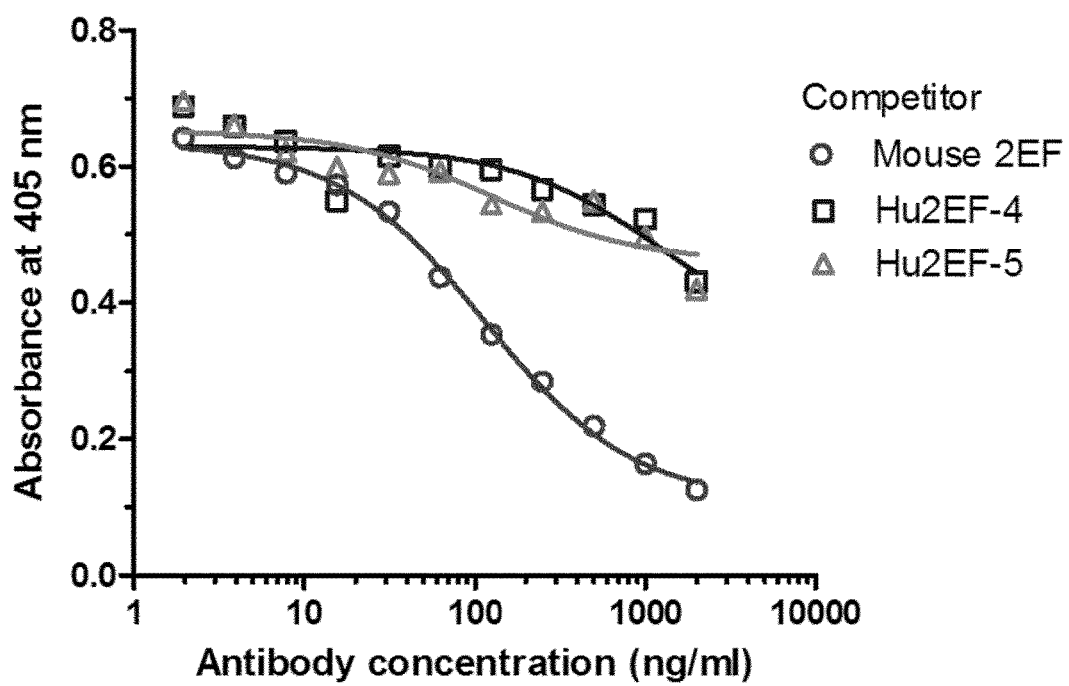

Specification includes a Sequence Listing.

SEQ ID NO:13 (nucleotide)   SEQ ID NO:14 (aminoacid)

```
ATGGAATGGAGCGGGGTCTTTATCTTTCTCCTGTCAGTGACTGCAGGCGTCCACTCCCAA
 M   E   W   S   G   V   F   I   F   L   L   S   V   T   A   G   V   H   S   Q

GTCCAGCTCCAGCAGTCTGGAGCTGAGCTCGTGAGGCCTGGGACTTCAGTGAAGATGTCC
 V   Q   L   Q   Q   S   G   A   E   L   V   R   P   G   T   S   V   K   M   S

TGCAAGGCTGCTGGATACACCTTCACTAACTACTGGATCGGATGGGTGAAGCAGAGGCCT
 C   K   A   A   G   Y   T   F   T   N   Y   W   I   G   W   V   K   Q   R   P

GGACATGGCCTCGAGTGGATTGGAGATATTTACCCTGGAGGAGGCTATACTAACTACAAT
 G   H   G   L   E   W   I   G   D   I   Y   P   G   G   G   Y   T   N   Y   N

GAGAAGTTCAAGGGCAAGGCCACACTGACTGCAGACACATCCTCCAGCACAGCCTACATG
 E   K   F   K   G   K   A   T   L   T   A   D   T   S   S   S   T   A   Y   M

CAGCTCAGCAGCCTGACATCTGAGGACTCTGCCATCTATTACTGTGCAAGAGGAACTGGA
 Q   L   S   S   L   T   S   E   D   S   A   I   Y   Y   C   A   R   G   T   G

GGCGGAGACTACTGGGGCCAAGGGACTCTGGTCACTGTCTCTGCA
 G   G   D   Y   W   G   Q   G   T   L   V   T   V   S   A
```

Fig. 1

SEQ ID NO:15 (nucleotide)   SEQ ID NO:16 (aminoacid)

```
ATGGAGACAGACACACTCCTGCTATGGGTGCTGCTGCTCTGGGTTCCAGGTTCCACTGGT
 M   E   T   D   T   L   L   L   W   V   L   L   L   W   V   P   G   S   T   G

GACATTGTGCTGACACAGTCTCCTGCTTCCTTAGCTGTATCTCTGGGGCAGAGGGCCACC
 D   I   V   L   T   Q   S   P   A   S   L   A   V   S   L   G   Q   R   A   T

ATCTCATGCAGGGCCAGCCAAAGTGTCAGTACATCTAGCTATAGTTATATGCACTGGTAC
 I   S   C   R   A   S   Q   S   V   S   T   S   S   Y   S   Y   M   H   W   Y

CAACAGAAACCAGGACAGCCACCCAAACTCCTCATCAAGTATGCATCCAACCTAGAATCT
 Q   Q   K   P   G   Q   P   P   K   L   L   I   K   Y   A   S   N   L   E   S

GGGGTCCCTGCCAGGTTCAGTGGCAGTGGGTCTGGGACAGACTTCACCCTCAACATCCAT
 G   V   P   A   R   F   S   G   S   G   S   G   T   D   F   T   L   N   I   H

CCTGTGGAGGAGGAGGATACTGCAACATATTACTGTCAGCACAGTTGGGAGATTCCGTAC
 P   V   E   E   E   D   T   A   T   Y   Y   C   Q   H   S   W   E   I   P   Y

ACGTTCGGAGGGGGGACCAAGCTGGAAATAAAA
 T   F   G   G   G   T   K   L   E   I   K
```

Fig. 2

SEQ ID NO:17 (nucleotide)   SEQ ID NO:18 (aminoacid)

```
ATGGAATGGAACTGGGTCGTTCTCTTCCTCCTGTCATTAACTGCAGGTGTCTATTCCCAG
 M   E   W   N   W   V   V   L   F   L   L   S   L   T   A   G   V   Y   S   Q

GGTCAGATGCAGCAGTCTGGAGCTGAGCTGGTGAAGCCTGGGGCTTCAGTGAAGCTGTCC
 G   Q   M   Q   Q   S   G   A   E   L   V   K   P   G   A   S   V   K   L   S

TGCAAGACTTCTGGCTTCACCTTCAGCAGTAGCTATATAAGTTGGTTGAAGCAGAAGCCT
 C   K   T   S   G   F   T   F   S   S   S   Y   I   S   W   L   K   Q   K   P

CGACAGAGTCTTGAGTGGATTGCATGGATTTATGCTGGAACTGGTGGTACTAGCTATAAT
 R   Q   S   L   E   W   I   A   W   I   Y   A   G   T   G   G   T   S   Y   N

CAGAAGTTCACAGGCAAGGCCCAACTGACTGTAGACACATCCTCCAGCACAGCCTACATG
 Q   K   F   T   G   K   A   Q   L   T   V   D   T   S   S   S   T   A   Y   M

CAACTCAGCAGCCTGACATCTGAGGACTCTGCCATCTATTACTGTGCAAGACATAACCCT
 Q   L   S   S   L   T   S   E   D   S   A   I   Y   Y   C   A   R   H   N   P

CGTTACTATGCTATGGACTACTGGGGTCAAGGAACCTCAGTCACCGTCTCCTCA
 R   Y   Y   A   M   D   Y   W   G   Q   G   T   S   V   T   V   S   S
```

Fig. 3

SEQ ID NO:19 (nucleotide)   SEQ ID NO:20 (aminoacid)

```
ATGTTCTCACTAGCTCTTCTCCTCAGTCTTCTTCTCCTCTGTGTCTCTGATTCTAGGGCA
 M   F   S   L   A   L   L   L   S   L   L   L   L   C   V   S   D   S   R   A

GAAACAACTGTGACCCAGTCTCCAGCATCCCTGTCCATGGCTATAGGAGAAAAAGTCACC
 E   T   T   V   T   Q   S   P   A   S   L   S   M   A   I   G   E   K   V   T

ATCAGATGCATAACCAGCACTGATATTGATGATGATATGAACTGGTACCAGCAGAAGCCA
 I   R   C   I   T   S   T   D   I   D   D   D   M   N   W   Y   Q   Q   K   P

GGGGAACCTCCTAAGCTCCTTATTTCAGAAGGCAATACTCTTCGTCCTGGAGTCCCATCC
 G   E   P   P   K   L   L   I   S   E   G   N   T   L   R   P   G   V   P   S

CGATTCTCCAGCAGTGGCTATGGTACAGATTTTGTTTTTACAATTGAAAACATGCTCTCA
 R   F   S   S   S   G   Y   G   T   D   F   V   F   T   I   E   N   M   L   S

GAAGATGTTGCAGATTACTACTGTTTGCAAAGTGATAACTTGCCGTACACGTTCGGAGGG
 E   D   V   A   D   Y   Y   C   L   Q   S   D   N   L   P   Y   T   F   G   G

GGGACCAAGCTGGAAATAAAA
 G   T   K   L   E   I   K
```

Fig. 4

SEQ ID NO:21 (nucleotide)   SEQ ID NO:22 (aminoacid)

```
ATGGAATGGAGCGGGGTCTTTATCTTTCTCCTGTCAGTGACTGCAGGC
 M   E   W   S   G   V   F   I   F   L   L   S   V   T   A   G

GTCCACTCCCAAGTCCAGCTCGTGCAGTCTGGAGCTGAAGTGAAGAAACCTGGGGCTTCA
 V   H   S   Q   V   Q   L   V   Q   S   G   A   E   V   K   K   P   G   A   S

GTGAAGGTGTCCTGCAAGGCTTCTGGATACACCTTCACTAACTACTGGATCGGATGGGTC
 V   K   V   S   C   K   A   S   G   Y   T   F   T   N   Y   W   I   G   W   V

AGACAGGCCCCTGGACAGGGCCTCGAGTGGATTGGAGATATTTACCCTGGAGGAGGCTAT
 R   Q   A   P   G   Q   G   L   E   W   I   G   D   I   Y   P   G   G   G   Y

ACTAACTACAATGAGAAGTTCAAGGGCAGAGCCACACTGACTGCAGACACATCCGCCAGC
 T   N   Y   N   E   K   F   K   G   R   A   T   L   T   A   D   T   S   A   S

ACAGCCTACATGGAGCTCAGCAGCCTGAGATCTGAGGACACTGCCGTGTATTACTGTGCA
 T   A   Y   M   E   L   S   S   L   R   S   E   D   T   A   V   Y   Y   C   A

AGAGGAACTGGAGGCGGAGACTACTGGGGCCAAGGGACTCTGGTCACTGTCTCTTCA
 R   G   T   G   G   G   D   Y   W   G   Q   G   T   L   V   T   V   S   S
```

Fig. 5

SEQ ID NO:23 (nucleotide)   SEQ ID NO:24 (aminoacid)

```
ATGGAATGGAGCGGGGTCTTTATCTTTCTCCTGTCAGTGACTGCAGGC
 M   E   W   S   G   V   F   I   F   L   L   S   V   T   A   G

GTCCACTCCCAAGTCCAGCTCGTGCAGTCTGGAGCTGAAGTGAAGAAACCTGGGGCTTCA
 V   H   S   Q   V   Q   L   V   Q   S   G   A   E   V   K   K   P   G   A   S

GTGAAGGTGTCCTGCAAGGCTTCTGGATACACCTTCACTAACTACTGGATCGGATGGGTC
 V   K   V   S   C   K   A   S   G   Y   T   F   T   N   Y   W   I   G   W   V

AGACAGGCCCCTGGACAGGGCCTCGAGTGGATTGGAGATATTTACCCTGGAGGAGGCTAT
 R   Q   A   P   G   Q   G   L   E   W   I   G   D   I   Y   P   G   G   G   Y

ACTAACTACAATGAGAAGTTCAAGGGCAGAGCCACACTGACTGCAGACACATCCACCAGC
 T   N   Y   N   E   K   F   K   G   R   A   T   L   T   A   D   T   S   T   S

ACAGCCTACATGGAGCTCAGCAGCCTGAGATCTGAGGACACTGCCGTGTATTACTGTGCA
 T   A   Y   M   E   L   S   S   L   R   S   E   D   T   A   V   Y   Y   C   A

AGAGGAACTGGAGGCGGAGACTACTGGGGCCAAGGGACTCTGGTCACTGTCTCTTCA
 R   G   T   G   G   G   D   Y   W   G   Q   G   T   L   V   T   V   S   S
```

Fig. 6

SEQ ID NO:25 (nucleotide)   SEQ ID NO:26 (aminoacid)

ATGGAATGGAGCGGGGTCTTTATCTTTCTCCTGTCAGTGACTGCAGGC
M   E   W   S   G   V   F   I   F   L   L   S   V   T   A   G

GTCCACTCCCAAGTCCAGCTCGTGCAGTCTGGAGCTGAAGTGAAGAAACCTGGGGCTTCA
V   H   S   Q̲   V   Q   L   V   Q   S   G   A   E   V   K   K   P   G   A   S

GTGAAGGTGTCCTGCAAGGCTTCTGGATACACCTTCACTAACTACTGGATCGGATGGGTC
V   K   V   S   C   K   A   S   G   Y   T   F   T   N̲   Y̲   W̲   I̲   G̲   W   V

AAACAGGCCCCTGGACAGGGCCTCGAGTGGATTGGAGATATTTACCCTGGAGGAGGCTAT
K   Q   A   P   G   Q   G   L   E   W   I   G   D̲   I̲   Y̲   P̲   G̲   G̲   G̲   Y̲

ACTAACTACAATGAGAAGTTCAAGGGCAGAGCCACACTGACTGCAGACACATCCGCCAGC
T̲   N̲   Y̲   N̲   E̲   K̲   F̲   K̲   G̲   R   A   T   L   T   A   D   T   S   A   S

ACAGCCTACATGGAGCTCAGCAGCCTGAGATCTGAGGACACTGCCGTGTATTACTGTGCA
T   A   Y   M   E   L   S   S   L   R   S   E   D   T   A   V   Y   Y   C   A

AGAGGAACTGGAGGCGGAGACTACTGGGGCCAAGGGACTCTGGTCACTGTCTCTTCA
R   G̲   T̲   G̲   G̲   G̲   D̲   Y̲   W   G   Q   G   T   L   V   T   V   S   S

Fig. 7

SEQ ID NO:27 (nucleotide)   SEQ ID NO:28 (aminoacid)

ATGGAGACAGACACACTCCTGCTGTGGGTGCTGCTGCTCTGGGTTCCA
M   E   T   D   T   L   L   L   W   V   L   L   L   W   V   P

GGCTCCACTGGCGACATTGTGATGACACAGTCTCCTGACTCCCTGGCTGTGTCTCTGGGG
G   S   T   G   D̲   I   V   M   T   Q   S   P   D   S   L   A   V   S   L   G

GAGAGGGCCACCATCAACTGCAGGGCCAGCCAAAGTGTCAGTACATCTAGCTATAGTTAT
E   R   A   T   I   N   C   R̲   A̲   S̲   Q̲   S̲   V̲   S̲   T̲   S̲   S̲   Y̲   S̲   Y̲

ATGCACTGGTACCAACAGAAACCAGGACAGCCACCCAAACTCCTCATCAAGTATGCATCC
M̲   H̲   W   Y   Q   Q   K   P   G   Q   P   P   K   L   L   I   K   Y̲   A̲   S̲

AACCTGGAATCTGGGGTCCCTGACAGATTCAGTGGCAGTGGGTCTGGGACAGACTTCACC
N̲   L̲   E̲   S̲   G   V   P   D   R   F   S   G   S   G   S   G   T   D   F   T

CTCACCATCAGCTCCCTGCAGGCCGAGGATGTGGCAGTCTATTACTGTCAGCACAGTTGG
L   T   I   S   S   L   Q   A   E   D   V   A   V   Y   Y   C   Q̲   H̲   S̲   W̲

GAGATTCCCTACACCTTCGGACAGGGGACCAAGCTGGAAATCAAA
E̲   I̲   P̲   Y̲   T̲   F   G   Q   G   T   K   L   E   I   K

Fig. 8

SEQ ID NO:29 (nucleotide)  SEQ ID NO:30 (aminoacid)

```
ATGGAGACAGACACACTCCTGCTGTGGGTGCTGCTGCTCTGGGTTCCA
 M  E  T  D  T  L  L  L  W  V  L  L  L  W  V  P

GGCTCCACTGGCGACATTGTGCTGACACAGTCTCCTGACTCCCTGGCTGTGTCTCTGGGG
 G  S  T  G  D  I  V  L  T  Q  S  P  D  S  L  A  V  S  L  G

GAGAGGGCCACCATCAACTGCAGGGCCAGCCAAAGTGTCAGTACATCTAGCTATAGTTAT
 E  R  A  T  I  N  C  R  A  S  Q  S  V  S  T  S  S  Y  S  Y

ATGCACTGGTACCAACAGAAACCAGGACAGCCACCCAAACTCCTCATCAAGTATGCATCC
 M  H  W  Y  Q  Q  K  P  G  Q  P  P  K  L  L  I  K  Y  A  S

AACCTGGAATCTGGGGTCCCTGACAGATTCAGTGGCAGTGGGTCTGGGACAGACTTCACC
 N  L  E  S  G  V  P  D  R  F  S  G  S  G  S  G  T  D  F  T

CTCACCATCAGCTCCCTGCAGGCCGAGGATGTGGCAGTCTATTACTGTCAGCACAGTTGG
 L  T  I  S  S  L  Q  A  E  D  V  A  V  Y  Y  C  Q  H  S  W

GAGATTCCCTACACCTTCGGAGGCGGGACCAAGCTGGAAATCAAA
 E  I  P  Y  T  F  G  G  G  T  K  L  E  I  K
```

Fig. 9

SEQ ID NO:31 (nucleotide)  SEQ ID NO:32 (aminoacid)

```
ATGGAATGGAACTGGGTCGTTCTCTTCCTCCTGTCACTGACTGCAGGC
 M  E  W  N  W  V  V  L  F  L  L  S  L  T  A  G

GTCTATTCCCAAGTGCAGCTCGTCCAGTCTGGAGCTGAAGTCAAAAAGCCTGGGGCTTCA
 V  Y  S  Q  V  Q  L  V  Q  S  G  A  E  V  K  K  P  G  A  S

GTGAAAGTCTCCTGCAAGGCTTCTGGCTTCACCTTCAGCAGTAGCTATATCAGTTGGTTG
 V  K  V  S  C  K  A  S  G  F  T  F  S  S  S  Y  I  S  W  L

AGGCAGGCCCCTGGACAGAGACTTGAGTGGATTGCATGGATTTATGCTGGAACTGGCGGA
 R  Q  A  P  G  Q  R  L  E  W  I  A  W  I  Y  A  G  T  G  G

ACTAGCTATAATCAGAAGTTCACAGGCAAGGCCACACTGACTGTAGACACATCCGCCAGC
 T  S  Y  N  Q  K  F  T  G  K  A  T  L  T  V  D  T  S  A  S

ACAGCCTACATGGAACTCAGCAGCCTGAGATCTGAGGACACTGCCGTCTATTACTGTGCA
 T  A  Y  M  E  L  S  S  L  R  S  E  D  T  A  V  Y  Y  C  A

AGACATAACCCTCGTTACTATGCTATGGACTACTGGGGCCAAGGAACCACAGTCACCGTC
 R  H  N  P  R  Y  Y  A  M  D  Y  W  G  Q  G  T  T  V  T  V

TCCTCA
 S  S
```

Fig. 10

SEQ ID NO:33 (nucleotide)  SEQ ID NO:34 (aminoacid)

ATGGAATGGAACTGGGTCGTTCTCTTCCTCCTGTCACTGACTGCAGGC
 M   E   W   N   W   V   V   L   F   L   L   S   L   T   A   G

GTCTATTCCCAAGTGCAGCTCGTCCAGTCTGGAGCTGAAGTCAAAAAGCCTGGGGCTTCA
 V   Y   S   Q̲   V   Q   L   V   Q   S   G   A   E   V   K   K   P   G   A   S

GTGAAAGTCTCCTGCAAGGCTTCTGGCTTCACCTTCAGCAGTAGCTATATCAGTTGGTTG
 V   K   V   S   C   K   A   S   G   F   T   F   S   S̲   S̲   Y̲   I̲   S̲   W̲   L̲

AGGCAGGCCCCTGGACAGAGACTTGAGTGGATTGCATGGATTTATGCTGGAACTGGCGGA
 R   Q   A   P   G   Q   R   L   E   W   I   A   W̲   I̲   Y̲   A̲   G̲   T̲   G̲   G̲

ACTAGCTATAATCAGAAGTTCACAGGCAGAGTCACACTGACTGTAGACACATCCGCCAGC
 T̲   S̲   Y̲   N̲   Q̲   K̲   F̲   T̲   G̲   R   V   T   L   T   V   D   T   S   A   S

ACAGCCTACATGGAACTCAGCAGCCTGAGATCTGAGGACACTGCCGTCTATTACTGTGCA
 T   A   Y   M   E   L   S   S   L   R   S   E   D   T   A   V   Y   Y   C   A

AGACATAACCCTCGTTACTATGCTATGGACTACTGGGGCCAAGGAACCACAGTCACCGTC
 R̲   H̲   N̲   P̲   R̲   Y̲   Y̲   A̲   M̲   D̲   Y̲   W   G   Q   G   T   T   V   T   V

TCCTCA
 S   S

Fig. 11

SEQ ID NO:35 (nucleotide)  SEQ ID NO:36 (aminoacid)

ATGTTCTCACTGGCTCTGCTCCTCAGTCTGCTGCTCCTCTGTGTCTCT
 M   F   S   L   A   L   L   L   S   L   L   L   L   C   V   S

GATTCTAGAGCAGACATCCAGATGACCCAGTCTCCAAGCTCCCTGTCCGCCAGCGTGGGA
 D   S   R   A   D̲   I   Q   M   T   Q   S   P   S   S   L   S   A   S   V   G

GATAGAGTCACCATCACATGCATCACCAGCACTGATATTGATGATGATATGAACTGGTAC
 D   R   V   T   I   T   C   I̲   T̲   S̲   T̲   D̲   I̲   D̲   D̲   D̲   M̲   N̲   W   Y

CAGCAGAAGCCAGGGAAAGCTCCTAAGCTCCTGATTTCAGAAGGCAATACTCTGCGCCCT
 Q   Q   K   P   G   K   A   P   K   L   L   I   S   E̲   G̲   N̲   T̲   L̲   R̲   P̲

GGAGTCCCATCCCGATTCTCCGGCAGTGGCTATGGAACAGATTTTACCTTTACAATTAGC
 G   V   P   S   R   F   S   G   S   G   Y   G   T   D   F   T   F   T   I   S

TCCCTGCAGCCAGAAGATATTGCAACCTACTACTGTTTGCAAAGTGATAACCTGCCCTAC
 S   L   Q   P   E   D   I   A   T   Y   Y   C   L̲   Q̲   S̲   D̲   N̲   L̲   P̲   Y̲

ACCTTCGGAGGGGGGACCAAAGTCGAAATCAAA
 T̲   F   G   G   G   T   K   V   E   I   K

Fig. 12

SEQ ID NO:37 (nucleotide)   SEQ ID NO:38 (aminoacid)

```
ATGTTCTCACTGGCTCTGCTCCTCAGTCTGCTGCTCCTCTGTGTCTCT
 M  F  S  L  A  L  L  S  L  L  L  L  C  V  S

GATTCTAGAGCAGACATCCAGATGACCCAGTCTCCAAGCTCCCTGTCCGCCAGCGTGGGA
 D  S  R  A  D̲  I  Q  M  T  Q  S  P  S  S  L  S  A  S  V  G

GATAGAGTCACCATCACATGCATCACCAGCACTGATATTGATGATGATATGAACTGGTAC
 D  R  V  T  I  T  C  I̲  T̲  S̲  T̲  D̲  I̲  D̲  D̲  D̲  M̲  N̲  W  Y

CAGCAGAAGCCAGGGAAAGCTCCTAAGCTCCTGATTTCAGAAGGCAATACTCTGCGCCCT
 Q  Q  K  P  G  K  A  P  K  L  L  I  S  E̲  G̲  N̲  T̲  L̲  R̲  P̲

GGAGTCCCATCCCGATTCTCCGGCAGTGGCTCTGGAACAGATTTTACCTTTACAATTAGC
 G  V  P  S  R  F  S  G  S  G  S  G  T  D  F  T  F  T  I  S

TCCCTGCAGCCAGAAGATATTGCAACCTACTACTGTTTGCAAAGTGATAACCTGCCCTAC
 S  L  Q  P  E  D  I  A  T  Y  Y  C  L̲  Q̲  S̲  D̲  N̲  L̲  P̲  Y̲

ACCTTCGGAGGGGGGACCAAAGTCGAAATCAAA
 T̲  F  G  G  G  T  K  V  E  I  K
```

Fig. 13

SEQ ID NO:39 (nucleotide)   SEQ ID NO:40 (aminoacid)

```
ATGTTCTCACTGGCTCTGCTCCTCAGTCTGCTGCTCCTCTGTGTCTCT
 M  F  S  L  A  L  L  S  L  L  L  L  C  V  S

GATTCTAGAGCAGACACCCAGATGACCCAGTCTCCAAGCTCCCTGTCCGCCAGCGTGGGA
 D  S  R  A  D̲  T  Q  M  T  Q  S  P  S  S  L  S  A  S  V  G

GATAGAGTCACCATCACATGCATCACCAGCACTGATATTGATGATGATATGAACTGGTAC
 D  R  V  T  I  T  C  I̲  T̲  S̲  T̲  D̲  I̲  D̲  D̲  D̲  M̲  N̲  W  Y

CAGCAGAAGCCAGGGAAAGCTCCTAAGCTCCTGATTTCAGAAGGCAATACTCTGCGCCCT
 Q  Q  K  P  G  K  A  P  K  L  L  I  S  E̲  G̲  N̲  T̲  L̲  R̲  P̲

GGAGTCCCATCCCGATTCTCCGGCAGTGGCTATGGAACAGATTTTACCTTTACAATTAGC
 G  V  P  S  R  F  S  G  S  G  Y  G  T  D  F  T  F  T  I  S

TCCCTGCAGCCAGAAGATATTGCAACCTACTACTGTTTGCAAAGTGATAACCTGCCCTAC
 S  L  Q  P  E  D  I  A  T  Y  Y  C  L̲  Q̲  S̲  D̲  N̲  L̲  P̲  Y̲

ACCTTCGGAGGGGGGACCAAAGTCGAAATCAAA
 T̲  F  G  G  G  T  K  V  E  I  K
```

Fig. 14

SEQ ID NO:41 (nucleotide)   SEQ ID NO:42 (aminoacid)

```
ATGGAATGGAGCGGGGTCTTTATCTTTCTCCTGTCAGTGACTGCAGGCGTCCACTCCCAA
 M   E   W   S   G   V   F   I   F   L   L   S   V   T   A   G   V   H   S   Q
GTCCAGCTCGTGCAGTCTGGAGCTGAAGTGAAGAAACCTGGGGCTTCAGTGAAGGTGTCC
 V   Q   L   V   Q   S   G   A   E   V   K   K   P   G   A   S   V   K   V   S
TGCAAGGCTTCTGGATACACCTTCACTAACTACTGGATCGGATGGGTCAAACAGGCCCCT
 C   K   A   S   G   Y   T   F   T   N   Y   W   I   G   W   V   K   Q   A   P
GGACAGGGCCTCGAGTGGATTGGAGATATTTACCCTGGAGGAGGCTATACTAACTACAAT
 G   Q   G   L   E   W   I   G   D   I   Y   P   G   G   G   Y   T   N   Y   N
GAGAAGTTCAAGGGCAGAGCCACACTGACTGCAGACACATCCGCCAGCACAGCCTACATG
 E   K   F   K   G   R   A   T   L   T   A   D   T   S   A   S   T   A   Y   M
GAGCTCAGCAGCCTGAGATCTGAGGACACTGCCGTGTATTACTGTGCAAGAGGAACTGGA
 E   L   S   S   L   R   S   E   D   T   A   V   Y   Y   C   A   R   G   T   G
GGCGGAGACTACTGGGGCCAAGGGACTCTGGTCACTGTCTCTTCAGCCTCCACCAAGGGC
 G   G   D   Y   W   G   Q   G   T   L   V   T   V   S   S   A   S   T   K   G
CCATCGGTCTTCCCCCTGGCACCCTCCTCCAAGAGCACCTCTGGGGGCACAGCGGCCCTG
 P   S   V   F   P   L   A   P   S   S   K   S   T   S   G   G   T   A   A   L
GGCTGCCTGGTCAAGGACTACTTCCCCGAACCGGTGACGGTGTCGTGGAACTCAGGCGCC
 G   C   L   V   K   D   Y   F   P   E   P   V   T   V   S   W   N   S   G   A
CTGACCAGCGGCGTGCACACCTTCCCGGCTGTCCTACAGTCCTCAGGACTCTACTCCCTC
 L   T   S   G   V   H   T   F   P   A   V   L   Q   S   S   G   L   Y   S   L
AGCAGCGTGGTGACCGTGCCCTCCAGCAGCTTGGGCACCCAGACCTACATCTGCAACGTG
 S   S   V   V   T   V   P   S   S   S   L   G   T   Q   T   Y   I   C   N   V
AATCACAAGCCCAGCAACACCAAGGTGGACAAGAAAGTTGAGCCCAAATCTTGTGACAAA
 N   H   K   P   S   N   T   K   V   D   K   K   V   E   P   K   S   C   D   K
ACTCACACATGCCCACCGTGCCCAGCACCTGAACTCCTGGGGGGACCGTCAGTCTTCCTC
 T   H   T   C   P   P   C   P   A   P   E   L   L   G   G   P   S   V   F   L
TTCCCCCCAAAACCCAAGGACACCCTCATGATCTCCCGGACCCCTGAGGTCACATGCGTG
 F   P   P   K   P   K   D   T   L   M   I   S   R   T   P   E   V   T   C   V
GTGGTGGACGTGAGCCACGAAGACCCTGAGGTCAAGTTCAACTGGTACGTGGACGGCGTG
 V   V   D   V   S   H   E   D   P   E   V   K   F   N   W   Y   V   D   G   V
GAGGTGCATAATGCCAAGACAAAGCCGCGGGAGGAGCAGTACAACAGCACGTACCGTGTG
 E   V   H   N   A   K   T   K   P   R   E   E   Q   Y   N   S   T   Y   R   V
GTCAGCGTCCTCACCGTCCTGCACCAGGACTGGCTGAATGGCAAGGAGTACAAGTGCAAG
 V   S   V   L   T   V   L   H   Q   D   W   L   N   G   K   E   Y   K   C   K
GTCTCCAACAAAGCCCTCCCAGCCCCCATCGAGAAAACCATCTCCAAAGCCAAAGGGCAG
 V   S   N   K   A   L   P   A   P   I   E   K   T   I   S   K   A   K   G   Q
CCCCGAGAACCACAGGTGTACACCCTGCCCCCATCCCGGGATGAGCTGACCAAGAACCAG
 P   R   E   P   Q   V   Y   T   L   P   P   S   R   D   E   L   T   K   N   Q
GTCAGCCTGACCTGCCTGGTCAAAGGCTTCTATCCCAGCGACATCGCCGTGGAGTGGGAG
 V   S   L   T   C   L   V   K   G   F   Y   P   S   D   I   A   V   E   W   E
AGCAATGGGCAGCCGGAGAACAACTACAAGACCACGCCTCCCGTGCTGGACTCCGACGGC
 S   N   G   Q   P   E   N   N   Y   K   T   T   P   P   V   L   D   S   D   G
TCCTTCTTCCTCTACAGCAAGCTCACCGTGGACAAGAGCAGGTGGCAGCAGGGGAACGTC
 S   F   F   L   Y   S   K   L   T   V   D   K   S   R   W   Q   Q   G   N   V
TTCTCATGCTCCGTGATGCATGAGGCTCTGCACAACCACTACACGCAGAAGAGCCTCTCC
 F   S   C   S   V   M   H   E   A   L   H   N   H   Y   T   Q   K   S   L   S
CTGTCTCCGGGTAAATGA
 L   S   P   G   K   *
```

Fig. 15

SEQ ID NO:43 (nucleotide)   SEQ ID NO:44 (aminoacid)

```
ATGGAGACAGACACACTCCTGCTGTGGGTGCTGCTGCTCTGGGTTCCAGGCTCCACTGGC
 M   E   T   D   T   L   L   L   W   V   L   L   L   W   V   P   G   S   T   G
GACATTGTGCTGACACAGTCTCCTGACTCCCTGGCTGTGTCTCTGGGGGAGAGGGCCACC
 D   I   V   L   T   Q   S   P   D   S   L   A   V   S   L   G   E   R   A   T
ATCAACTGCAGGGCCAGCCAAAGTGTCAGTACATCTAGCTATAGTTATATGCACTGGTAC
 I   N   C   R   A   S   Q   S   V   S   T   S   S   Y   S   Y   M   H   W   Y
CAACAGAAACCAGGACAGCCACCCAAACTCCTCATCAAGTATGCATCCAACCTGGAATCT
 Q   Q   K   P   G   Q   P   P   K   L   L   I   K   Y   A   S   N   L   E   S
GGGGTCCCTGACAGATTCAGTGGCAGTGGGTCTGGGACAGACTTCACCCTCACCATCAGC
 G   V   P   D   R   F   S   G   S   G   S   G   T   D   F   T   L   T   I   S
TCCCTGCAGGCCGAGGATGTGGCAGTCTATTACTGTCAGCACAGTTGGGAGATTCCCTAC
 S   L   Q   A   E   D   V   A   V   Y   Y   C   Q   H   S   W   E   I   P   Y
ACCTTCGGAGGCGGGACCAAGCTGGAAATCAAACGAACTGTGGCTGCACCATCTGTCTTC
 T   F   G   G   G   T   K   L   E   I   K   R   T   V   A   A   P   S   V   F
ATCTTCCCGCCATCTGATGAGCAGTTGAAATCTGGAACTGCCTCTGTTGTGTGCCTGCTG
 I   F   P   P   S   D   E   Q   L   K   S   G   T   A   S   V   V   C   L   L
AATAACTTCTATCCCAGAGAGGCCAAAGTACAGTGGAAGGTGGATAACGCCCTCCAATCG
 N   N   F   Y   P   R   E   A   K   V   Q   W   K   V   D   N   A   L   Q   S
GGTAACTCCCAGGAGAGTGTCACAGAGCAGGACAGCAAGGACAGCACCTACAGCCTCAGC
 G   N   S   Q   E   S   V   T   E   Q   D   S   K   D   S   T   Y   S   L   S
AGCACCCTGACGCTGAGCAAAGCAGACTACGAGAAACACAAAGTCTACGCCTGCGAAGTC
 S   T   L   T   L   S   K   A   D   Y   E   K   H   K   V   Y   A   C   E   V
ACCCATCAGGGCCTGAGCTCGCCCGTCACAAAGAGCTTCAACAGGGGAGAGTGTTAG
 T   H   Q   G   L   S   S   P   V   T   K   S   F   N   R   G   E   C   *
```

Fig. 16

SEQ ID NO:45 (nucleotide)  SEQ ID NO:46 (aminoacid)

```
ATGGAATGGAACTGGGTCGTTCTCTTCCTCCTGTCACTGACTGCAGGCGTCTATTCCCAA
 M   E   W   N   W   V   V   L   F   L   L   S   L   T   A   G   V   Y   S   Q
GTGCAGCTCGTCCAGTCTGGAGCTGAAGTCAAAAAGCCTGGGGCTTCAGTGAAAGTCTCC
 V   Q   L   V   Q   S   G   A   E   V   K   K   P   G   A   S   V   K   V   S
TGCAAGGCTTCTGGCTTCACCTTCAGCAGTAGCTATATCAGTTGGTTGAGGCAGGCCCCT
 C   K   A   S   G   F   T   F   S   S   S   Y   I   S   W   L   R   Q   A   P
GGACAGAGACTTGAGTGGATTGCATGGATTTATGCTGGAACTGGCGGAACTAGCTATAAT
 G   Q   R   L   E   W   I   A   W   I   Y   A   G   T   G   G   T   S   Y   N
CAGAAGTTCACAGGCAAGGCCACACTGACTGTAGACACATCCGCCAGCACAGCCTACATG
 Q   K   F   T   G   K   A   T   L   T   V   D   T   S   A   S   T   A   Y   M
GAACTCAGCAGCCTGAGATCTGAGGACACTGCCGTCTATTACTGTGCAAGACATAACCCT
 E   L   S   S   L   R   S   E   D   T   A   V   Y   Y   C   A   R   H   N   P
CGTTACTATGCTATGGACTACTGGGGCCAAGGAACCACAGTCACCGTCTCCTCAGCCTCC
 R   Y   Y   A   M   D   Y   W   G   Q   G   T   T   V   T   V   S   S   A   S
ACCAAGGGCCCATCGGTCTTCCCCCTGGCACCCTCCTCCAAGAGCACCTCTGGGGGCACA
 T   K   G   P   S   V   F   P   L   A   P   S   S   K   S   T   S   G   G   T
GCGGCCCTGGGCTGCCTGGTCAAGGACTACTTCCCCGAACCGGTGACGGTGTCGTGGAAC
 A   A   L   G   C   L   V   K   D   Y   F   P   E   P   V   T   V   S   W   N
TCAGGCGCCCTGACCAGCGGCGTGCACACCTTCCCGGCTGTCCTACAGTCCTCAGGACTC
 S   G   A   L   T   S   G   V   H   T   F   P   A   V   L   Q   S   S   G   L
TACTCCCTCAGCAGCGTGGTGACCGTGCCCTCCAGCAGCTTGGGCACCCAGACCTACATC
 Y   S   L   S   S   V   V   T   V   P   S   S   S   L   G   T   Q   T   Y   I
TGCAACGTGAATCACAAGCCCAGCAACACCAAGGTGGACAAGAAAGTTGAGCCCAAATCT
 C   N   V   N   H   K   P   S   N   T   K   V   D   K   K   V   E   P   K   S
TGTGACAAAACTCACACATGCCCACCGTGCCCAGCACCTGAACTCCTGGGGGGACCGTCA
 C   D   K   T   H   T   C   P   P   C   P   A   P   E   L   L   G   G   P   S
GTCTTCCTCTTCCCCCCAAAACCCAAGGACACCCTCATGATCTCCCGGACCCCTGAGGTC
 V   F   L   F   P   P   K   P   K   D   T   L   M   I   S   R   T   P   E   V
ACATGCGTGGTGGTGGACGTGAGCCACGAAGACCCTGAGGTCAAGTTCAACTGGTACGTG
 T   C   V   V   V   D   V   S   H   E   D   P   E   V   K   F   N   W   Y   V
GACGGCGTGGAGGTGCATAATGCCAAGACAAAGCCGCGGGAGGAGCAGTACAACAGCACG
 D   G   V   E   V   H   N   A   K   T   K   P   R   E   E   Q   Y   N   S   T
TACCGTGTGGTCAGCGTCCTCACCGTCCTGCACCAGGACTGGCTGAATGGCAAGGAGTAC
 Y   R   V   V   S   V   L   T   V   L   H   Q   D   W   L   N   G   K   E   Y
AAGTGCAAGGTCTCCAACAAAGCCCTCCCAGCCCCCATCGAGAAAACCATCTCCAAAGCC
 K   C   K   V   S   N   K   A   L   P   A   P   I   E   K   T   I   S   K   A
AAAGGGCAGCCCCGAGAACCACAGGTGTACACCCTGCCCCCATCCCGGGATGAGCTGACC
 K   G   Q   P   R   E   P   Q   V   Y   T   L   P   P   S   R   D   E   L   T
AAGAACCAGGTCAGCCTGACCTGCCTGGTCAAAGGCTTCTATCCCAGCGACATCGCCGTG
 K   N   Q   V   S   L   T   C   L   V   K   G   F   Y   P   S   D   I   A   V
GAGTGGGAGAGCAATGGGCAGCCGGAGAACAACTACAAGACCACGCCTCCCGTGCTGGAC
 E   W   E   S   N   G   Q   P   E   N   N   Y   K   T   T   P   P   V   L   D
TCCGACGGCTCCTTCTTCCTCTACAGCAAGCTCACCGTGGACAAGAGCAGGTGGCAGCAG
 S   D   G   S   F   F   L   Y   S   K   L   T   V   D   K   S   R   W   Q   Q
GGGAACGTCTTCTCATGCTCCGTGATGCATGAGGCTCTGCACAACCACTACACGCAGAAG
 G   N   V   F   S   C   S   V   M   H   E   A   L   H   N   H   Y   T   Q   K
AGCCTCTCCCTGTCTCCGGGTAAATGA
 S   L   S   L   S   P   G   K   *
```

Fig. 17

SEQ ID NO:47 (nucleotide)  SEQ ID NO:48 (aminoacid)

```
ATGTTCTCACTGGCTCTGCTCCTCAGTCTGCTGCTCCTCTGTGTCTCTGATTCTAGAGCA
 M  F  S  L  A  L  L  L  S  L  L  L  L  C  V  S  D  S  R  A
GACACCCAGATGACCCAGTCTCCAAGCTCCCTGTCCGCCAGCGTGGGAGATAGAGTCACC
 D  T  Q  M  T  Q  S  P  S  S  L  S  A  S  V  G  D  R  V  T
ATCACATGCATCACCAGCACTGATATTGATGATGATATGAACTGGTACCAGCAGAAGCCA
 I  T  C  I  T  S  T  D  I  D  D  D  M  N  W  Y  Q  Q  K  P
GGGAAAGCTCCTAAGCTCCTGATTTCAGAAGGCAATACTCTGCGCCCTGGAGTCCCATCC
 G  K  A  P  K  L  L  I  S  E  G  N  T  L  R  P  G  V  P  S
CGATTCTCCGGCAGTGGCTATGGAACAGATTTTACCTTTACAATTAGCTCCCTGCAGCCA
 R  F  S  G  S  G  Y  G  T  D  F  T  F  T  I  S  S  L  Q  P
GAAGATATTGCAACCTACTACTGTTTGCAAAGTGATAACCTGCCCTACACCTTCGGAGGG
 E  D  I  A  T  Y  Y  C  L  Q  S  D  N  L  P  Y  T  F  G  G
GGGACCAAAGTCGAAATCAAACGAACTGTGGCTGCACCATCTGTCTTCATCTTCCCGCCA
 G  T  K  V  E  I  K  R  T  V  A  A  P  S  V  F  I  F  P  P
TCTGATGAGCAGTTGAAATCTGGAACTGCCTCTGTTGTGTGCCTGCTGAATAACTTCTAT
 S  D  E  Q  L  K  S  G  T  A  S  V  V  C  L  L  N  N  F  Y
CCCAGAGAGGCCAAAGTACAGTGGAAGGTGGATAACGCCCTCCAATCGGGTAACTCCCAG
 P  R  E  A  K  V  Q  W  K  V  D  N  A  L  Q  S  G  N  S  Q
GAGAGTGTCACAGAGCAGGACAGCAAGGACAGCACCTACAGCCTCAGCAGCACCCTGACG
 E  S  V  T  E  Q  D  S  K  D  S  T  Y  S  L  S  S  T  L  T
CTGAGCAAAGCAGACTACGAGAAACACAAAGTCTACGCCTGCGAAGTCACCCATCAGGGC
 L  S  K  A  D  Y  E  K  H  K  V  Y  A  C  E  V  T  H  Q  G
CTGAGCTCGCCCGTCACAAAGAGCTTCAACAGGGGAGAGTGTTAG
 L  S  S  P  V  T  K  S  F  N  R  G  E  C  •
```

Fig. 18

SEQ ID NO:49 (nucleotide)  SEQ ID NO:50 (aminoacid)

```
ATGGAATGGAACTGGGTCGTTCTCTTCCTCCTGTCACTGACTGCAGGCGTCTATTCCCAA
 M   E   W   N   W   V   V   L   F   L   L   S   L   T   A   G   V   Y   S   Q
GTGCAGCTCGTCCAGTCTGGAGCTGAAGTCAAAAAGCCTGGGGCTTCAGTGAAAGTCTCC
 V   Q   L   V   Q   S   G   A   E   V   K   K   P   G   A   S   V   K   V   S
TGCAAGGCTTCTGGCTTCACCTTCAGCAGTAGCTATATCAGTTGGTTGAGGCAGGCCCCT
 C   K   A   S   G   F   T   F   S   S   S   Y   I   S   W   L   R   Q   A   P
GGACAGAGACTTGAGTGGATTGCATGGATTTATGCTGGAACTGGCGGAACTAGCTATAAT
 G   Q   R   L   E   W   I   A   W   I   Y   A   G   T   G   G   T   S   Y   N
CAGAAGTTCACAGGCAGAGTCACACTGACTGTAGACACATCCGCCAGCACAGCCTACATG
 Q   K   F   T   G   R   V   T   L   T   V   D   T   S   A   S   T   A   Y   M
GAACTCAGCAGCCTGAGATCTGAGGACACTGCCGTCTATTACTGTGCAAGACATAACCCT
 E   L   S   S   L   R   S   E   D   T   A   V   Y   Y   C   A   R   H   N   P
CGTTACTATGCTATGGACTACTGGGGCCAAGGAACCACAGTCACCGTCTCCTCAGCCTCC
 R   Y   Y   A   M   D   Y   W   G   Q   G   T   T   V   T   V   S   S   A   S
ACCAAGGGCCCATCGGTCTTCCCCCTGGCACCCTCCTCCAAGAGCACCTCTGGGGGCACA
 T   K   G   P   S   V   F   P   L   A   P   S   S   K   S   T   S   G   G   T
GCGGCCCTGGGCTGCCTGGTCAAGGACTACTTCCCCGAACCGGTGACGGTGTCGTGGAAC
 A   A   L   G   C   L   V   K   D   Y   F   P   E   P   V   T   V   S   W   N
TCAGGCGCCCTGACCAGCGGCGTGCACACCTTCCCGGCTGTCCTACAGTCCTCAGGACTC
 S   G   A   L   T   S   G   V   H   T   F   P   A   V   L   Q   S   S   G   L
TACTCCCTCAGCAGCGTGGTGACCGTGCCCTCCAGCAGCTTGGGCACCCAGACCTACATC
 Y   S   L   S   S   V   V   T   V   P   S   S   S   L   G   T   Q   T   Y   I
TGCAACGTGAATCACAAGCCCAGCAACACCAAGGTGGACAAGAAAGTTGAGCCCAAATCT
 C   N   V   N   H   K   P   S   N   T   K   V   D   K   K   V   E   P   K   S
TGTGACAAAACTCACACATGCCCACCGTGCCCAGCACCTGAACTCCTGGGGGGACCGTCA
 C   D   K   T   H   T   C   P   P   C   P   A   P   E   L   L   G   G   P   S
GTCTTCCTCTTCCCCCCAAAACCCAAGGACACCCTCATGATCTCCCGGACCCCTGAGGTC
 V   F   L   F   P   P   K   P   K   D   T   L   M   I   S   R   T   P   E   V
ACATGCGTGGTGGTGGACGTGAGCCACGAAGACCCTGAGGTCAAGTTCAACTGGTACGTG
 T   C   V   V   V   D   V   S   H   E   D   P   E   V   K   F   N   W   Y   V
GACGGCGTGGAGGTGCATAATGCCAAGACAAAGCCGCGGGAGGAGCAGTACAACAGCACG
 D   G   V   E   V   H   N   A   K   T   K   P   R   E   E   Q   Y   N   S   T
TACCGTGTGGTCAGCGTCCTCACCGTCCTGCACCAGGACTGGCTGAATGGCAAGGAGTAC
 Y   R   V   V   S   V   L   T   V   L   H   Q   D   W   L   N   G   K   E   Y
AAGTGCAAGGTCTCCAACAAAGCCCTCCCAGCCCCCATCGAGAAAACCATCTCCAAAGCC
 K   C   K   V   S   N   K   A   L   P   A   P   I   E   K   T   I   S   K   A
AAAGGGCAGCCCCGAGAACCACAGGTGTACACCCTGCCCCCATCCCGGGATGAGCTGACC
 K   G   Q   P   R   E   P   Q   V   Y   T   L   P   P   S   R   D   E   L   T
AAGAACCAGGTCAGCCTGACCTGCCTGGTCAAAGGCTTCTATCCCAGCGACATCGCCGTG
 K   N   Q   V   S   L   T   C   L   V   K   G   F   Y   P   S   D   I   A   V
GAGTGGGAGAGCAATGGGCAGCCGGAGAACAACTACAAGACCACGCCTCCCGTGCTGGAC
 E   W   E   S   N   G   Q   P   E   N   N   Y   K   T   T   P   P   V   L   D
TCCGACGGCTCCTTCTTCCTCTACAGCAAGCTCACCGTGGACAAGAGCAGGTGGCAGCAG
 S   D   G   S   F   F   L   Y   S   K   L   T   V   D   K   S   R   W   Q   Q
GGGAACGTCTTCTCATGCTCCGTGATGCATGAGGCTCTGCACAACCACTACACGCAGAAG
 G   N   V   F   S   C   S   V   M   H   E   A   L   H   N   H   Y   T   Q   K
AGCCTCTCCCTGTCTCCGGGTAAATGA
 S   L   S   L   S   P   G   K   *
```

Fig. 19

SEQ ID NO:57 (nucleotide)  SEQ ID NO: 14 (aminoacid)
SpeI
<u>ACTAGT</u>GCCACCATGGAATGGAGCGGGGTCTTTATCTTTCTCCTGTCAGTGACTGCAGGC
           *M  E  W  S  G  V  F  I  F  L  L  S  V  T  A  G*

GTCCACTCCCAAGTCCAGCTCCAGCAGTCTGGAGCTGAGCTCGTGAGGCCTGGGACTTCA
*V  H  S  <u>Q</u>  V  Q  L  Q  Q  S  G  A  E  L  V  R  P  G  T  S*

GTGAAGATGTCCTGCAAGGCTGCTGGATACACCTTCACTAACTACTGGATCGGATGGGTG
*V  K  M  S  C  K  A  A  G  Y  T  F  T  <u>N  Y  W  I  G</u>  W  V*

AAGCAGAGGCCTGGACATGGCCTCGAGTGGATTGGAGATATTTACCCTGGAGGAGGCTAT
*K  Q  R  P  G  H  G  L  E  W  I  G  <u>D  I  Y  P  G  G  G  Y</u>*

ACTAACTACAATGAGAAGTTCAAGGGCAAGGCCACACTGACTGCAGACACATCCTCCAGC
*<u>T  N  Y  N  E  K  F  K  G</u>  K  A  T  L  T  A  D  T  S  S  S*

ACAGCCTACATGCAGCTCAGCAGCCTGACATCTGAGGACTCTGCCATCTATTACTGTGCA
*T  A  Y  M  Q  L  S  S  L  T  S  E  D  S  A  I  Y  Y  C  A*

AGAGGAACTGGAGGCGGAGACTACTGGGGCCAAGGGACTCTGGTCACTGTCTCTGCAG*GT*
*R  <u>G  T  G  G  G  D  Y</u>  W  G  Q  G  T  L  V  T  V  S  A*

HindIII
*GAGTCCTAACTTCTCCC<u>AAGCTT</u>*

Fig. 20

SEQ ID NO:58 (nucleotide)  SEQ ID NO:16 (aminoacid)
NheI
<u>GCTAGC</u>GCCACCATGGAGACAGACACACTCCTGCTGTGGGTGCTGCTGCTCTGGGTTCCA
           *M  E  T  D  T  L  L  L  W  V  L  L  L  W  V  P*

GGCTCCACTGGCGACATTGTGCTGACACAGTCTCCTGCTTCCCTGGCTGTGTCTCTGGGG
*G  S  T  G  <u>D</u>  I  V  L  T  Q  S  P  A  S  L  A  V  S  L  G*

CAGAGGGCCACCATCTCATGCAGGGCCAGCCAAAGTGTCAGTACATCTAGCTATAGTTAT
*Q  R  A  T  I  S  C  <u>R  A  S  Q  S  V  S  T  S  S  Y  S  Y</u>*

ATGCACTGGTACCAACAGAAACCAGGACAGCCACCCAAACTCCTCATCAAGTATGCATCC
*<u>M  H</u>  W  Y  Q  Q  K  P  G  Q  P  P  K  L  L  I  K  <u>Y  A  S</u>*

AACCTGGAATCTGGGGTCCCTGCCAGATTCAGTGGCAGTGGGTCTGGGACAGACTTCACC
*<u>N  L  E  S</u>  G  V  P  A  R  F  S  G  S  G  S  G  T  D  F  T*

CTCAACATCCATCCTGTGGAGGAGGAGGATACTGCAACATATTACTGTCAGCACAGTTGG
*L  N  I  H  P  V  E  E  E  D  T  A  T  Y  Y  C  <u>Q  H  S  W</u>*

GAGATTCCCTACACCTTCGGAGGGGGGACCAAGCTGGAAATCAAA*CGTAAGTAGTCTTCT*
*<u>E  I  P  Y  T</u>  F  G  G  G  T  K  L  E  I  K*

EcoRI
*CAAC<u>GAATTC</u>*

Fig. 21

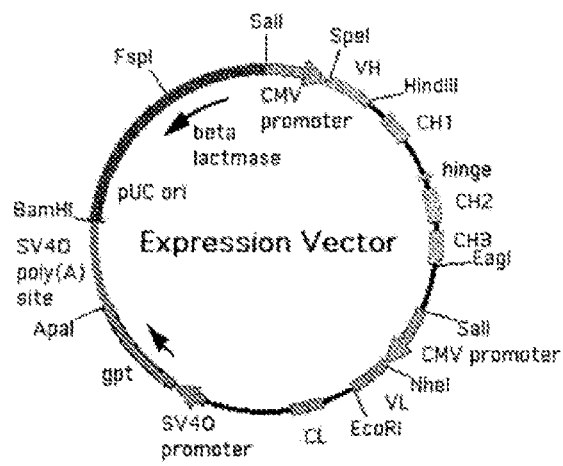

Fig. 22

```
              1          2          3
              123456789 0123456789 0123456789 0123456789
2EF VH        QVQLQQSGA  ELVRPGTSVK MSCKAAGYTF TNYWIGWVKQ
Hu2EF VH4     QVQLVQSGA  EVKKPGASVK VSCKASGYTF TNYWIGWVRQ
Hu2EF VH7     QVQLVQSGA  EVKKPGASVK VSCKASGYTF TNYWIGWVKQ
M17751.1 VH   QVQLVQSGA  EVKKPGASVK VSCKASGYTF T-----WVRQ 4          5          6          7
              0123456789 01223456789 0123456789 0123456789
2EF VH        RPGHGLEWIG DIYPGGGYTNY NEKFKGKATL TADTSSSTAY
Hu2EF VH4     APGQGLEWIG DIYPGGGYTNY NEKFKGRATL TADTSASTAY
Hu2EF VH7     APGQGLEWIG DIYPGGGYTNY NEKFKGRATL TADTSASTAY
M17751.1 VH   APGQRLEWMG ----------- ------RVTI TRDTSASTAY 8            9          10         11
              0122223456789 0123456789 0123456789 0123
2EF VH        MQLSSLTSEDSAI YYCARGTGGG DYWGQGTLV TVSA(aa 20-135 of
                                                     SEQ ID NO:14)
Hu2EF VH4     MELSSLRSEDTAV YYCARGTGGG DYWGQGTLV TVSS(aa 20-135 of
                                                     SEQ ID NO:22)
Hu2EF VH7     MELSSLRSEDTAV YYCARGTGGG DYWGQGTLV TVSS(aa 20-135 of
                                                     SEQ ID NO:26)
M17751.1 VH   MELSSLRSEDTAV YYCAR----- --WGQGTLV TVSS(SEQ ID NO:88)
```

Fig. 23

```
                        1           2           3
              123456789 0123456789 0123456789 0123456789
2EF VH        QVQLQQSGA ELVRPGTSVK MSCKAAGYTF TNYWIGWVKQ
Hu2EF VH5     QVQLVQSGA EVKKPGASVK VSCKASGYTF INYWIGWVRQ
L02325.1 VH   QVQLVQSGA EVKKPGASVK VSCKASGYTF T-----WVRQ 4           5           6           7
              0123456789 0123456789 0123456789 0123456789
2EF VH        RPGHGLEWIG DIYPGGGYTNY NEKFKGKATL TADTSSSTAY
Hu2EF VH5     APGQGLEWIG DIYPGGGYTNY NEKFKGRATL TADTSTSTAY
L02325.1 VH   APGQGLEWMG ---------- ------RVTM TRDTSTSTVY 8           9           10          11
              0122223456789 0123456789 0123456789 0123
2EF VH        MQLSSLTSEDSAI YYCARGTGGG DYWGQGTLV TVSA(aa 20-135 of
                                                     SEQ ID NO:14)
Hu2EF VH5     MELSSLRSEDTAV YYCARGTGGG DYWGQGTLV TVSS(aa 20-135 of
                                                     SEQ ID NO:24)
L02325.1 VH   MELSSLRSEDTAV YYCAR----- --WGQGTLV TVSS(SEQ ID NO:89)
```

Fig. 24

```
                        1           2              3
              123456789 0123456789 01234567777789 0123456789
2EF VL        DIVLTQSPA SLAVSLGQPA TISCRASQSVSTSS YSYMHWYQQK
Hu2EF VL1     DIVMTQSPD SLAVSLGERA TINCRASQSVSTSS YSYMHWYQQK
Hu2EF VL2     DIVLTQSPD SLAVSLGERA TINCRASQSVSTSS YSYMHWYQQK
Z46622.1 VL   DIVMTQSPD SLAVSLGERA TINC---------- -----WYQQK 4           5           6           7
              0123456789 0123456789 0123456789 0123456789
2EF VL        PGQPPKLLIK YASNLESGVP ARFSGSGSGT DFTLNIHPVE
Hu2EF VL1     PGQPPKLLIK YASNLESGVP DRFSGSGSGT DFTLTISSLQ
Hu2EF VL2     PGQPPKLLIK YASNLESGVP DRFSGSGSGT DFTLTISSLQ
Z46622.1 VL   PGQPPKLLIY -------GVP DRFSGSGSGT DFTLTISSLQ 8           9           10
              0123456789 0123456789 01234567
2EF VL        EEDTATYYCQ HSWEIPYTFG GGTKLEIK(aa 21-131 of SEQ ID
                                            NO:16)
Hu2EF VL1     AEDVAVYYCQ HSWEIPYTFG QGTKLEIK(aa 21-131 of SEQ ID
                                            NO:28
Hu2EF VL2     AEDVAVYYCQ HSWEIPYTFG GGTKLEIK(aa 21-131 of SEQ ID
                                            NO:30)
Z46622.1 VL   AEDVAVYYC- --------FG QGTKLEIK(SEQ ID NO:91)
```

Fig. 25

SEQ ID NO:59 (nucleotide)　SEQ ID NO:22 (aminoacid)
SpeI
<u>ACTAGT</u>GCCACCATGGAATGGAGCGGGGTCTTTATCTTTCTCCTGTCAGTGACTGCAGGC
　　　　　　　*M　E　W　S　G　V　F　I　F　L　L　S　V　T　A　G*

GTCCACTCCCAAGTCCAGCTCGTGCAGTCTGGAGCTGAAGTGAAGAAACCTGGGGCTTCA
*V　H　S　<u>Q</u>　V　Q　L　V　Q　S　G　A　E　V　K　K　P　G　A　S*

GTGAAGGTGTCCTGCAAGGCTTCTGGATACACCTTCACTAACTACTGGATCGGATGGGTC
*V　K　V　S　C　K　A　S　G　Y　T　F　T　<u>N　Y　W　I　G</u>　W　V*

AGACAGGCCCCTGGACAGGGCCTCGAGTGGATTGGAGATATTTACCCTGGAGGAGGCTAT
*R　Q　A　P　G　Q　G　L　E　W　I　G　<u>D　I　Y　P　G　G　G　Y*

ACTAACTACAATGAGAAGTTCAAGGGCAGAGCCACACTGACTGCAGACACATCCGCCAGC
*T　N　Y　N　E　K　F　K　G</u>　R　A　T　L　T　A　D	T　S　A	S*

ACAGCCTACATGGAGCTCAGCAGCCTGAGATCTGAGGACACTGCCGTGTATTACTGTGCA
*T　A　Y　M　E　L　S　S　L　R　S　E	D	T	A	V	Y	Y	C	A*

AGAGGAACTGGAGGCGGAGACTACTGGGGCCAAGGGACTCTGGTCACTGTCTCTTCAG*GT*
*R　<u>G　T　G　G　G	D	Y</u>	W	G	Q	G	T	L	V	T	V	S	S*

HindIII
*GAGTCCTAACTTCTCCC<u>AAGCTT</u>*

Fig. 26

SEQ ID NO:60 (nucleotide)　SEQ ID NO:24 (aminoacid)
SpeI
<u>ACTAGT</u>GCCACCATGGAATGGAGCGGGGTCTTTATCTTTCTCCTGTCAGTGACTGCAGGC
　　　　　　　*M　E　W　S　G	V	F	I	F	L	L	S	V	T	A	G*

GTCCACTCCCAAGTCCAGCTCGTGCAGTCTGGAGCTGAAGTGAAGAAACCTGGGGCTTCA
*V　H　S　<u>Q</u>　V	Q	L	V	Q	S	G	A	E	V	K	K	P	G	A	S*

GTGAAGGTGCCTGCAAGGCTTCTGGATACACCTTCACTAACTACTGGATCGGATGGGTC
*V	K	V	S	C	K	A	S	G	Y	T	F	T	<u>N	Y	W	I	G</u>	W	V*

AGACAGGCCCCTGGACAGGGCCTCGAGTGGATTGGAGATATTTACCCTGGAGGAGGCTAT
*R	Q	A	P	G	Q	G	L	E	W	I	G	<u>D	I	Y	P	G	G	G	Y*

ACTAACTACAATGAGAAGTTCAAGGGCAGAGCCACACTGACTGCAGACACATCCACCAGC
*T	N	Y	N	E	K	F	K	G</u>	R	A	T	L	T	A	D	T	S	T	S*

ACAGCCTACATGGAGCTCAGCAGCCTGAGATCTGAGGACACTGCCGTGTATTACTGTGCA
*T	A	Y	M	E	L	S	S	L	R	S	E	D	T	A	V	Y	Y	C	A*

AGAGGAACTGGAGGCGGAGACTACTGGGGCCAAGGGACTCTGGTCACTGTCTCTTCAG*GT*
*R	<u>G	T	G	G	G	D	Y</u>	W	G	Q	G	T	L	V	T	V	S	S*

HindIII
*GAGTCCTAACTTCTCCC<u>AAGCTT</u>*

Fig. 27

SEQ ID NO:61 (nucleotide)   SEQ ID NO:28 (aminoacid)

```
NheI
GCTAGCGCCACCATGGAGACAGACACACTCCTGCTGTGGGTGCTGCTGCTCTGGGTTCCA
          M   E   T   D   T   L   L   W   V   L   L   L   W   V   P

GGCTCCACTGGCGACATTGTGATGACACAGTCTCCTGACTCCCTGGCTGTGTCTCTGGGG
 G   S   T   G   D   I   V   M   T   Q   S   P   D   S   L   A   V   S   L   G

GAGAGGGCCACCATCAACTGCAGGGCCAGCCAAAGTGTCAGTACATCTAGCTATAGTTAT
 E   R   A   T   I   N   C   R   A   S   Q   S   V   S   T   S   S   Y   S   Y

ATGCACTGGTACCAACAGAAACCAGGACAGCCACCCAAACTCCTCATCAAGTATGCATCC
 M   H   W   Y   Q   Q   K   P   G   Q   P   P   K   L   L   I   K   Y   A   S

AACCTGGAATCTGGGGTCCCTGACAGATTCAGTGGCAGTGGGTCTGGGACAGACTTCACC
 N   L   E   S   G   V   P   D   R   F   S   G   S   G   S   G   T   D   F   T

CTCACCATCAGCTCCCTGCAGGCCGAGGATGTGGCAGTCTATTACTGTCAGCACAGTTGG
 L   T   I   S   S   L   Q   A   E   D   V   A   V   Y   Y   C   Q   H   S   W

GAGATTCCCTACACCTTCGGACAGGGGACCAAGCTGGAAATCAAACGTAAGTAGTCTTCT
 E   I   P   Y   T   F   G   Q   G   T   K   L   E   I   K

EcoRI
CAACGAATTC
```

Fig. 28

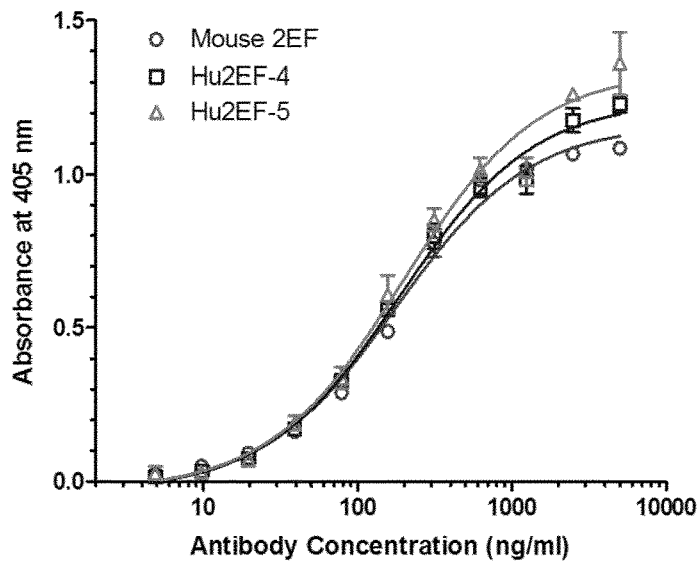

Fig. 29

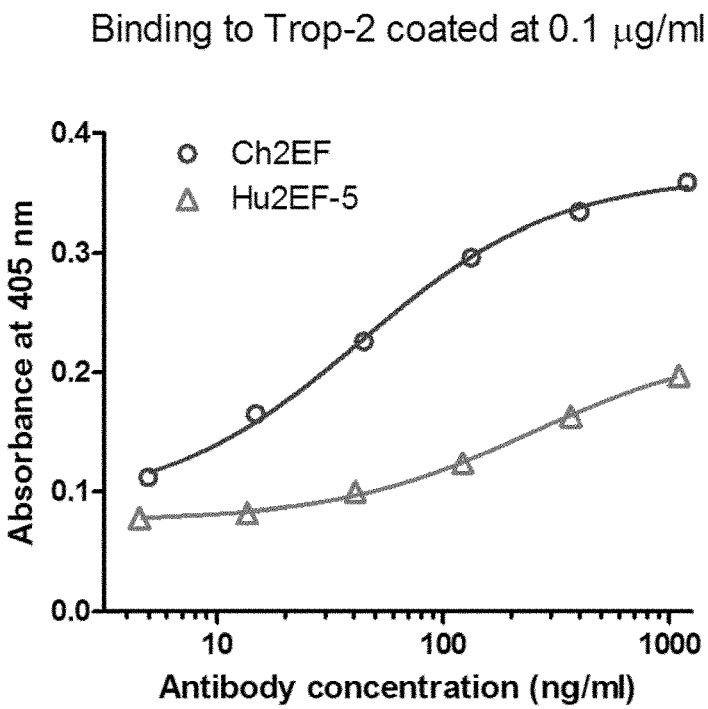

Fig. 32

```
SEQ ID NO:67 (nucleotide)   SEQ ID NO:26(aminoacid)
SpeI
ACTAGTGCCACCATGGAATGGAGCGGGGTCTTTATCTTTCTCCTGTCAGTGACTGCAGGC
             M  E  W  S  G  V  F  I  F  L  L  S  V  T  A  G GTCCACTCCCAAGTCCAGCTCGTGCAGTCTGGAGCTGAAGTGAAGAAACCTGGGGCTTCA
 V  H  S  Q  V  Q  L  V  Q  S  G  A  E  V  K  K  P  G  A  S GTGAAGGTGTCCTGCAAGGCTTCTGGATACACCTTCACTAACTACTGGATCGGATGGGTC
 V  K  V  S  C  K  A  S  G  Y  T  F  T  N  Y  W  I  G  W  V AAACAGGCCCCTGGACAGGGCCTCGAGTGGATTGGAGATATTTACCCTGGAGGAGGCTAT
 K  Q  A  P  G  Q  G  L  E  W  I  G  D  I  Y  P  G  G  G  Y ACTAACTACAATGAGAAGTTCAAGGGCAGAGCCACACTGACTGCAGACACATCCGCCAGC
 T  N  Y  N  E  K  F  K  G  R  A  T  L  T  A  D  T  S  A  S ACAGCCTACATGGAGCTCAGCAGCCTGAGATCTGAGGACACTGCCGTGTATTACTGTGCA
 T  A  Y  M  E  L  S  S  L  R  S  E  D  T  A  V  Y  Y  C  A AGAGGAACTGGAGGCGGAGACTACTGGGGCCAAGGGACTCTGGTCACTGTCTCTTCAGGT
 R  G  T  G  G  G  D  Y  W  G  Q  G  T  L  V  T  V  S  S HindIII
GAGTCCTAACTTCTCCCAAGCTT
```

Fig. 33

SEQ ID NO:68 (nucleotide)   SEQ ID NO:30 (aminoacid)
NheI
GCTAGCGCCACCATGGAGACAGACACACTCCTGCTGTGGGTGCTGCTGCTCTGGGTTCCA
           M   E   T   D   T   L   L   L   W   V   L   L   W   V   P GGCTCCACTGGCGACATTGTGCTGACACAGTCTCCTGACTCCCTGGCTGTGTCTCTGGGG
 G   S   T   G   D   I   V   L   T   Q   S   P   D   S   L   A   V   S   L   G GAGAGGGCCACCATCAACTGCAGGGCCAGCCAAAGTGTCAGTACATCTAGCTATAGTTAT
 E   R   A   T   I   N   C   R   A   S   Q   S   V   S   T   S   S   Y   S   Y ATGCACTGGTACCAACAGAAACCAGGACAGCCACCCAAACTCCTCATCAAGTATGCATCC
 M   H   W   Y   Q   Q   K   P   G   Q   P   P   K   L   L   I   K   Y   A   S AACCTGGAATCTGGGGTCCCTGACAGATTCAGTGGCAGTGGGTCTGGGACAGACTTCACC
 N   L   E   S   G   V   P   D   R   F   S   G   S   G   S   G   T   D   F   T CTCACCATCAGCTCCCTGCAGGCCGAGGATGTGGCAGTCTATTACTGTCAGCACAGTTGG
 L   T   I   S   S   L   Q   A   E   D   V   A   V   Y   Y   C   Q   H   S   W GAGATTCCCTACACCTTCGGAGGCGGGACCAAGCTGGAAATCAAA*GTAAGTAGTCTTCT*
 E   I   P   Y   T   F   G   G   G   T   K   L   E   I   K EcoRI
*CAACGAATTC*

Fig. 34

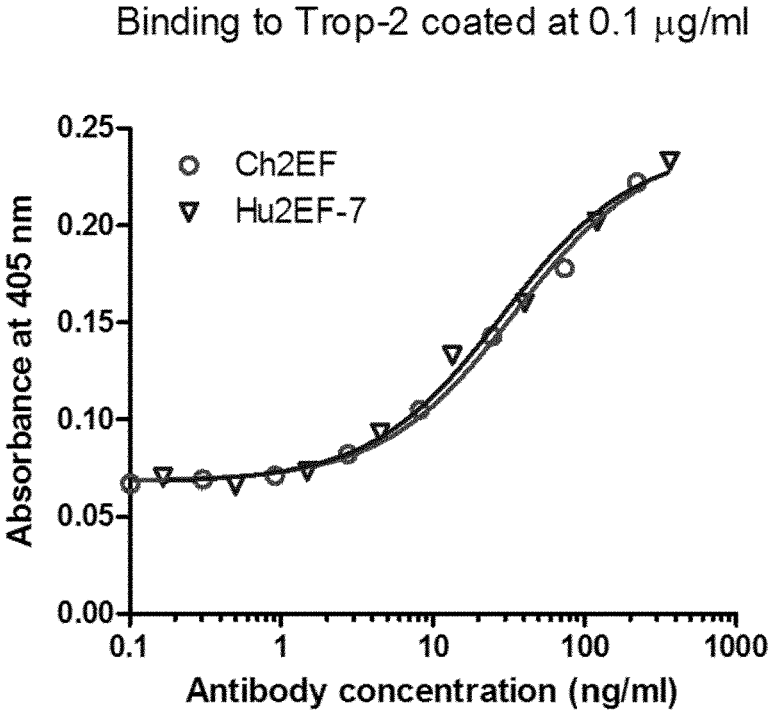

Fig. 35

SEQ ID NO:72 (nucleotide)   SEQ ID NO:18 (aminoacid)
SpeI
<u>ACTAGT</u>ACCACCATGGAATGGAACTGGGTCGTTCTCTTCCTCCTGTCATTAACTGCAGGT
            *M  E  W  N  W  V  V  L  F  L  L  S  L  T  A  G*

GTCTATTCCCAGGGTCAGATGCAGCAGTCTGGAGCTGAGCTGGTGAAGCCTGGGGCTTCA
*V  Y  S  Q̲  G  Q  M  Q  Q  S  G  A  E  L  V  K  P  G  A  S*

GTGAAGCTGTCCTGCAAGACTTCTGGCTTCACCTTCAGCAGTAGCTATATAAGTTGGTTG
V  K  L  S  C  K  T  S  G  F  T  F  S  <u>S  S  Y  I  S  W</u>  L

AAGCAGAAGCCTCGACAGAGTCTTGAGTGGATTGCATGGATTTATGCTGGAACTGGTGGT
K  Q  K  P  R  Q  S  L  E  W  I  A  <u>W  I  Y  A  G  T  G  G</u>

ACTAGCTATAATCAGAAGTTCACAGGCAAGGCCCAACTGACTGTAGACACATCCTCCAGC
<u>T  S  Y  N  Q  K  F  T  G</u>  K  A  Q  L  T  V  D  T  S  S  S

ACAGCCTACATGCAACTCAGCAGCCTGACATCTGAGGACTCTGCCATCTATTACTGTGCA
T  A  Y  M  Q  L  S  S  L  T  S  E  D  S  A  I  Y  Y  C  A

AGACATAACCCTCGTTACTATGCTATGGACTACTGGGGTCAAGGAACCTCAGTCACCGTC
R  <u>H  N  P  R  Y  Y  A  M  D  Y</u>  W  G  Q  G  T  S  V  T  V

HindIII
TCCTCAG*GTAAGAATGGCCTCTC*<u>*AAGCTT*</u>
S  S

Fig. 39

SEQ ID NO:75 (nucleotide)   SEQ ID NO:20 (aminoacid)

NheI
<u>GCTAGC</u>ACCACCATGTTCTCACTAGCTCTTCTCCTCAGTCTTCTTCTCCTCTGTGTCTCT
             *M  F  S  L  A  L  L  L  S  L  L  L  L  C  V  S*

GATTCTAGGGCAGAAACAACTGTGACCCAGTCTCCAGCATCCCTGTCCATGGCTATAGGA
*D  S  R  A  E̲  T  T  V  T  Q  S  P  A  S  L  S  M  A  I  G*

GAAAAAGTCACCATCAGATGCATAACCAGCACTGATATTGATGATGATATGAACTGGTAC
E  K  V  T  I  R  C  <u>I  T  S  T  D  I  D  D  D  M  N  W</u>  Y

CAGCAGAAGCCAGGGGAACCTCCTAAGCTCCTTATTTCAGAAGGCAATACTCTTCGTCCT
Q  Q  K  P  G  E  P  P  K  L  L  I  <u>S  E  G  N  T  L  R  P</u>

GGAGTCCCATCCCGATTCTCCAGCAGTGGCTATGGTACAGATTTTGTTTTTACAATTGAA
G  V  P  S  R  F  S  S  S  G  Y  G  T  D  F  V  F  T  I  E

AACATGCTCTCAGAAGATGTTGCAGATTACTACTGTTTGCAAAGTGATAACTTGCCGTAC
N  M  L  S  E  D  V  A  D  Y  Y  C  <u>L  Q  S  D  N  L  P  Y</u>

EcoRI
ACGTTCGGAGGGGGGACCAAGCTGGAAATCAAAC*GTAAGTAGAATCCAAA*<u>*GAATTC*</u>
<u>T</u>  F  G  G  G  T  K  L  E  I  K

Fig. 40

```
                         1          2          3
                123456789 0123456789 0123456789 0123456789
2G10 VH         QGQMQQSGA ELVKPGASVK LSCKTSGFTF SSSYISWLKQ
Hu2G10 VH1      QVQLVQSGA EVKKPGASVK VSCKASGFTF SSSYISWLRQ
Hu2G10 VH2      QVQLVQSGA EVKKPGASVK VSCKASGFTF SSSYISWLRQ
X65888.1 VH     QVQLVQSGA EVKKPGASVK VSCKASGYTF T-----WVRQ 4          5          6          7
                0123456789 0123456789 0123456789 0123456789
2G10 VH         KPRQSLEWIA WIYAGTGGTS YNQKFTGKAQ LTVDTSSSTA
Hu2G10 VH1      APGQRLEWIA WIYAGTGGTS YNQKFTGKAT LTVDTSASTA
Hu2G10 VH2      APGQRLEWIA WIYAGTGGTS YNQKFTGRVT LTVDTSASTA
X65888.1 VH     APGQRLEWMG ---------- -------RVT ITRDTSASTA 8          9         10         11
                0123456789 0123456789 0123456789 0123456789
2G10 VH         YMQLSSLTSE DSAIYYCARH NPRYYAMDYW GQGTSVTVSS(aa 20-138 of
                                                           SEQ ID NO:18)
Hu2G10 VH1      YMELSSLRSE DTAVYYCARH NPRYYAMDYW GQGTTVTVSS(aa 20-138 of
                                                           SEQ ID NO:32)
Hu2G10 VH2      YMELSSLRSE DTAVYYCARH NPRYYAMDYW GQGTTVTVSS(aa 20-138 of
                                                           SEQ ID NO:34)
X65888.1 VH     YMELSSLRSE DTAVYYCAR- ---------W GQGTTVTVSS(SEQ ID NO:90)
```

Fig. 41

```
                         1          2          3
                123456789 0123456789 0123456789 0123456789
2G10 VL         ETTVTQSPA SLSMAIGEKV TIRCITSTDI DDDMNWYQQK
Hu2G10 VL1      DIQMTQSPS SLSASVGDRV TITCITSTDI DDDMNWYQQK
Hu2G10 VL2      DIQMTQSPS SLSASVGDRV TITCITSTDI DDDMNWYQQK
Hu2G10 VL3      DTQMTQSPS SLSASVGDRV TITCITSTDI DDDMNWYQQK
AY043146.1 VL   DIQMTQSPS SLSASVGDRV TITC------ -----WYQQK 4          5          6          7
                0123456789 0123456789 0123456789 0123456789
2G10 VL         PGEPPKLLIS EGNTLRPGVP SRFSSSGYGT DFVFTIENML
Hu2G10 VL1      PGKAPKLLIS EGNTLRPGVP SRFSGSGYGT DFTFTISSLQ
Hu2G10 VL2      PGKAPKLLIS EGNTLRPGVP SRFSGSGSGT DFTFTISSLQ
Hu2G10 VL3      PGKAPKLLIS EGNTLRPGVP SRFSGSGYGT DFTFTISSLQ
AY043146.1 VL   PGKAPKLLIY -------GVP SRFSGSGSGT DFTFTISSLQ 8          9         10
                0123456789 0123456789 01234567
2G10 VL         SEDVADYYCL QSDNLPYTFG GGTKLEIK(aa 21-127 SEQ ID NO:20)
Hu2G10 VL1      PEDIATYYCL QSDNLPYTFG GGTKVEIK(aa 21-127 SEQ ID NO:36)
Hu2G10 VL2      PEDIATYYCL QSDNLPYTFG GGTKVEIK(aa 21-127 SEQ ID NO:38)
Hu2G10 VL3      PEDIATYYCL QSDNLPYTFG GGTKVEIK(aa 21-127 SEQ ID NO:40)
AY043146.1 VL   PEDIATYYC- --------FG GGTKVEIK(SEQ ID NO:92)
```

Fig. 42

SEQ ID NO:78 (nucleotide)   SEQ ID NO:32(aminoacid)
SpeI
ACTAGTACCACCATGGAATGGAACTGGGTCGTTCTCTTCCTCCTGTCACTGACTGCAGGC
          M   E   W   N   W   V   V   L   F   L   L   S   L   T   A   G GTCTATTCCCAAGTGCAGCTCGTCCAGTCTGGAGCTGAAGTCAAAAAGCCTGGGGCTTCA
 V   Y   S   Q   V   Q   L   V   Q   S   G   A   E   V   K   K   P   G   A   S GTGAAAGTCTCCTGCAAGGCTTCTGGCTTCACCTTCAGCAGTAGCTATATCAGTTGGTTG
 V   K   V   S   C   K   A   S   G   T   F   S   S   S   Y   I   S   W   L AGGCAGGCCCCTGGACAGAGACTTGAGTGGATTGCATGGATTTATGCTGGAACTGGCGGA
 R   Q   A   P   G   Q   R   L   E   W   I   A   W   I   Y   A   G   T   G   G ACTAGCTATAATCAGAAGTTCACAGGCAAGGCCACACTGACTGTAGACACATCCGCCAGC
 T   S   Y   N   Q   K   F   T   G   K   A   T   L   T   V   D   T   S   A   S ACAGCCTACATGGAACTCAGCAGCCTGAGATCTGAGGACACTGCCGTCTATTACTGTGCA
 T   A   Y   M   E   L   S   S   L   R   S   E   D   T   A   V   Y   Y   C   A AGACATAACCCTCGTTACTATGCTATGGACTACTGGGGCCAAGGAACCACAGTCACCGTC
 R   H   N   P   R   Y   Y   A   M   D   Y   W   G   Q   G   T   T   V   T   V HindIII
TCCTCAG*GTAAGAATGGCCTCTC*AAGCTT
 S   S

Fig. 43

SEQ ID NO:79 (nucleotide)   SEQ ID NO:34(aminoacid)
SpeI
ACTAGTACCACCATGGAATGGAACTGGGTCGTTCTCTTCCTCCTGTCACTGACTGCAGGC
          M   E   W   N   W   V   V   L   F   L   L   S   L   T   A   G GTCTATTCCCAAGTGCAGCTCGTCCAGTCTGGAGCTGAAGTCAAAAAGCCTGGGGCTTCA
 V   Y   S   Q   V   Q   L   V   Q   S   G   A   E   V   K   K   P   G   A   S GTGAAAGTCTCCTGCAAGGCTTCTGGCTTCACCTTCAGCAGTAGCTATATCAGTTGGTTG
 V   K   V   S   C   K   A   S   G   T   F   S   S   S   Y   I   S   W   L AGGCAGGCCCCTGGACAGAGACTTGAGTGGATTGCATGGATTTATGCTGGAACTGGCGGA
 R   Q   A   P   G   Q   R   L   E   W   I   A   W   I   Y   A   G   T   G   G ACTAGCTATAATCAGAAGTTCACAGGCAGAGTCACACTGACTGTAGACACATCCGCCAGC
 T   S   Y   N   Q   K   F   T   G   R   V   T   L   T   V   D   T   S   A   S ACAGCCTACATGGAACTCAGCAGCCTGAGATCTGAGGACACTGCCGTCTATTACTGTGCA
 T   A   Y   M   E   L   S   S   L   R   S   E   D   T   A   V   Y   Y   C   A AGACATAACCCTCGTTACTATGCTATGGACTACTGGGGCCAAGGAACCACAGTCACCGTC
 R   H   N   P   R   Y   Y   A   M   D   Y   W   G   Q   G   T   T   V   T   V HindIII
TCCTCAG*GTAAGAATGGCCTCTC*AAGCTT
  S   S

Fig. 44

SEQ ID NO:80 (nucleotide)   SEQ ID NO:36 (aminoacid)
NheI
GCTAGCACCACCATGTTCTCACTGGCTCTGCTCCTCAGTCTGCTGCTCCTCTGTGTCTCT
          M   F   S   L   A   L   L   L   S   L   L   L   C   V   S GATTCTAGAGCAGACATCCAGATGACCCAGTCTCCAAGCTCCCTGTCCGCCAGCGTGGGA
 D   S   R   A   D   I   Q   M   T   Q   S   P   S   S   L   S   A   S   V   G GATAGAGTCACCATCACATGCATCACCAGCACTGATATTGATGATGATATGAACTGGTAC
 D   R   V   T   I   T   C   I   T   S   T   D   I   D   D   D   M   N   W   Y CAGCAGAAGCCAGGGAAAGCTCCTAAGCTCCTGATTTCAGAAGGCAATACTCTGCGCCCT
 Q   Q   K   P   G   K   A   P   K   L   L   I   S   E   G   N   T   L   R   P GGAGTCCCATCCCGATTCTCCGGCAGTGGCTATGGAACAGATTTTACCTTTACAATTAGC
 G   V   P   S   R   F   S   G   S   G   Y   G   T   D   F   T   F   T   I   S TCCCTGCAGCCAGAAGATATTGCAACCTACTACTGTTTGCAAAGTGATAACCTGCCCTAC
 S   L   Q   P   E   D   I   A   T   Y   Y   C   L   Q   S   D   N   L   P   Y EcoRI
ACCTTCGGAGGGGGGACCAAAGTCGAAATCAAAC*GTAAGTAGAATCCAAAG*AATTC
 T   F   G   G   G   T   K   V   E   I   K

Fig. 45

SEQ ID NO:81 (nucleotide)   SEQ ID NO:38 (aminoacid)

NheI
GCTAGCACCACCATGTTCTCACTGGCTCTGCTCCTCAGTCTGCTGCTCCTCTGTGTCTCT
          M   F   S   L   A   L   L   L   S   L   L   L   C   V   S

GATTCTAGAGCAGACATCCAGATGACCCAGTCTCCAAGCTCCCTGTCCGCCAGCGTGGGA
 D   S   R   A   D   I   Q   M   T   Q   S   P   S   S   L   S   A   S   V   G

GATAGAGTCACCATCACATGCATCACCAGCACTGATATTGATGATGATATGAACTGGTAC
 D   R   V   T   I   T   C   I   T   S   T   D   I   D   D   D   M   N   W   Y

CAGCAGAAGCCAGGGAAAGCTCCTAAGCTCCTGATTTCAGAAGGCAATACTCTGCGCCCT
 Q   Q   K   P   G   K   A   P   K   L   L   I   S   E   G   N   T   L   R   P

GGAGTCCCATCCCGATTCTCCGGCAGTGGCTCTGGAACAGATTTTACCTTTACAATTAGC
 G   V   P   S   R   F   S   G   S   G   S   G   T   D   F   T   F   T   I   S

TCCCTGCAGCCAGAAGATATTGCAACCTACTACTGTTTGCAAAGTGATAACCTGCCCTAC
 S   L   Q   P   E   D   I   A   T   Y   Y   C   L   Q   S   D   N   L   P   Y

EcoRI
ACCTTCGGAGGGGGGACCAAAGTCGAAATCAAAC*GTAAGTAGAATCCAAAG*AATTC
 T   F   G   G   G   T   K   V   E   I   K

Fig. 46

SEQ ID NO:82 (nucleotide)   SEQ ID NO:40 (aminoacid)

```
NheI
GCTAGCACCACCATGTTCTCACTGGCTCTGCTCCTCAGTCTGCTGCTCCTCTGTGTCTCT
          M   F   S   L   A   L   L   S   L   L   L   L   C   V   S

GATTCTAGAGCAGACACCCAGATGACCCAGTCTCCAAGCTCCCTGTCCGCCAGCGTGGGA
D   S   R   A   D   T   Q   M   T   Q   S   P   S   S   L   S   A   S   V   G

GATAGAGTCACCATCACATGCATCACCAGCACTGATATTGATGATGATATGAACTGGTAC
D   R   V   T   I   T   C   I   T   S   T   D   I   D   D   D   M   N   W   Y

CAGCAGAAGCCAGGGAAAGCTCCTAAGCTCCTGATTTCAGAAGGCAATACTCTGCGCCCT
Q   Q   K   P   G   K   A   P   K   L   L   I   S   E   G   N   T   L   R   P

GGAGTCCCATCCCGATTCTCCGGCAGTGGCTATGGAACAGATTTTACCTTTACAATTAGC
G   V   P   S   R   F   S   G   S   G   Y   G   T   D   F   T   F   T   I   S

TCCCTGCAGCCAGAAGATATTGCAACCTACTACTGTTTGCAAAGTGATAACCTGCCCTAC
S   L   Q   P   E   D   I   A   T   Y   Y   C   L   Q   S   D   N   L   P   Y

EcoRI
ACCTTCGGAGGGGGGACCAAAGTCGAAATCAAACGTAAGTAGAATCCAAAGAATTC
T   F   G   G   G   T   K   V   E   I   K
```

Fig. 47

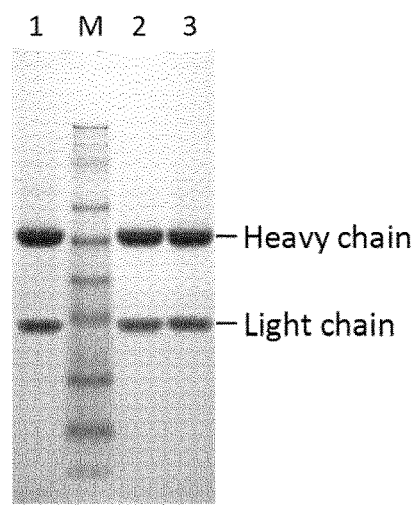

Fig. 48

SEQ ID NO:83 (nucleotide)   SEQ ID NO:84 (aminoacid)

```
ATGGAATGGAACTGGGTCGTTCTCTTCCTCCTGTCATTAACTGCAGGTGTCTATTCCCAG
 M  E  W  N  W  V  V  L  F  L  L  S  L  T  A  G  V  Y  S  Q
GGTCAGATGCAGCAGTCTGGAGCTGAGCTGGTGAAGCCTGGGGCTTCAGTGAAGCTGTCC
 G  Q  M  Q  Q  S  G  A  E  L  V  K  P  G  A  S  V  K  L  S
TGCAAGACTTCTGGCTTCACCTTCAGCAGTAGCTATATAAGTTGGTTGAAGCAGAAGCCT
 C  K  T  S  G  F  T  F  S  S  S  Y  I  S  W  L  K  Q  K  P
CGACAGAGTCTTGAGTGGATTGCATGGATTTATGCTGGAACTGGTGGTACTAGCTATAAT
 R  Q  S  L  E  W  I  A  W  I  Y  A  G  T  G  G  T  S  Y  N
CAGAAGTTCACAGGCAAGGCCCAACTGACTGTAGACACATCCTCCAGCACAGCCTACATG
 Q  K  F  T  G  K  A  Q  L  T  V  D  T  S  S  S  T  A  Y  M
CAACTCAGCAGCCTGACATCTGAGGACTCTGCCATCTATTACTGTGCAAGACATAACCCT
 Q  L  S  S  L  T  S  E  D  S  A  I  Y  Y  C  A  R  H  N  P
CGTTACTATGCTATGGACTACTGGGGTCAAGGAACCTCAGTCACCGTCTCCTCAGCCTCC
 R  Y  Y  A  M  D  Y  W  G  Q  G  T  S  V  T  V  S  S  A  S
ACCAAGGGCCCATCGGTCTTCCCCCTGGCACCCTCCTCCAAGAGCACCTCTGGGGGCACA
 T  K  G  P  S  V  F  P  L  A  P  S  S  K  S  T  S  G  G  T
GCGGCCCTGGGCTGCCTGGTCAAGGACTACTTCCCCGAACCGGTGACGGTGTCGTGGAAC
 A  A  L  G  C  L  V  K  D  Y  F  P  E  P  V  T  V  S  W  N
TCAGGCGCCCTGACCAGCGGCGTGCACACCTTCCCGGCTGTCCTACAGTCCTCAGGACTC
 S  G  A  L  T  S  G  V  H  T  F  P  A  V  L  Q  S  S  G  L
TACTCCCTCAGCAGCGTGGTGACCGTGCCCTCCAGCAGCTTGGGCACCCAGACCTACATC
 Y  S  L  S  S  V  V  T  V  P  S  S  S  L  G  T  Q  T  Y  I
TGCAACGTGAATCACAAGCCCAGCAACACCAAGGTGGACAAGAAAGTTGAGCCCAAATCT
 C  N  V  N  H  K  P  S  N  T  K  V  D  K  K  V  E  P  K  S
TGTGACAAAACTCACACATGCCCACCGTGCCCAGCACCTGAACTCCTGGGGGGACCGTCA
 C  D  K  T  H  T  C  P  P  C  P  A  P  E  L  L  G  G  P  S
GTCTTCCTCTTCCCCCCAAAACCCAAGGACACCCTCATGATCTCCCGGACCCCTGAGGTC
 V  F  L  F  P  P  K  P  K  D  T  L  M  I  S  R  T  P  E  V
ACATGCGTGGTGGTGGACGTGAGCCACGAAGACCCTGAGGTCAAGTTCAACTGGTACGTG
 T  C  V  VV D  V  S  H  E  D  P  E  V  K  F  N  W  Y  V
GACGGCGTGGAGGTGCATAATGCCAAGACAAAGCCGCGGGAGGAGCAGTACAACAGCACG
 D  G  V  E  V  H  N  A  K  T  K  P  R  E  E  Q  Y  N  S  T
TACCGTGTGGTCAGCGTCCTCACCGTCCTGCACCAGGACTGGCTGAATGGCAAGGAGTAC
 Y  R  V  V  S  V  L  T  V  L  H  Q  D  W  L  N  G  K  E  Y
AAGTGCAAGGTCTCCAACAAAGCCCTCCCAGCCCCCATCGAGAAAACCATCTCCAAAGCC
 K  C  K  V  S  N  K  A  L  P  A  P  I  E  K  T  I  S  K  A
AAAGGGCAGCCCCGAGAACCACAGGTGTACACCCTGCCCCCATCCCGGGATGAGCTGACC
 K  G  Q  P  R  E  P  Q  V  Y  T  L  P  P  S  R  D  E  L  T
AAGAACCAGGTCAGCCTGACCTGCCTGGTCAAAGGCTTCTATCCCAGCGACATCGCCGTG
 K  N  Q  V  S  L  T  C  L  V  K  G  F  Y  P  S  D  I  A  V
GAGTGGGAGAGCAATGGGCAGCCGGAGAACAACTACAAGACCACGCCTCCCGTGCTGGAC
 E  W  E  S  N  G  Q  P  E  N  N  Y  K  T  T  P  P  V  L  D
TCCGACGGCTCCTTCTTCCTCTACAGCAAGCTCACCGTGGACAAGAGCAGGTGGCAGCAG
 S  D  G  S  F  F  L  Y  S  K  L  T  V  D  K  S  R  W  Q  Q
GGGAACGTCTTCTCATGCTCCGTGATGCATGAGGCTCTGCACAACCACTACACGCAGAAG
 G  N  V  F  S  C  S  V  M  H  E  A  L  H  N  H  Y  T  Q  K
AGCCTCTCCCTGTCTCCGGGTAAATGA
 S  L  S  L  S  P  G  K*
```

Fig. 49

SEQ ID NO:85 (nucleotide)   SEQ ID NO:86 (aminoacid)

```
ATGTTCTCACTAGCTCTTCTCCTCAGTCTTCTTCTCCTCTGTGTCTCTGATTCTAGGGCA
 M   F   S   L   A   L   LL  S   L   LLL C   V   S   D   S   R   A
GAAACAACTGTGACCCAGTCTCCAGCATCCCTGTCCATGGCTATAGGAGAAAAAGTCACC
 E   T   T   V   T   Q   S   P   A   S   L   S   M   A   I   G   E   K   V   T
ATCAGATGCATAACCAGCACTGATATTGATGATGATATGAACTGGTACCAGCAGAAGCCA
 I   R   C   I   T   S   T   D   I   D   DD  M   N   W   Y   Q   Q   K   P
GGGGAACCTCCTAAGCTCCTTATTTCAGAAGGCAATACTCTTCGTCCTGGAGTCCCATCC
 G   E   P   P   K   L   L   I   S   E   G   N   T   L   R   P   G   V   P   S
CGATTCTCCAGCAGTGGCTATGGTACAGATTTTGTTTTTACAATTGAAAACATGCTCTCA
 R   F   S   SS  G   Y   G   T   D   F   V   F   T   I   E   N   M   L   S
GAAGATGTTGCAGATTACTACTGTTTGCAAAGTGATAACTTGCCGTACACGTTCGGAGGG
 E   D   V   A   D   Y   Y   C   L   Q   S   D   N   L   P   Y   T   F   G   G
GGGACCAAGCTGGAAATCAAACGAACTGTGGCTGCACCATCTGTCTTCATCTTCCCGCCA
 G   T   K   L   E   I   K   R   T   V   A   A   P   S   V   F   I   F   P   P
TCTGATGAGCAGTTGAAATCTGGAACTGCCTCTGTTGTGTGCCTGCTGAATAACTTCTAT
 S   D   E   Q   L   K   S   G   T   A   S   V   V   C   L   L   N   N   F   Y
CCCAGAGAGGCCAAAGTACAGTGGAAGGTGGATAACGCCCTCCAATCGGGTAACTCCCAG
 P   R   E   A   K   V   Q   W   K   V   D   N   A   L   Q   S   G   N   S   Q
GAGAGTGTCACAGAGCAGGACAGCAAGGACAGCACCTACAGCCTCAGCAGCACCCTGACG
 E   S   V   T   E   Q   D   S   K   D   S   T   Y   S   L   S   S   T   L   T
CTGAGCAAAGCAGACTACGAGAAACACAAAGTCTACGCCTGCGAAGTCACCCATCAGGGC
 L   S   K   A   D   Y   E   K   H   K   V   Y   A   C   E   V   T   H   Q   G
CTGAGCTCGCCCGTCACAAAGAGCTTCAACAGGGGAGAGTGTTAG
 L   S   S   P   V   T   K   S   F   N   R   G   E   C   *
```

Fig. 50

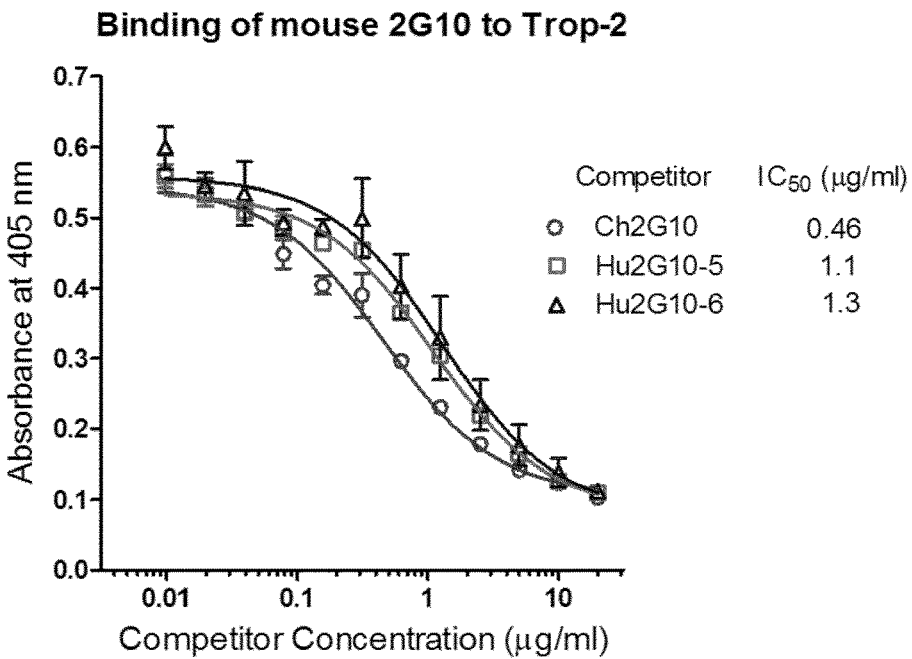

Fig. 51

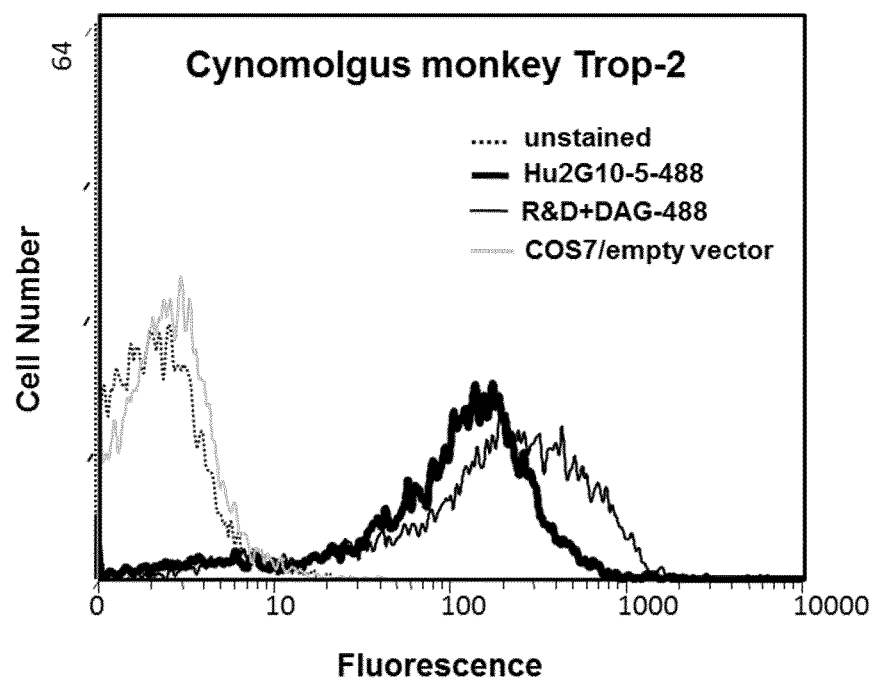
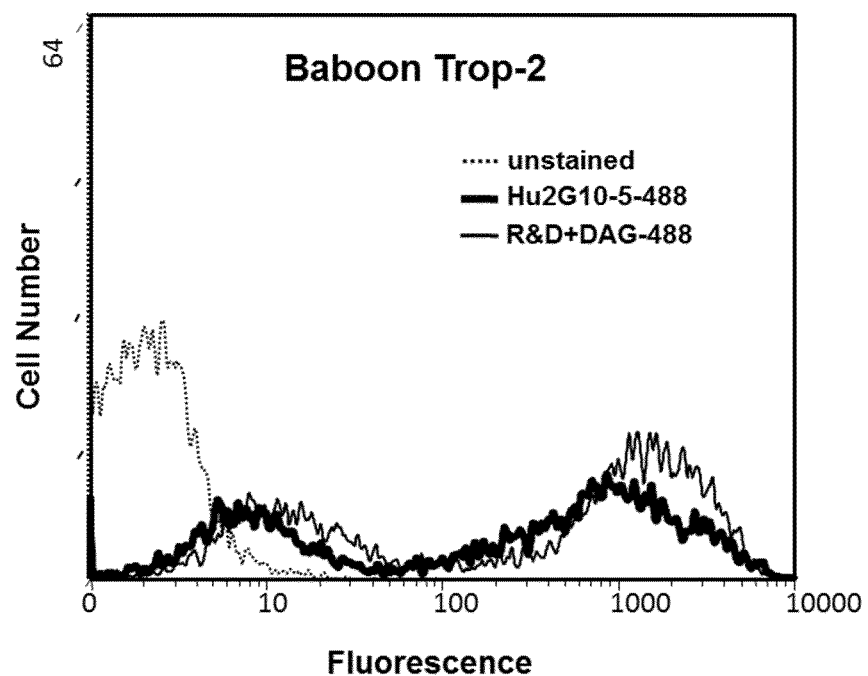
Fig. 55

HUMANIZED ANTI-TROP-2 MONOCLONAL ANTIBODIES AND USES THEREOF

CROSS-REFERENCE TO RELATED APPLICATIONS

This application is a 371 of PCT/EP2015/078672, filed Dec. 4, 2015, which claims the benefit of Italian Patent Application No. CH2014A000032 filed Dec. 4, 2014.

TECHNICAL FIELD

The present invention relates to humanized anti-Trop-2 monoclonal antibodies and their fragments, derivatives and conjugates. In particular the present invention relates to monoclonal antibodies comprising sequences of human and murine mixed origin, able to recognize and bind different regions of the Trop-2 molecule with high efficiency. Pharmaceutical compositions that contain such antibodies or their fragments, derivatives and conjugates are also objects of the present invention. The use of such antibodies and their fragments, derivatives and conjugates for diagnosis and therapy of human diseases, including cancer, is another object of the present invention.

STATE OF THE ART

Trop-2 (NCBI Accession number: P09758.3), also called tumor-associated calcium signal transducer 2 (TACSTD-2) (Calabrese, Crescenzi et al. 2001), is a type I transmembrane glycoprotein expressed on the surface of epithelial cells (Alberti, Miotti et al. 1992). The Trop-2 protein is organized into three domains: the extracellular domain, which consists of 248 amino acids (aa), with 12 cysteines involved in disulfide bridges and 4 N-glycosylation sites; the transmembrane domain of 23 aa, and the C terminal intracellular tail, which is 26 aa long. The extracellular domain of Trop-2 contains at the N-terminal a globular region (aa 31-145 in P09758.3) containing 12 cysteines, organized in an EGF-like domain followed by a thyroglobulin domain, and involved in cell-cell adhesion. The globular region is followed by a region without cysteine (aa 146-274 in P09758.3), which is thought to be a supporting stem connecting the extracellular domain to the transmembrane domain (Linnenbach, Seng et al. 1993; Fornaro, Dell'Arciprete et al. 1995).

In particular the amino acid sequence of human Trop-2 (NCBI Accession number: P09758.3) is:

and the amino acid sequences of said regions are:

```
Trop-2 globular region (EGF-like domain and
thyroglobulin domain; aa 31-145 of SEQ ID NO: 87):
QDNCTCPTNKMTVCSPDGPGGRCQCRALGSGMAVDCSTLTSKCLLLKARM
SAPKNARTLVRPSEHALVDNDGLYDPDCDPEGRFKARQCNQTSVCWCVNS
VGVRRTDKGDLSLRC Trop-2 stem region (aa 146-274 of SEQ ID NO: 87):
DELVRTHHILIDLRHRPTAGAFNHSDLDAELRRLFRERYRLHPKFVAAVH
YEQPTIQIELRQNTSQKAAGEVDIGDAAYYFERDIKGESLFQGRGGLDLR
VRGEPLQVERTLIYYLDEIPPKFSMKRLT
```

The intracellular tail contains a HIKE domain, which is able to bind phosphatidylinositol 4-5-bisphosphate (PIP2) (Ciccarelli, Acciarito et al. 2000), and includes a PKC phosphorylation site at serine 303 (Basu, Goldenberg et al. 1995).

Trop-2 is overexpressed in the vast majority of human carcinomas, both at the messenger RNA (mRNA) and at the protein levels (Ali, Aloisi et al. 2013). This overexpression is associated with increased aggressiveness and poor prognosis in cancers, including those of the pancreas (Bosco, Antonsen et al. 2011), stomach (Muhlmann, Spizzo et al. 2009), mouth (Fong, Moser et al. 2008), colorectum (Ohmachi, Tanaka et al. 2006; Fang, Lu et al. 2009), ovary (Bignotti, Todeschini et al. 2010), and lung (Jiange, Gao et al. 2013). Overexpression of Trop-2 in experimental tumors of various origin is capable of stimulating cell proliferation, both in vitro and in vivo, in proportion to the levels of expression. Similarly, inhibition of Trop-2 expression by means of specific silencing (si) RNA inhibits growth. Therefore Trop-2 is necessary and sufficient to induce the growth of cancer cells. This stimulation signal for tumor growth operates through the Trop-2-dependent activation of the Cyclin D1 and ERK/MEK signaling pathways and the activation of CREB1, Jun, NF-kB, Rb, STAT1 and STAT3 (Guerra, Trerotola et al. 2013).

No tumor-associated mutations have been found for Trop-2. Hence the overexpressed Trop-2 is a wild type (wt) molecule with respect to the sequence. However, the Authors of the present invention have recently demonstrated that tumors contain heterogeneous forms of Trop-2 with different localization, linked to different post-translational modifications (Ambrogi, Fornili et al. 2014). The Authors have also shown that different forms of Trop-2 have opposite prognostic impact. In breast cancer in particular membrane Trop-2 is an adverse prognostic factor, while cytoplasmic Trop-2 is associated with better prognosis (Ambrogi, Fornili et al. 2014). Heterogeneous glycosylation has been described also for the Trop-2 homolog Trop-1/EpCAM, with differential expression of more glycosylated forms in the tumor and surrounding tissues, compared to healthy tissues/distal sites (Pauli, Munz et al. 2003).

```
                                                        (SEQ ID NO: 87)
  1     margpglapp  plrlplllv   laavtghtaa  qdnctcptnk  mtvcspdgpg  grcqcralgs 61     gmavdcstlt  skclllkarm  sapknartlv  rpsehalvdn  dglydpdcdp  egrfkarqcn 121     qtsvcwcvns  vgvrrtdkgd  lslrcdelvr  thhilidlrh  rptagafnhs  dldaelrrlf 181     reryrlhpkf  vaavhyeqpt  iqielrqnts  qkaagdvdig  daayyferdi  kgeslfqgrg 241     gldlrvrgep  lqvertliyy  ldeippkfsm  krltagliav  ivvvvalva   gmavlvitnr 301     rksgkykkve  ikelgelrke  psl
```

The overexpression at the membrane level, the functional role in tumors and the negative predictive value make Trop-2 a valid target for anti-cancer immunotherapy.

The Authors of the present invention have developed murine anti-Trop-2 monoclonal antibodies that are homogeneous, with high affinity and specifically directed against different regions and different glycosylation states of the Trop-2 extracellular domain as described in WO2010089782 and (Ambrogi, Fornili et al. 2014). These antibodies, and in particular the 2EF antibody that is produced by the hybridoma deposited in the Advanced Biotechnology Center—ICLC of Genoa (Italy) with the number PD 08021, and the 2G10 antibody that is produced by the hybridoma deposited in the Advanced Biotechnology Center—ICLC of Genoa with the number PD 08020, are able to specifically and differentially recognize the globular region (aa 31-145 of SEQ ID NO:87; 2EF antibody) or the "stem" region (aa 146-274 of SEQ ID NO:87, 2G10 antibody) of Trop-2. Since they recognize distinct regions of Trop-2, these antibodies do not compete for the binding to the target, with an increase in the number of molecules of antibody that can bind to the tumor cell. The 2EF antibody also selectively binds to specific forms of post-translational modifications of the target, potentially associated with more aggressive tumors (Ambrogi, Fornili et al. 2014). These antibodies have high in vivoantitumor activity, as measured on human cancer cells transplanted into immunodeficient mice, and this activity synergistically increases in the case of co-administration of the two antibodies. Therefore the 2EF and 2G10 antibodies have specific characteristics for combined anti-cancer therapeutic use that make them better than any other anti-Trop-2 that have been described so far ((Fradet, Cordon-Cardo et al. 1984); WO2003074566, US2004001825, US2007212350, US2008131363; WO2008144891; US2012237518; CN102827282; WO2011145744; WO2013068946).

Murine monoclonal antibodies have a number of limitations for their use in man, which make them ill-suited for therapeutic use. Murine IgG have a plasma half-life that is much shorter (a few hours) than that of antibodies of human origin (about three weeks). The murine origin of the molecule is recognized by the human immune system, triggering an immune response characterized by the production of human anti-mouse antibodies (human anti-mouse antibodies (HAMA)). HAMAs inactivate and eliminate mouse antibodies after the first administration. Moreover, the formation of complexes between mouse antibodies and HAMA may cause serious allergic reactions, even up to anaphylactic shock. For this reason murine antibodies cannot be used for repeated administration in the course of the therapy. In addition, due to differences between the human and the mouse immune system, the murine Fc portion has a reduced ability to activate the complement and stimulate the antibody-dependent cellular cytotoxicity (ADCC) of the immune system, thus limiting therapeutic use (Khazaeli, Conry et al. 1994).

This limitation to therapeutic use in man of monoclonal antibodies of murine origin can be overcome through the humanization process, in which there is the replacement of part of the sequences of murine origin of the antibody with sequences of human origin, while retaining the aminoacid residues of the original antibody that are important for the formation of the surface that contacts the antigen. Different levels of humanization can be implemented by applying recombinant DNA techniques. A first level of humanization is the fusion of murine variable regions and human constant regions (Morrison, Johnson et al. 1984). The resulting chimeric antibodies retain about 33% of the murine protein, and are able to stimulate human effector-mediated cytotoxicity (Liu, Robinson et al. 1987). Again, however, there may be a human immune response against the murine peptide sequence of the chimeric antibody, with the production of human anti-chimeric antibodies (HACA) (Afif, Loftus et al. 2010). This problem is overcome with the creation of humanized antibodies, in which the complementarity determining regions (CDR) of the variable regions of the murine antibody (typically 5-10% of the molecule) are "transplanted" onto sequences of human origin that form the framework of the antibody.

These successive stages of engineering progressively lower the likelihood of adverse reactions in man, but can drastically affect the antibody characteristics. For example there may be problems of instability of the cDNA that codes for the recombinant antibody, when the new combination of nucleotide sequences creates new regulatory sequences or activate cryptic regulatory sequences, for example splicing signals. Another problem that is often encountered is chemical instability, for example loss of solubility of the antibody, resulting in immunoglobulin precipitation in the course of the purification process or after administration to the patient. Moreover with the humanization process there is normally a drop of affinity of the antibody to the target, which can be several orders of magnitude lower, with negative impact on the therapeutic efficacy of the antibody itself. This is due to the introduction of the human framework, that during the three-dimensional folding of the molecule modifies the formation and presentation of the contact surface between antibody and antigen by the murine CDRs. To overcome this problem, it is necessary to change the framework sequence, trying to find among the many billions of possible combinations those that have the greatest impact on the affinity of the antibody towards the target.

SUMMARY OF THE INVENTION

In order to overcome the therapeutic limitations of murine monoclonal antibodies the Authors of the present invention have developed humanized anti-Trop-2monoclonal antibodies that are able to recognize and bind with high efficiency different regions and different post-translational modification states of the Trop- 2 molecule.

This was achieved through successive rounds of engineering/optimization consisting in introducing targeted changes in the mouse 2G10 and 2EF antibodies, such changes not being predictable just on the basis of the techniques known in the art. For this purpose the chimeric CH-2EF and CH-2G10 antibodies were built first, followed by the early humanized versions: Hu-2EF-4, Hu-2EF-5, Hu-2G10-1, Hu-2G10-2, Hu-2G10-3 and Hu-2G10-4. These antibodies, however, showed negative characteristics: chemical instability, with formation of aggregates and loss of solubility (for the CH-2EF antibody), and loss of affinity for Trop-2 in all of these first humanized versions. In order to recover the affinity for Trop-2 other, new, amino acid residues were then replaced in the human framework, said amino acids being identified through non-canonical predictions of structure and three-dimensional folding of the antibody molecule, and without any need to resort to the creation and analysis of combinatorial libraries with billions of different sequences. This allowed the authors to obtain humanized monoclonal antibodies with high affinity, including Hu-2EF-7, Hu-2G10-5 and Hu-2G10-6, which are not recognized by anti-mouse antibodies, specifically directed against distinct regions and various forms of post-translational modification of the extracellular domain of Trop-2, such antibodies to be used alone or together as a combination, in diagnostic and human therapy, in particular in vivo diagnosis and prevention and treatment of Trop-2-expressing tumors and metastases.

DESCRIPTION OF THE INVENTION

The present invention refers to humanized anti-Trop-2 monoclonal antibodies, their fragments, derivatives and conjugates, that are able to recognize and bind with high efficiency distinct regions or specific forms of post-translational modification of Trop-2, such antibodies obtained from the 2EF and 2G10 monoclonal antibodies.

The antibodies according to the present invention are characterized in that they preferably comprise a combination of human and murine sequences, where the sequences of murine origin include, in the variable regions of the heavy chain (VH) and light chain (VL), one, two or all three the CDR selected from the group containing the following amino acid sequences: VH-CDR1: NYWIG (SEQ ID NO: 1), VH-CDR2: DIYPGGGYTNYNEKFKG (SEQ ID NO: 2), VH-CDR3: GTGGGDY (SEQ ID NO: 3) (heavy chain) and VL-CDR1: RASQSVSTSSYSYMH (SEQ ID NO: 4), VL-CDR2 YASNLES (SEQ ID NO: 5), VL-CDR3 QHSWEIPYT (SEQ ID NO: 6) (light chain); or from the group containing: VH-CDR1: SSYIS (SEQ ID NO: 7), VH-CDR2: WIYAGTGGTSYNQKFTG (SEQ ID NO: 8), VH-CDR3: HNPRYYAMDY (SEQ ID NO: 9) (heavy chain) and VL-CDR1: ITSTDIDDDMN (SEQ ID NO: 10), VL-CDR2: EGNTLRP (SEQ ID NO: 11), VL-CDR3: LQSDNLPYT (SEQ ID NO: 12) (light chain).

It is therefore an object of the invention a humanized antibody, or fragments, derivatives or conjugates thereof, which recognises and binds the same epitopes or epitope as the antibody 2EF produced by the hybridoma deposited in the Advanced Biotechnology Center (ABC) with the number PD 08021 or as the antibody 2G10 produced by the hybridoma deposited in the Advanced Biotechnology Center (ABC) with the number PD 08020.

The antibodies according to the invention are anti-Trop-2 antibodies.

In an aspect of the invention, said humanized antibody, or fragments, derivatives or conjugates thereof comprises a variable domain framework region from at least one heavy chain of a human antibody or from at least one human consensus framework and/or a variable domain framework region from at least one light chain of a human antibody or from at least one human consensus framework.

The term "from" as above used may be intended as the variable domain framework region derives from a human antibody or from a human consensus framework.

Preferably, said heavy chain of a human antibody or human consensus framework is at least 50% homologous to the heavy chain of said antibody 2EF or of said antibody 2G10 and/or said light chain of a human antibody or human consensus framework is at least 50% homologous to the light chain of said antibody 2EF or of said antibody 2G10.

More preferably, the mature form of said heavy chain of a human antibody or human consensus framework is at least 50% homologous at the aminoacid level to the mature form of the heavy chain of said antibody 2EF or of said antibody 2G10 and/or the mature form of said light chain of a human antibody or human consensus framework is at least 50% homologous at the aminoacid level to the mature form of the light chain of said antibody 2EF or of said antibody 2G10.

In a preferred embodiment of the invention, the humanized antibody, or fragments, derivatives or conjugates thereof comprises at least one of the heavy chain complementary determining region (CDRH) amino acid sequence of said antibody 2EF or of said antibody 2G10 and/or at least one of the light chain complementary determining region (CDRL) amino acid sequence of said antibody 2EF or of said antibody 2G10.

Preferably, in said variable domain framework region at least one amino acid is substituted with the corresponding residue from a heavy chain of a mouse antibody or mouse consensus framework and/or from a light chain of a mouse antibody or mouse consensus framework, or fragments, derivatives or conjugates thereof.

Preferably, said mouse antibody is the antibody 2EF or the antibody 2G10 as above defined and/or the mouse consensus framework derives from the antibody 2EF or the antibody 2G10 as above defined.

In a further preferred embodiment, the framework of the heavy chain variable region has at least 50% identity to the framework of SEQ ID NO: 88 or SEQ ID NO:89; and the framework of the light chain variable region has at least 50% identity to the framework of SEQ ID NO: 91.

In a further preferred embodiment, the framework of the heavy chain variable region has at least 50% identity to the framework of SEQ ID NO: 90; and the framework of the light chain variable region has at least 50% identity to the framework of SEQ ID NO: 92.

In a preferred aspect of the invention, the amino acidic substitutions are in position 11 and/or 38 and/or 40 and/or 43 and/or 44 and/or 48 and/or 68 and/or 70 and/or 72, preferably in positions 38, 44, 48, 68, 70 and 72, of the mature heavy chain of the human antibody, more preferably said mature heavy chain having the sequence of SEQ ID NO:88, or preferably in positions 48, 68, 70 and 72 of the mature heavy chain of the human antibody, more preferably said mature heavy chain having the sequence of SEQ ID NO:89.

In a preferred embodiment, said mature heavy chain has the of SEQ ID NO: 93 or 94.

Preferably, the above substitutions are as follows:
Hu2EF VH4:
 G (murine) instead of R (human) at position 44
 I (murine) instead of M (human) at position 48
 A (murine) instead of V (human) at position 68
 L (murine) instead of I (human) at position 70
 A (murine) instead of R (human) at position 72;
Hu2EF VH5 (different human IgG as acceptor VH):
 I (murine) instead of M (human) at position 48
 A (murine) instead of V (human) at position 68
 L (murine) instead of M (human) at position 70
 A (murine) instead of R (human) at position 72;
Hu2EF VH4 R38K variant, chosen for the final humanized antibody=VH7:
 K (murine) instead of R (human) at position 38
 G (murine) instead of R (human) at position 44
 I (murine) instead of M (human) at position 48
 A (murine) instead of V (human) at position 68
 L (murine) instead of I (human) at position 70
 A (murine) instead of R (human) at position 72;
Hu2EF VH4 V11L variant:
 L (murine) instead of V (human) at position 11
 G (murine) instead of R (human) at position 44
 I (murine) instead of M (human) at position 48
 A (murine) instead of V (human) at position 68
 L (murine) instead of I (human) at position 70
 A (murine) instead of R (human) at position 72;

Hu2EF VH4 A4OR variant:
R (murine) instead of A (human) at position 40
G (murine) instead of R (human) at position 44
I (murine) instead of M (human) at position 48
A (murine) instead of V (human) at position 68
L (murine) instead of I (human) at position 70
A (murine) instead of R (human) at position 72;
Hu2EF VH4 Q43H variant:
H (murine) instead of Q (human) at position 43
G (murine) instead of R (human) at position 44
I (murine) instead of M (human) at position 48
A (murine) instead of V (human) at position 68
L (murine) instead of I (human) at position 70
A (murine) instead of R (human) at position 72.

In a further preferred aspect of the invention, the amino acidic substitutions are in positions 27 and/or 30 and/or 37 and/or 48 and/or 49 and/or 67 and/or 68 and/or 70 and/or 72, preferably in positions 27, 30, 37, 48, 49, 67, 68, 70 and 72, or in positions 27, 30, 37, 48, 49, 70 and 72, of the mature heavy chain of the human antibody, preferably said mature heavy chain having the sequence of SEQ ID NO:90.

In a preferred embodiment, said mature heavy chain has the sequence of SEQ ID NO: 95.

Preferably, the above substitutions are as follows:
Hu2G10 VH1:
F (murine) instead of Y (human) at position 27
S (murine) instead of T (human) at position 30
L (murine) instead of V (human) at position 37
I (murine) instead of M (human) at position 48
A (murine) instead of G (human) at position 49
K (murine) instead of R (human) at position 67
A (murine) instead of V (human) at position 68
L (murine) instead of I (human) at position 70
L (murine) instead of R (human) at position 72;
Hu2G10 VH2:
F (murine) instead of Y (human) at position 27
S (murine) instead of T (human) at position 30
L (murine) instead of V (human) at position 37
I (murine) instead of M (human) at position 48
A (murine) instead of G (human) at position 49
L (murine) instead of I (human) at position 70
V (murine) instead of R (human) at position 72.

Preferably, the amino acidic substitutions are in positions 4 and/or 53 and/or 104, preferably in positions 4, 53, and 104, of the mature light chain, preferably said mature light chain of the human antibody having the sequence of SEQ ID NO:91.

In a preferred embodiment, said mature light chain has the sequence of SEQ ID NO: 96.

Preferably, the above substitutions are as follows:
Hu2EF VL1:
K (murine) instead of Y (human) at position 53;
Hu2EF VL2 chosen for the final humanized antibody:
L (murine) instead of M (human) at position 4
K (murine) instead of Y (human) at position 53
G (murine) instead of Q (human) at position 104.

In another preferred embodiment, the amino acidic substitution is in position 2 and/or 22 and/or 42 and/or 49 and/or 64 and/or 67 and/or 72 and/or 85, preferably in positions 2, 49 and 67, of the mature light chain of the human antibody, preferably said mature light chain having the sequence of SEQ ID NO:92.

In a preferred embodiment, said mature light chain has the sequence of SEQ ID NO: 97.

Preferably, the above substitutions are as follows:
Hu2G10 VL1:
S (murine) instead of Y (human) at position 49
Y (murine) instead of S (human) at position 67;
Hu2G10 VL2:
S (murine) instead of Y (human) at position 49;
Hu2G10 VL3 (VL1 I2T variant):
T (murine) instead of I (human) at position 2
S (murine) instead of Y (human) at position 49
Y (murine) instead of S (human) at position 67;
Hu2G10 VL1 T22R variant
R (murine) instead of T (human) at position 22
S (murine) instead of Y (human) at position 49
Y (murine) instead of S (human) at position 67;
Hu2G10 VL1 K42E variant
E (murine) instead of K (human) at position 42
S (murine) instead of Y (human) at position 49
Y (murine) instead of S (human) at position 67;
Hu2G10 VL1 G64S variant
S (murine) instead of Y (human) at position 49
S (murine) instead of G (human) at position 64
Y (murine) instead of S (human) at position 67;
Hu2G10 VL1 T72V variant
S (murine) instead of Y (human) at position 49
Y (murine) instead of S (human) at position 67
V (murine) instead of T (human) at position 72;
Hu2G10 VL1 T85D variant
S (murine) instead of Y (human) at position 49
Y (murine) instead of S (human) at position 67
D (murine) instead of T (human) at position 85.

Preferably, the humanized antibody, or fragments, derivatives or conjugates thereof as above defined comprises:
a heavy chain complementary determining region (CDRH3) amino acid sequence having at least 80% identity to the amino acid sequence of SEQ ID NO:3 or SEQ ID NO:9 and/or
a heavy chain complementary determining region (CDRH2) amino acid sequence having at least 80% identity to the amino acid sequence of SEQ ID NO:2 or SEQ ID NO:8 and/or
a heavy chain complementary determining region (CDRH1) amino acid sequence having at least 80% identity to the amino acid sequence of SEQ ID NO:1 or SEQ ID NO:7.

More preferably, the humanized antibody, or fragments, derivatives or conjugates thereof as above defined comprises:
a heavy chain complementary determining region (CDRH3) amino acid sequence having at least 80% identity to the amino acid sequence of SEQ ID NO:3 and/or
a heavy chain complementary determining region (CDRH2) amino acid sequence having at least 80% identity to the amino acid sequence of SEQ ID NO:2 and/or
a heavy chain complementary determining region (CDRH1) amino acid sequence having at least 80% identity to the amino acid sequence of SEQ ID NO:1.

More preferably, the humanized antibody, or fragments, derivatives or conjugates thereof as above defined comprises:
a heavy chain complementary determining region (CDRH3) amino acid sequence having at least 80% identity to the amino acid sequence of SEQ ID NO:9 and/or
a heavy chain complementary determining region (CDRH2) amino acid sequence having at least 80% identity to the amino acid sequence of SEQ ID NO:8 and/or a heavy chain complementary determining region (CDRH1) amino acid sequence having at least 80% identity to the amino acid sequence of SEQ ID NO:7.

In a preferred embodiment, the humanized antibody or fragments, derivatives or conjugates thereof as above defined comprises:
- a light chain complementary determining region (CDRL3) amino acid sequence having at least 80% identity to the amino acid sequence of SEQ ID NO:6 or 12 and/or
- a light chain complementary determining region (CDRL2) amino acid sequence having at least 80% identity to the amino acid sequence of SEQ ID NO:5 or 11 and/or
- a light chain complementary determining region (CDRL1) amino acid sequence having at least 80% identity to the amino acid sequence of SEQ ID NO:4 or 10.

More preferably, the humanized antibody or fragments, derivatives or conjugates thereof as above defined comprises:
- a light chain complementary determining region (CDRL3) amino acid sequence having at least 80% identity to the amino acid sequence of SEQ ID NO:6 and/or
- a light chain complementary determining region (CDRL2) amino acid sequence having at least 80% identity to the amino acid sequence of SEQ ID NO:5 and/or
- a light chain complementary determining region (CDRL1) amino acid sequence having at least 80% identity to the amino acid sequence of SEQ ID NO:4.

More preferably, the humanized antibody or fragments, derivatives or conjugates thereof as above defined comprises:
- a light chain complementary determining region (CDRL3) amino acid sequence having at least 80% identity to the amino acid sequence of SEQ ID NO: 12 and/or
- a light chain complementary determining region (CDRL2) amino acid sequence having at least 80% identity to the amino acid sequence of SEQ ID NO: 11 and/or
- a light chain complementary determining region (CDRL1) amino acid sequence having at least 80% identity to the amino acid sequence of SEQ ID NO: 10.

Preferably, the humanized antibody or fragments, derivatives or conjugates thereof as above defined comprise a heavy chain complementary determining regions (CDRH1) amino acid sequence having at least 80% identity to an amino acid sequence of SEQ ID NO: 1 and a heavy chain complementary determining regions (CDRH2) amino acid sequence having at least 80% identity to an amino acid sequence of SEQ ID NO: 2 and a heavy chain complementary determining regions (CDRH3) amino acid sequence having at least 80% identity to an amino acid sequence of SEQ ID NO: 3.

Preferably, the humanized antibody or fragments, derivatives or conjugates thereof as above defined comprises a heavy chain complementary determining regions (CDRH1) amino acid sequence having at least 80% identity to an amino acid sequence of SEQ ID NO: 7 and a heavy chain complementary determining regions (CDRH2) amino acid sequence having at least 80% identity to an amino acid sequence of SEQ ID NO: 8 and a heavy chain complementary determining regions (CDRH3) amino acid sequence having at least 80% identity to an amino acid sequence of SEQ ID NO: 9.

In a preferred embodiment, the humanized antibody or fragments, derivatives or conjugates thereof as above defined further comprises a light chain complementary determining regions (CDRL1) amino acid sequence having at least 80% identity to an amino acid sequence of SEQ ID NO: 4 and a light chain complementary determining regions (CDRL2) amino acid sequence having at least 80% identity to an amino acid of SEQ ID NO: 5 and a light chain complementary determining regions (CDRL3) amino acid sequence having at least 80% identity to an amino acid sequence of SEQ ID NO:6.

In a preferred embodiment, the humanized antibody or fragments, derivatives or conjugates thereof as above defined further comprises a light chain complementary determining regions (CDRL1) amino acid sequence having at least 80% identity to an amino acid sequence of SEQ ID NO: 10 and a light chain complementary determining regions (CDRL2) amino acid sequence having at least 80% identity to an amino acid of SEQ ID NO: 11 and a light chain complementary determining regions (CDRL3) amino acid sequence having at least 80% identity to an amino acid sequence of SEQ ID NO:12.

In an even preferred embodiment of the invention, the humanized antibody, or fragments, derivatives or conjugates thereof as above defined comprises:
a heavy chain complementary determining region (CDRH3) amino acid sequence having at least 80% identity to the amino acid sequence of SEQ ID NO:9 and at least one of the complementary determining region selected from the group consisting of:
a heavy chain complementary determining region (CDRH2) amino acid sequence having at least 80% identity to the amino acid sequence of SEQ ID NO:8,
a heavy chain complementary determining region (CDRH1) amino acid sequence having at least 80% identity to the amino acid sequence of SEQ ID NO:7,
a light chain complementary determining region (CDRL3) amino acid sequence having at least 80% identity to the amino acid sequence of SEQ ID NO: 12,
a light chain complementary determining region (CDRL2) amino acid sequence having at least 80% identity to the amino acid sequence of SEQ ID NO: 11, and
a light chain complementary determining region (CDRL1) amino acid sequence having at least 80% identity to the amino acid sequence of SEQ ID NO:10.

In another preferred embodiment of the invention, the humanized antibody, or fragments, derivatives or conjugates thereof as above defined comprises:
a heavy chain complementary determining region (CDRH3) amino acid sequence having at least 80% identity to the amino acid sequence of SEQ ID NO:3 and at least one of the complementary determining region selected from the group consisting of:
a heavy chain complementary determining region (CDRH2) amino acid sequence having at least 80% identity to the amino acid sequence of SEQ ID NO:2,
a heavy chain complementary determining region (CDRH1) amino acid sequence having at least 80% identity to the amino acid sequence of SEQ ID NO:1,
a light chain complementary determining region (CDRL3) amino acid sequence having at least 80% identity to the amino acid sequence of SEQ ID NO: 6, a light chain complementary determining region (CDRL2) amino acid sequence having at least 80% identity to the amino acid sequence of SEQ ID NO: 5, and
a light chain complementary determining region (CDRL1) amino acid sequence having at least 80% identity to the amino acid sequence of SEQ ID NO:4.

In a yet preferred embodiment, the humanized antibody or fragments, derivatives or conjugates thereof as above defined comprises a CDRH1 amino acid sequence having at least 80% identity to SEQ ID No. 1, a CDRH2 amino acid sequence having at least 80% identity to SEQ ID No. 2, a CDRH3 amino acid sequence having at least 80% identity to SEQ ID No. 3, a CDRL1 amino acid sequence having at least 80% identity to SEQ ID No. 4, a CDRL2 amino acid sequence having at least 80% identity to SEQ ID No. 5 and a CDRL3 amino acid sequence having at least 80% identity to SEQ ID No. 6.

In another preferred embodiment, the humanized antibody or fragments, derivatives or conjugates thereof as above defined comprises a CDRH1 amino acid sequence having at least 80% identity to SEQ ID No. 7, a CDRH2 amino acid sequence having at least 80% identity to SEQ ID No. 8, a CDRH3 amino acid sequence having at least 80% identity to SEQ ID No. 9, a CDRL1 amino acid sequence having at least 80% identity to SEQ ID No. 10, a CDRL2 amino acid sequence having at least 80% identity to SEQ ID No. 11 and a CDRL3 amino acid sequence having at least 80% identity to SEQ ID No. 12.

Preferably, the humanized antibody, or fragments, derivatives or conjugates thereof according to the invention comprises a heavy chain variable region amino acid sequence having at least 80% identity to the amino acid sequence selected from the group consisting of SEQ ID NOs: 14, 22, 24, 26, 18, 32, or 34 or fragments thereof and/or a light chain variable region amino acid sequence having at least 80% identity to the amino acid sequence selected from the group consisting of SEQ ID NOs: 16, 28, 30, 20, 36, 38 or 40 or fragments thereof.

The fragment of the amino acid sequence SEQ ID NOs: 14, 22, 24 or 26 may the fragment aa. 20-135 of said sequences.

The fragment of the amino acid sequence SEQ ID NOs: 18, 32 or 34 may the fragment aa. 20-138 of said sequences.

The fragment of the amino acid sequence SEQ ID NOs: 20, 36, 38 or 40 may the fragment aa. 21-127 of said sequences.

The fragment of the amino acid sequence SEQ ID NOs: 16, 28 or 30 may the fragment aa. 21-131 of said sequences.

Preferably, the humanized antibody, or fragments, derivatives or conjugates thereof according to the invention comprises a heavy chain variable region amino acid sequence having at least 80% identity to the following amino acid sequence and a light chain variable region amino acid sequence having at least 80% identity to the following amino acid sequence according to the following combinations:
SEQ ID NOs: 14 and 16,
SEQ ID Nos: 14 and 28,
SEQ ID Nos: 14 and 30,
SEQ ID NOs: 22 and 16,
SEQ ID Nos: 22 and 28,
SEQ ID Nos: 22 and 30,
SEQ ID NOs: 24 and 16,
SEQ ID Nos: 24 and 28,
SEQ ID Nos: 24 and 30,
SEQ ID NOs: 26 and 16,
SEQ ID Nos: 26 and 28,
SEQ ID Nos: 26 and 30,
SEQ ID NOs: 18 and 20,
SEQ ID Nos: 18 and 36,
SEQ ID Nos: 18 and 38,
SEQ ID Nos: 18 and 40,
SEQ ID NOs: 32 and 20,
SEQ ID Nos: 32 and 36,
SEQ ID Nos: 32 and 38,
SEQ ID Nos: 32 and 40,
SEQ ID NOs: 34 and 20,
SEQ ID Nos: 34 and 36,
SEQ ID Nos: 34 and 38,
SEQ ID Nos: 34 and 40.

The humanized antibody or fragments, derivatives or conjugates thereof according to the invention preferably comprises a heavy chain variable region amino acid sequence having at least 80% identity to the amino acid sequence comprising the SEQ ID NO:26 and a light chain variable region amino acid sequence having at least 80% identity to the amino acid sequence comprising the SEQ ID NO:30. Preferably, the humanized antibody or fragments, derivatives or conjugates thereof according to the invention preferably comprises a heavy chain variable region amino acid sequence comprising the SEQ ID NO:26 and a light chain variable region amino acid sequence comprising the SEQ ID NO:30.

The humanized antibody or fragments, derivatives or conjugates thereof according to the invention preferably comprises a heavy chain variable region amino acid sequence having at least 80% identity to the amino acid sequence comprising the SEQ ID NO:32 or 34 and a light chain variable region amino acid sequence having at least 80% identity to the amino acid sequence comprising the SEQ ID NO:40. Preferably, the humanized antibody or fragments, derivatives or conjugates thereof of the invention preferably comprises a heavy chain variable region amino acid sequence comprising the SEQ ID NO:32 or the SEQ ID NO:34 and a light chain variable region amino acid sequence comprising the SEQ ID NO:40.

Preferably, the humanized antibody or fragments, derivatives or conjugates thereof as above defined is of the IgG1 isotype.

A further object of the invention is a nucleic acid molecule encoding a humanized antibody or fragments, derivatives or conjugates thereof as above defined, or hybridizing with said nucleic acid, or a degenerate sequence thereof.

Preferably, said nucleic acid molecule comprises at least one nucleic acid sequence selected from the group consisting of SEQ ID NO:13,15,17,19,21,23,25,27,29,31,33,35,37, 39,41,43,45,47,49.

Another object of the invention is an expression vector comprising the nucleic acid as above defined or encoding for the humanized antibody or fragments, derivatives or conjugates thereof as above defined.

Further objects of the invention are a host cell that produces a humanized antibody or fragments, derivatives or conjugates thereof as above defined, a combination comprising or consisting of at least one of the humanized antibodies, or fragments, derivatives or conjugates thereof, or combination thereof as above defined, preferably said combination comprises or consists of at least one antibody which recognises and binds the same epitopes or epitope as the antibody 2EF as above defined and one antibody which recognises and binds the same epitopes or epitope as the antibody 2G10 as above defined, or fragments, derivatives or conjugates thereof. More preferably said combination comprises Hu-2EF-7 and Hu-2G10-5 or Hu-2EF-7 and Hu-2G10-6.

Another object of the invention is a pharmaceutical composition that comprises at least one humanized antibody or fragment or derivative or conjugate thereof as above defined or the combination according to the invention and at least one excipients and/or adjuvants and/or carriers and/or diluents that are pharmaceutically acceptable.

A further object of the invention is the humanized antibody or fragment or derivative or conjugate thereof or the combination, or the pharmaceutical composition as above defined for use as a medicament, preferably for use in the prevention and/or treatment of tumors and metastases, more preferably of the tumors and metastases that express Trop-2.

In the context of the present invention, the tumors include: endometrium, breast, head and neck, thyroid, colorectal, stomach, lung, ovary, prostate, pancreas, cervix, kidney and bladder (urothelial) tumors.

In a preferred embodiment, the humanized antibody or fragment or derivative or conjugate thereof, or the combination, or the pharmaceutical composition are in combination with at least one therapeutic agent.

Another object of the invention is an in vitro or ex-vivo method for diagnosing and/or assessing the risk of developing and/or prognosing and/or for monitoring the progression and/or for monitoring the efficacy of a therapeutic treatment and/or for the screening of a therapeutic treatment of a tumor or metastasis in a subject comprising the steps of:
a) detecting Trop-2 expressing cells in a sample isolated from the subject with the humanized anti-Trop-2 monoclonal antibody or fragment or derivative or conjugate thereof according to the invention or the combination according to the invention,
b) comparing with respect to a proper control and/or reference.

Another object of the invention is the humanized antibody or fragment or derivative or conjugate or the combination thereof according to the invention, for use in a method for diagnosing and/or assessing the risk of developing and/or prognosing and/or for monitoring the progression and/or for monitoring the efficacy of a therapeutic treatment and/or for the screening of a therapeutic treatment of a tumor or metastasis.

A further object of the invention is a kit comprising at least one humanized antibody or fragment or derivative or conjugate thereof according to the invention, or the combination according to the invention and optionally detecting means, wherein said kit is preferably for the diagnosis of tumors and metastases.

The hybridoma that produces the antibody 2EF was deposited under the Budapest Treaty at the Advanced Biotechnology Center (ABC), Interlab Cell Line Collection, with number PD08021 on Aug. 27, 2008 (deposit information:
Microorganism Deposit Accession No. PD08021;
Depositary Institution name: Advanced Biotechnology Center (ABC) ("Centro di Bitoecnologie Avanzate (CBA)");
Depositary Institution address: Interlab Cell Line Collection (Biotechnology Dept); Largo Rossana Benzi, 10, 16132 Genova, Italy;
Deposit Date: Aug. 27, 2008).

The hybridoma that produces the antibody 2G10 was deposited under the Budapest Treaty at the Advanced Biotechnology Center (ABC), Interlab Cell Line Collection, with number PD08020 on Aug. 27, 2008 (deposit information:
Microorganism Deposit Accession No.: PD08020;
Depositary Institution name: Advanced Biotechnology Center (ABC) ("Centro di Bitoecnologie Avanzate (CBA)");
Depositary Institution address: Interlab Cell Line Collection (Biotechnology Dept); Largo Rossana Benzi, 10, 16132 Genova, Italy;
Deposit Date: Aug. 27, 2008).

The invention also includes mutants of the described CDR in order to modulate affinity or binding specificity.

The present invention also provides humanized anti-Trop-2 monoclonal antibodies, or derivatives thereof, with high affinity and directed against distinct portions or specific forms of post-translational modification of the target, such antibodies comprising heavy chain and light chain variable regions as above defined, combined with sequences of human immunoglobulins (IgM, IgD, IgG, IgA, IgE) coding for peptides that do not induce immune response in human.

In a preferred aspect of the invention the variable regions of the heavy chain of SEQ ID NO: 14 (or its encoding nucleic acid SEQ ID NO: 13), (FIG. 1) and light chain of SEQ ID NO: 16 (or its encoding nucleic acid of SEQ ID NO: 15) (FIG. 2) have been joined to a gamma-1 (G1) heavy chain constant region and a kappa (κ) light chain constant region, respectively, of human immunoglobulins (Ig), for the production of the chimeric antibody Ch2EF-IgG1/κ, which is herein defined Ch2EF. In another aspect of the invention the variable regions of the heavy chain of SEQ ID NO: 18 (or its encoding nucleic acid of SEQ ID NO: 17) (FIG. 3) and light chain of SEQ ID NO: 20 (or its encoding nucleic acid of SEQ ID NO: 19) (FIG. 4) have been combined with a G1 heavy chain constant region and a κ light chain constant region, respectively, of human Ig, for the production of chimeric antibody Ch2G10-IgG1/k, which is herein defined Ch2G10.

Preferably, the antibodies of the invention are humanized Hu2EF antibodies having a VH region comprising a sequence selected from the group consisting of: SEQ ID NO: 22; SEQ ID NO 24; SEQ ID NO: 26 (or encoded by the nucleotide sequence selected from the group consisting of: SEQ ID NO: 21, SEQ ID NO: 23, SEQ ID NO: 25) (FIGS-7) together with a VL region comprising a sequence selected from the group consisting of: SEQ ID NO: 28; SEQ ID NO: 30 (or encoded by the nucleotide sequence selected from the group consisting of: SEQ ID NO: 27 and SEQ ID NO: 29) (FIG. 8-9), and humanized Hu2G10 antibodies having a VH region comprising a sequence selected from the group consisting of: SEQ ID NO: 32; SEQ ID NO: 34 (or encoded by the nucleotide sequence selected from the group consisting of: SEQ ID NO: 31, SEQ ID NO: 33) (FIG. 10-11) together with a VL region comprising a sequence (or encoded by the nucleotide sequence) selected from the group consisting of: SEQ ID NO: 36, SEQ ID NO: 38, SEQ ID NO: 40 (or encoded by the nucleotide sequence selected from the group consisting of: SEQ ID NO: 35, SEQ ID NO: 37, SEQ ID NO: 39) (FIG. 12-14).

For sake of brevity, the preferred antibody according to the present invention shall be identified with the name Hu2EF-7 (comprising SEQ ID No. 26 and SEQ ID No. 30), Hu2G10-5 (comprising SEQ ID No. 32 and SEQ ID No. 40) and Hu2G10-6 (comprising SEQ ID No. 34 and SEQ ID No. 40). While the present invention focuses on such antibodies, as an exemplification of the present invention, one of ordinary skill in the art will appreciate that, once given the present disclosure, other similar antibodies, and antibody fragments thereof, as well as antibody fragments of these similar antibodies may be produced and used within the scope of the present invention. Such similar antibodies may be produced by a reasonable amount of experimentation by those skilled in the art.

Still preferably, the antibody is a scFv, Fv fragment, a Fab fragment, a F(ab)2 fragment, a multimeric antibody, a peptide or a proteolytic fragment containing the epitope binding region.

The antibodies, or fragment or derivative or conjugate thereof according to the invention preferably comprises a G1 heavy chain comprising a sequence selected from the group consisting of SEQ ID NO: 42, SEQ ID NO: 46 and SEQ ID NO: 50.

The antibodies, or fragment or derivative or conjugate thereof according to the invention preferably comprises the κ light chain comprising a sequence selected from the group consisting of SEQ ID NO: 44 and SEQ ID NO: 48.

In a preferred aspect, the antibodies of the invention are humanized antibodies comprising the G1 heavy chain of SEQ ID NO: 42 (FIG. 15) and the κ light chain of SEQ ID NO: 44 (FIG. 16) (e.g. Hu2EF-7); or comprising the G1 heavy chain of SEQ ID NO: 46 (FIG. 17) and the κ light chain of SEQ ID NO: 48 (FIG. 18) (e.g. Hu2G10-5 antibodies); or comprising the G1 heavy chain of SEQ ID NO: 50 (FIG. 19) and the κ light chain of SEQ ID NO: 48 (FIG. 18) (e.g. Hu2G10-6).

The fragments of the antibodies according to the present invention, include a Fv fragment, a Fab fragment, a F(ab)2 fragment, a single chain antibody, a bifunctional hybrid antibody or a multimeric antibody. The antibody or the antibody fragment or derivative or conjugate or the chimeric molecule or the immunoglobulin taught by the present invention may be or may result from the IgM, IgD, IgG, IgA, or IgE isotypes.

The antibodies and fragments thereof according to the present invention may contain additional molecules (immunoconjugates). A non-exhaustive list of such molecules includes for example radioactive isotopes, fluorescent tracers, enzymes that can be detected by chemiluminescence, cytokines or toxins, for example toxins with enzymatic activity and of bacterial, fungal, plant or animal origin, and their fragments.

The derivatives of the antibodies according to the present invention may be antibodies in which the constant regions are replaced by a biologically active molecule. A non-exhaustive list of biologically active molecules includes for example a member of the family of avidines, or a growth factor that can produce immunological effectors, or a pharmacologically active molecule, such as a toxin, a cytokine, or any other molecule that is able to increase therapeutic efficacy.

Objects of the present invention are also diagnostic and therapeutic compositions comprising the antibodies and immunoconjugates, according to the present invention, their fragments and derivatives alone or in combination with each other or with other molecules and in combination with one or more excipients, adjuvants, vehicles and/or pharmaceutically acceptable diluents.

A further object of the present invention is the use in diagnostics and therapy of the antibodies and immune conjugates according to the present invention, their fragments and derivatives, and compositions that contain them.

In an object of the present invention the diagnostic use can be applied as non-exclusive example to diagnostic imaging in vivo in patients.

In another object of the present invention diagnostics and therapy can be applied for example to pathologies associated with Trop-2, preferably tumors and their metastases. Still preferably diagnostics and therapy can be applied to tumors and their metastases that express Trop-2. A non-exhaustive list of tumors that express Trop-2 includes for example tumors of endometrium, breast, head and neck, colorectal, stomach, lung, ovary, prostate, pancreas, cervix, kidney and bladder (urothelial carcinoma).

In an object of the present invention the therapy is performed by administering pharmaceutical compositions to patients, said compositions containing the antibodies or their fragments or derivatives or immune conjugates according to the present invention, alone or in combination, in a pharmacologically acceptable form, in the course of neoplastic disease or after surgical removal of the tumor. The administration may also take place concurrently with other anti-cancer therapy, can be systemic, such as intravenous, or locoregional, eg intraperitoneal, intrapleural, intravesical, intra-hepatic artery, or intralesional (intra-tumor), or intra-operative, in which the pharmaceutical composition is deposited directly into the cavity left by surgical resection of the tumor mass. In an object of the present invention the therapy is immunotherapy. In another object of the present invention the therapy is radioimmunotherapy.

In the pharmaceutical composition according to the invention the antibodies or their derivatives or conjugates according to the present invention may be associated with other anticancer drugs.

The pharmaceutical compositions according to the invention may comprise the antibody or derivatives or conjugates or fragments thereof according to the present invention in combination with carrier agents, alone or together with other therapeutic agents, as e.g. anticancer drugs. In a specific embodiment of the present invention the carrier agents are liposomes.

The pharmaceutical composition is preferably in a form that is acceptable for systemic administration, including intravenous, or loco-regional administration, including intraperitoneal, intrapleural, intravesical, intralesion (intra-tumor) administration or administration through the hepatic artery, or intrasurgery administration where the pharmaceutical composition is deposited directly in the cavity hat is left after surgical removal of the tumor.

The therapeutic agent used in the present invention may be an anticancer drug which is a cytotoxic substance, intended as substance that inhibits or prevents the function of the cell and/or cause the destruction of the cell itself. Cytotoxic substances include radioactive isotopes, chemotherapeutic agents, and toxins, for example toxins equipped with enzymatic activity of bacterial, fungal, plant or animal origin, and their fragments. A chemotherapeutic agent is a chemical compound useful in the treatment of cancer. Examples of chemotherapeutic agents include but are not limited to: adriamycin, doxorubicin, 5-fluorouracil, cytosine-arabinoside ("Ara-C"), cyclophosphamide, thiotepa, busulfan, taxol, methotrexate, cisplatin, melphalan and other nitrogen mustards, vinblastine, bleomycin, etoposide, ifosfamide, mitomycin C, mitoxantrone, vincristine, vinorelbine, carboplatin, teniposide, aminopterin, dactinomycin, esperamicins. The agent can be an intercellular mediator, for example a cytokine, including non-exclusively lymphokines, monokines, hormones, growth factors, interferon, interleukins, coming from natural sources or from recombinant cell cultures, as well as biologically active equivalents of native cytokines.

The composition according to the invention comprises an effective amount of the humanized or fragment or derivative or conjugate thereof as above defined. Pharmaceutical compositions are conventional in this field and can be made by the person skilled in the art just based on the common general knowledge. In a preferred embodiment, the composition according to the invention is for use in intravenous administration.

It is also an object of the invention a method of treating and/or preventing a tumour or metastasis comprising administering a therapeutically effective amount the humanized or fragment or derivative or conjugate thereof as above defined.

It is an object of the invention a method of reducing and/or inhibiting Trop-2 comprising administering an effective amount of the humanized or fragment or derivative or conjugate thereof as above defined.

In the present invention mutants of the disclosed CDRs may be generated by mutating one or more amino acids in the sequence of the CDRs. It is known that a single amino acid substitution appropriately positioned in a CDR can be sufficient to improve the affinity. Directed mutagenesis may be used to increase affinity of some immunoglobulin products. This method of increasing or decreasing (i.e modulating) affinity of antibodies by mutating CDRs is common knowledge (see, e.g., Paul, W. E., 1993). Thus, the substitution, deletion, or addition of amino acids to the CDRs of the invention to increase or decrease (i.e, modulate) binding affinity or specificity is also within the scope of this invention.

The nucleotide sequences of SEQ ID NOs:13,15,17,19, 21,23,25,27,29,31,33,35,37,39 correspond to the different version of VH and VL of chimeric or humanized 2EF or 2G10.

The nucleotide sequences of SEQ ID NOs: 41,43,45,47, 49 are the complete sequence of the heavy or light chains of the humanized antibodies Hu2EF-7, Hu-2G10-5 or -6.

The definition of fragment, derivative or conjugate of a humanized antibody according to the invention, includes a scFv, a Fv fragment, a Fab fragment, a F(ab)2 fragment, a bifunctional hybrid antibody, a multimeric antibody, a derivative that contains biologically active molecules, including a member of the avidin family or a growth factor that can stimulate immunological effectors, or a pharmacologically active molecule, including a toxin, a cytokine, or any other molecule that is able to increase the therapeutic effect, an immunoconjugate, for example with radioactive isotopes, fluorescent tracers, enzymes for chemiluminescence, cytokines or toxins, including enzymatically active toxins of bacterial, fungal, vegetal or animal origin and fragments thereof.

It is a further object of the invention a host cell comprising the nucleic acid as described above. The host cell according to the invention also comprises a cell that has been transfected with the expression vector as above defined.

It is a further object of the invention a method of producing the humanized or fragment or derivative or conjugate thereof as described above of the invention comprising culturing the cell that produces the antibody as described above and recovering the antibody from the cell culture.

DETAILED DESCRIPTION OF THE INVENTION

In the present invention "at least 80% identity" means that the identity may be at least 80% or at least 85% or 90% or 95% or 100% sequence identity to referred sequences.

In the present invention "at least 50% homologue" means that the homology may be at least 50% or at least 60% or 70% or 80% or 90% or 95% or 100% sequence homology to referred sequences.

Preferably, the antibody or fragment or derivative or conjugate thereof as described above is a monoclonal antibody or a chimeric or a humanized, or a deimmunized or a fully human antibody.

A nucleic acid molecule that codes for an anti-Trop-2 monoclonal antibody or its fragments, derivatives or conjugates according to the present invention can be generated using technologies that are known in the art, such as gene synthesis or PCR amplification. The nucleic acid molecule can be cloned into an expression vector, with the recombinant DNA techniques that are known in the art. A vector for the expression of anti-Trop-2 monoclonal antibodies or their derivatives or conjugates according to the present invention can be inserted into host cell lines, for example by transfection. Methods of transfection are known and kits for transfection can be purchased from commercial sources (e.g., Stratagene, La Jolla, Calif.). Transfectants that stably express the humanized anti-Trop-2 monoclonal antibodies or their derivatives or conjugates according to the present invention can be selected according to techniques known in the art. Different clones of these transfectants can then be isolated and cultured, and the expression levels of each clone (amount of antibody or derivative secreted in the supernatant) can be quantified according to techniques known in the art. One example is the competitive binding to cells that express the antigen, in the presence of known amounts of fluorophore-labelled antibody or derivative; the fluorescent signal measured for example by flow cytometry according to techniques known in the art is inversely proportional to the amount of antibody or derivative produced by the clone in question. In this way a person skilled in the art can obtain cell lines that stably produce the antibodies or their derivatives in sufficient quantities for subsequent use, for example the production of a drug, and can validate quantitatively the production capacity of such cell line.

Cells that produce the anti-Trop-2 monoclonal antibodies or their derivatives or conjugates according to the present invention can be grown in media and culture conditions known in the art so as to maximize production. The Trop-2 monoclonal antibodies or their derivatives or conjugates according to the present invention can be purified by one skilled in the art using known processes, for example binding to protein A or to new synthetic materials, which can be arranged in a column or on a membrane, said purification being in batch or continuous. Production, purification and subsequent analytical control can also take place according to "Good Manufacturing Practices" GMP, known in the art, in accordance with the requirements that must be satisfied during the development, production and control of medicines for use in humans.

Derivatives of anti-Trop-2 monoclonal antibodies according to the present invention, such as functional fragments, or conjugates with biologically active molecules (eg toxins), or with radioisotopes, fluorescent dyes, enzymes that can be detected by chemiluminescence, can be obtained using chemical or genetic engineering procedures known in the art.

The anti-Trop-2 monoclonal antibodies and their derivatives or conjugates according to the present invention, in particular conjugates with radioactive isotopes or fluorescent or chemiluminescent tracers, can be used in imaging diagnostics of patients using technologies and procedures known in the art. The signal generated by the conjugated antibodies that bind the target in vivo is a specific indicator of antigen localization and can be revealed and quantified by tomographic instruments that are known in the art.

Another method of realization of the invention consists in the administration to patients with conditions associated with Trop-2, said condition being for example a neoplastic disease, of anti-Trop-2 monoclonal antibodies or their derivatives or conjugates according to the present invention, in combination or individually, for therapeutic purposes. Said administration can be systemic, for example intravenous, or loco-regional, for example, intraperitoneal, intrapleural, intravesical, intra-hepatic artery, or intralesional (intra-tumor), or intraoperative, wherein the pharmaceutical composition is directly deposited into the cavity left by the surgical resection of the tumor, according to the methods known in the art. In particular the therapy can be carried out by experts in art through multiple administrations, repeated over time, thanks to the nature of the anti-Trop-2 monoclonal antibodies or their derivatives or conjugates according to the present invention, which do not elicit an anti-mouse antibody response.

The process for the preparation of the antibody of the invention is within the skills of the man skilled in the art and comprises cultivating host cells that have been transfected with a vector for the expression of the antibody and isolating the antibody according to standard procedures.

As far as the industrial aspects of the present invention are concerned, the antibody herein disclosed shall be suitably formulated in pharmaceutical compositions as normally done in this technical field.

The antibodies of the present invention may comprise at least one CDRH as defined above that contains one or more amino acid substitutions, deletions or insertions of no more than 4 amino acids, preferably of no more than 2 amino acids. The antibodies of the present invention may further comprises at least one CDRL as defined above that contains one or more amino acid substitutions, deletions or insertions of no more than 4 amino acids, preferably of no more than 2 amino acids.

The method for treating or preventing a tumor or metastasis, comprises administering to a patient in need thereof an effective amount of at least one humanized antibody, fragments or derivatives or conjugates thereof as described above. In some aspects, the invention comprises a method for treating or preventing tumor or metastasis in a subject, the method comprising administering to a subject in need thereof an effective amount of at least one one humanized antibody, fragments or derivatives or conjugates thereof of the invention simultaneously or sequentially with an anti-cancer agent.

The invention provides formulations comprising a therapeutically effective amount of an antibody as disclosed herein, a buffer maintaining the pH in the range from about 4.5 to about 6.5, and, optionally, a surfactant.

The formulations are typically for an antibody as disclosed herein, fragments, derivatives or conjugates of the invention as active principle concentration from about 0.1 mg/ml to about 100 mg/ml. In certain embodiments, the antibody, recombinant or synthetic antigen-binding fragments thereof concentration is from about 0.1 mg/ml to 1 mg/ml; preferably from 1 mg/ml to 10 mg/ml, preferably from 10 to 100 mg/ml.

For the purposes herein, a "pharmaceutical composition" is one that is adapted and suitable for administration to a mammal, especially a human. Thus, the composition can be used to treat a disease or disorder in the mammal. Moreover, the antibody in the composition has been subjected to one or more purification or isolation steps, such that contaminant(s) that might interfere with its therapeutic use have been separated therefrom. Generally, the pharmaceutical composition comprises the therapeutic antibody and a pharmaceutically acceptable carrier or diluent. The composition is usually sterile and may be lyophilized. Pharmaceutical preparations are described in more detail below.

Therapeutic formulations of the antibody/antibodies can be prepared by mixing the antibody having the desired degree of purity with optional physiologically acceptable carriers, excipients or stabilizers (Remington's Pharmaceutical Sciences 16th edition, Osol, A. Ed., 1980), in the form of lyophilized formulations or aqueous solutions. Acceptable carriers, excipients, or stabilizers are nontoxic to recipients at the dosages and concentrations employed, and may include buffers, antioxidants, preservatives, peptides, proteins, hydrophilic polymers, chelating agents such as EDTA, sugars, salt-forming counter-ions such as sodium; metal complexes (e.g., Zn-protein complexes); and/or non-ionic surfactants such as TWEEN®, PLURONICS® or polyethylene glycol (PEG).

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed., 1980). The formulations to be used for in vivo administration must be sterile. This is readily accomplished by filtration through sterile filtration membranes.

In another embodiment, for the prevention or treatment of disease, the appropriate dosage of the antibody, fragments, derivatives or conjugate of the present invention, will depend on the type of disease to be treated, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg of antibody or fragment thereof is an initial candidate dosage for administration to the patient, whether, for example, by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

The antibody composition should be formulated, dosed, and administered in a fashion consistent with good medical practice. The antibodies/derivatives of the present invention can be administered by any appropriate route. This includes (but is not limited to) intraperitoneal, intramuscular, intravenous, subcutaneous, intraarticular, intratracheal, oral, enteral, parenteral, intranasal or dermal administration. A preferred mode of administration is the intravenous route. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat a disease or disorder. The antibody need not be, but is optionally formulated with one or more agents currently used to prevent or treat the disorder in question. The effective amount of such other agents depends on the amount of antibody present in the formulation, the type of disorder or treatment, and other factors discussed above.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. The term "antibody" herein comprise recombinant or synthetic antigen-binding fragments thereof.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

The term "conjugate" in relation to the antibody of the invention includes antibodies (or fragments thereof) conjugated with a substance (a compound, etc.) having anti-tumor activity and/or cell-killing activity or a cytotoxic agents such as various A chain toxins, ribosomes inactivating proteins, and ribonucleases; bispecific antibodies designed to induce cellular mechanisms for killing tumors (see, for example, U.S. Pat. Nos. 4,676,980 and 4,954,617). The conjugate may be formed by previously preparing each of the aforementioned antibody molecule and the aforementioned substance having anti-tumor activity and/or cell-killing activity, separately, and then combining them (immunoconjugate) or by ligating a protein toxin used as such a substance having anti-tumor activity and/or cell-killing activity to an antibody gene on a gene according to a genetic recombination technique, so as to allow it to express as a single protein (a fusion protein) (immunotoxin).

Examples of a substance having anti-tumor activity include doxorubicin, calicheamicin, mitomycin C, Auristatin E and radioactive isotope (RI). Examples of a substance having cell-killing activity include saporin, lysine, pseudomonas exotoxin, diphtheria toxin and radioactive isotope (RI). Of these, saporin and pseudomonas exotoxin are preferably used. A method for producing an antibody-drug conjugate is not limited. For example, a method of coupling an antibody with a drug via a disulfide bond or a hydrazone bond is applied. The aforementioned anti-TROP-2 antibody of the present invention is excellent in terms of internalization activity into target tumor cells that express TROP-2. Thus, by previously combining a substance having anti-tumor activity and cell-killing activity with the anti-TROP-2 antibody of the invention, it becomes possible to allow such a substance to directly and highly selectively act on the tumor cells.

In the context of the present invention, the expression of Trop-2 may be evaluated with any methods known to the skilled in the art.

Moreover, in the present invention, the aforementioned antibody-drug conjugate also include antibody fragment-drug conjugate, in which the aforementioned antibody fragment is used instead of an antibody.

An "antibody that binds to the same epitope" as a reference antibody refers to an antibody that blocks binding of the reference antibody to its antigen in a competition assay by 30% or more, and conversely, the reference antibody blocks binding of the antibody to its antigen in a competition assay by 30% or more. The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called [alpha], [delta], [epsilon], [gamma], and [mu], respectively.

The term "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91- 3242, Bethesda Md. (1991), vols. 1-3.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

In the context of the present invention "humanized" antibody also comprises chimeric antibodies, as e.g. the Ch2EF or the Ch2G10 antibody as above defined.

A "deimmunized" antibody is an antibody with reduced immunogenicity based on disruption of HLA binding, an underlying requirement for T cell stimulation.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (HI, H2, H3), and three in the VL (LI, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (LI), 50-52 (L2), 91-96 (L3), 26-32 (HI), 53-55 (H2), and 96-101 (H3) (Chothia and Lesk, J. Mol. Biol. 196:901-917, 1987). Exemplary CDRs (CDR-L1, CDR-L2, CDR-L3, CDR-H1, CDR-H2, and CDR-H3) occur at amino acid residues 24-34 of LI, 50-56 of L2, 89-97 of L3, 31-35B of HI, 50-65 of H2, and 95-102 of H3 (Kabat et al., Sequences of Proteins of Immunological Interest, 5th Ed. Public Health Service, National Institutes of Health, Bethesda, Md., 1991). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-LI, a-CDR-L2, a-CDR-L3, a-CDR-HI, a-CDR-H2, and a-CDR-H3) occur at amino acid residues 31-34 of LI, 50-55 of L2, 89-96 of L3, 31-35B of HI, 50-58 of H2, and 95-102 of H3 (See Almagro and Fransson, Front. Biosci. 13: 1619-1633, 2008). Unless otherwise indicated, HVR residues and other residues in the variable domain (e.g., FR residues) are numbered herein according to Kabat et al.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "package insert" is used to refer to instructions customarily included in commercial packages of therapeutic products, that contain information about the indications, usage, dosage, administration, combination therapy, contraindications and/or warnings concerning the use of such therapeutic products.

In the context of the present invention the term "having" may be intended as consisting of, having, having essentially or comprising.

The term "% homologue" may be intended as the polypeptide has a certain percentage identity with respect to the reference polypeptide sequence.

"Percent (%) amino acid sequence identity" or "Percent identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The method for diagnosis of tumor according to the present invention is characterized in that it comprises allowing the aforementioned anti-hTROP-2 antibody of the present invention to react with a sample collected from a living body (hereinafter referred to as a biological sample), and detecting a signal(s) of the reacted antibody.

The anti-TROP-2 antibody of the present invention is allowed to react with a biological sample, and a signal of the reacted antibody is then detected, so as to detect a tumor. The obtained antibody signal can be used as an indicator of the amount of an antigen in the biological sample. In detection of a tumor using the antibody of the present invention, first, a biological sample collected as an analyte from a subject, such as a tissue section or blood used as a test target, is allowed to bind to the antibody of the present invention by an antigen-antibody reaction. Subsequently, based on the measurement results of the amount of the bound antibody, the amount of an antigen of interest contained in the biological sample is measured. This measurement may be carried out in accordance with known immunoassay methods. For example, an immunoprecipitation method, an immunoagglutination method, radioimmunoassay, immunonephelometry, a Western blot method, flow cytometry and the like can be used. In radioimmunoassay, a labeled antibody is used, and thus an antibody signal is expressed as the amount of the labeled antibody that is directly detected. Otherwise, an antibody whose concentration or antibody titer has been known may be used as a standard solution, and thus a signal of the target antibody may be expressed as a relative value. That is, both the standard solution and the analyte may be measured using a measurement device, and an antibody signal in a biological sample may be expressed as a value relative to the value of the standard solution used as a criterion. Examples of such radioimmunoassay include the ELISA method, the EI method, the RIA method, fluorescence immunoassay (FIA), and luminescence immunoassay. Of these, the ELISA method is particularly preferable in that it is simple and highly sensitive.

In the present invention, the state of a tumor can be evaluated or diagnosed, using the detection result obtained by the aforementioned detection method as an indicator. For example, when the detection result exceeds a proper control or reference, the state of a tumor is defined as tumor positive, and when the detection result is less than the proper control or reference, it is defined as tumor negative. The term "the state of a tumor" is used herein to mean the presence or absence of the development of a tumor, or the progression degree thereof. Thus, specific examples of the state of a tumor include the presence or absence of the development of a tumor, the progression degree thereof, the degree of malignancy, the presence or absence of metastasis, and the presence or absence of recurrence.

In the aforementioned evaluation, as a state of a tumor to be evaluated, only one state may be selected from the aforementioned examples, or multiple examples may be combined and selected. The presence or absence of a tumor can be evaluated by determining whether or not the tumor has been developed, with reference to the predetermined standard value used as a boundary, based on the obtained detection result. The degree of malignancy is used as an indicator that indicates the progression degree of a cancer. Based on the detection result, the target tumor can be classified into a certain disease stage and it can be evaluated. Otherwise, an early cancer and an advanced cancer can be distinguished from each other, and then they can be evaluated. For example, it is also possible to determine the target tumor as an early cancer or an advanced cancer, using the detection result as an indicator. The metastasis of tumor can be evaluated by determining whether or not neoplasm has appeared at a site apart from the position of the initial lesion, using the detection result as an indicator. The recurrence can be evaluated by determining whether or not the detection result has exceeded the predetermined standard value again after interval stage or remission.

The anti-TROP-2 antibody of the present invention can be provided in the form of a kit for detecting or diagnosing a tumor. The kit of the present invention may comprise a labeling substance, a solid-phase reagent on which the antibody or the labeled antibody has been immobilized, etc., as well as the aforementioned antibody. A labeling substance that labels the antibody means a substance labeled with an enzyme, a radioisotope, a fluorescent compound, a chemiluminescent compound, etc. The kit of the present invention may also comprise other reagents used for carrying out the detection of the present invention, in addition to the aforementioned constitutional elements. For example, when such a labeling substance is an enzyme labeling substance, the kit of the present invention may comprise an enzyme substrate (a chromogenic substrate, etc.), an enzyme substrate-solving solution, an enzyme reaction stop solution, a diluent used for analytes, etc. Moreover, the present kit may further comprise various types of buffers, sterilized water, various types of cell culture vessels, various types of reactors (an Eppendorf tube, etc.), a blocking agent (a serum component such as bovine serum albumin (BSA), skim milk, or goat serum), a washing agent, a surfactant, various types of plates, an antiseptic such as sodium azide, an experimental operation manual (instruction), etc. The kit of the present invention can be effectively used to carry out the aforementioned detection method of the present invention. The kit of the invention optionally comprises control means that can be used to compare the amount or the increase of amount of the antibody as above defined to a value from a control sample. The value may be obtained for example, with reference to known standard, either from a normal subject or from normal population.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like.

The "detecting means" as above defined are preferably at least one antibody, functional analogous or derivatives thereof, or an enzyme substrate. Said antibody, functional analogous or derivatives thereof are specific for said antibody.

In a preferred embodiment, the kit of the invention comprises:

a solid phase adhered antibody specific for said antibody;
detection means of the ligand specific-antibody complex.

The kits according to the invention can further comprise customary auxiliaries, such as buffers, carriers, markers, etc. and/or instructions for use.

The antibodies taught by the present invention or their derivatives can be fused to sequences, single residues or synthetic molecules (tags) that allow antibody purification by affinity cromatography. The tags utilized can be used as detection molecules or indicators (e.g. radioisotopic or fluorescent tags) or enzymatic tags able to catalize a detectable substrate modification, both for diagnostic use in the lab and for imaging. The diagnostic techniques that can be utilized are for example optical, confocal, multiple foton and electronic microscopy, ELISA, Western blotting, immunoprecipitation, radioimmunological techniques and similar others.

The antibodies defined in the present invention can be used for the preparation of compositions for the detection of Trop-2 expressing neoplasias, including in vivo tumor imaging. Anti-Trop-2 antibodies can be linked to radioactive isotopes or fluorescent tracers, e.g. quantum dots or organic chromophores or enzymes which can be detected by chemiluminescence. The signal originated by labelled anti-Trop-2 antibodies is detectable by scanners or tomography instrumentation, according to the principles of currently used advanced equipment such as TAC/PET.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs, See, e.g., Kindt et al. Kuby Immunology, 6th ed., W.H. Freeman and Co., page 91, 2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (See, e.g., Portolano et al., J. Immunol. 150:880- 887, 1993; Clarkson et al., Nature 352:624-628, 1991).

The term "vector" as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

In another aspect, the antibody or derivatives thereof comprises a heavy chain variable domain (VH) sequence having at least 80%, 85%, 90%, 91%, 92%, 93%, 94%, 95%, 96%, 97%, 98%, 99%, or 100% sequence identity to an amino acid sequence selected from the group of: SEQ ID NO:14, 22, 24, 26, 18, 32 and 34.

In another aspect, the antibody or derivatives thereof comprises a light chain variable domain (VL) sequence having at least 80%, 85%, 90%, 91%, 92%, 93%, 94%, 95%, 96%, 97%, 98%, 99%, or 100% sequence identity to an amino acid sequence selected from the group of: SEQ ID NO: 16, 28, 30, 20, 36, 38 and 40.

In certain embodiments, the VH sequence or VL sequence having at least 80%, 85%, 90%, 91%, 92%, 93%, 94%, 95%, 96%, 97%, 98%, or 99% identity to said SEQ ID No. 14, 22, 24, 26, 18, 32, 34 or 16, 28, 30, 20, 36, 38 or 40 contains substitutions (e.g., conservative substitutions), insertions, or deletions relative to the reference sequence, but the anti Trop-2 antibody comprising that sequence retains the ability to bind to Trop-2 regions defined above. In certain embodiments, substitutions, insertions, or deletions occur in regions outside the HVRs (i.e. , in the FRs).

In certain embodiments, the antibody or fragment thereof of the invention has a dissociation constant (Kd) of <1000 nM, <100 nM, <10 nM, <1 nM, <0.1 nM, <0.01 nM, or <0.001 nM or less, e.g. from $10^{-6}$ M to $10^{-12}$ M.

In one embodiment, Kd is measured by a radio labeled antigen binding assay (RIA) performed with the Fab version of an antibody of interest and its antigen as described by the following assay. Solution binding affinity of Fabs for antigen is measured by equilibrating Fab with a minimal concentration of (I)-labeled antigen in the presence of a titration series of unlabeled antigen, then capturing bound antigen with an anti-Fab antibody-coated plate (see, e.g. , Chen et al., J. Mol. Biol. 293:865-881(1999)).

Preferably the pharmaceutical composition of the invention further comprises at least another therapeutic agent, preferably the other therapeutic agent is selected from the group of: anti-tumoral agent, anti-pain agent, anti-emetic agent (such as aprepitant, fosaprepitant, Dolasetron, granisetron, ondansetron, palonosetron, tropisetron, or ramosetron, Dexamethasone).

Preferably the other therapeutic agent is selected from the group consisting of: ATR inhibitor, DDR inhibitor, HR inhibitor, molecule that specifically target telomeres, preferably G-quadruplexes interacting molecules, molecule that cause DNA damage generation specifically at telomeres.

A composition to be used as an anti tumor agent may further contain other agents which either enhance the activity of the antibody or complement its activity or use in treatment, such as chemotherapeutic or radioactive agents. Such additional factors and/or agents may be included in the composition to produce a synergistic effect with the antibody (ies), or to minimize side effects. Additionally, administration of the composition of the present invention may be administered concurrently with other therapies, e. g., administered in conjunction with a chemotherapy or radiation therapy regimen. The antibodies as described herein can be used in combination with other compositions and procedures for the treatment of diseases. For example, a tumor may be treated conventionally with surgery, radiation, chemotherapy, or immunotherapy, combined with oligonucleotide therapy, and then antibodies may be subsequently administered to the patient to extend the dormancy of micrometastases and to stabilize and inhibit the growth of any residual primary tumor. Preferably the other therapeutic agent is selected from the group consisting of: ATR inhibitor, DDR inhibitor, HR inhibitor, molecule that specifically targets and/or causes DNA damage generation specifically at telomeres, preferably G-quadruplexes interacting molecules.

In the present invention an ATR inhibitor is a small molecule compound able to inhibit the kinase activity of ATR, comprising but not limited to VE-821 (Vertex Pharmaceuticals), VE-822 (Vertex Pharmaceuticals), AZ20 (AstraZeneca), AZD6738 (AstraZeneca) (as described in Flynn et al, Science, 2015; Weber A M, Pharmacol Ther. 2015, all references are incorporated by reference).

A DDR inhibitor is any compound or experimental approach able to impair or inhibit the cellular process known as DNA damage response (DDR), comprising but not limited to: Caffeine, Wortmannin, KU-55933, KU-60019, KU-559403, Schisandrin B, NU6027, NVP-BEZ235, (as described in Begg A C, Nat Rev Cancer. 2011; Weber A M, Pharmacol Ther. 2015; Kelley M R, Future Oncol. 2014, all references are incorporated by reference).

A HR inhibitor is any compound or experimental approach able to impair or inhibit the cellular process known as DNA repair by homologous recombination (HR), comprising but not limited to: Iniparib (SAR240550, BSI-201; Sanofi-Aventis), Olaparib (AZD2281, KU-0069436; AstraZeneca), Niraparib (Tesaro), Rucaparib (CO-338, AG-014699, PF-O1367338; Pfizer), Veliparib (ABT-888; Abbott), AZD2461 (AstraZeneca), BMN673 (BioMarin Pharmaceutical), CEP-9722 (Cephalon), E7016 (Esai), INO-1001 (Inotek Pharmaceuticals), MK-4827 (Merck), Methoxyamine (Sigma Aldrich), RI-1, IBR2, B02, Halenaquinone (described in Kelley M R, Future Oncol. 2014, Ward A, Cancer Treat Rev. 2015, Feng F Y, Mol Cell. 2015, all references are incorporated by reference).

A molecule that specifically targets and/or causes DNA damage generation at telomeres is any compound or experimental approach which specifically or preferentially interacts with telomeres, inducing DNA damage within telomeric DNA and/or activation or inhibition of DDR signalling and/or DNA repair, comprising but not limited to: G-quadruplex-binding ligands (e.g. BRACO-19, Telomestatin, RHPS4, Quarfloxin, TMPyP4, AS1410), topoisomerase inhibitors, cisplatin, hydroxyurea, (as described in Lu et al, Front. Med. 2013; Neidle FEBS J, 2010; Müller and Rodriguez, Expert Rev Clin Pharmacol. 2014; Sissi and Palumbo, Curr Pharm Des. 2014, Salvati et al, NAR, 2015, all references are incorporated by reference).

Other molecules that can be used in combination with the present antibodies are: Abitrexate (Methotrexate Injection), Abraxane (Paclitaxel Injection), Adcetris (Brentuximab Vedotin Injection), Adriamycin (Doxorubicin), Adrucil Injection (5-FU (fluorouracil)), Afinitor (Everolimus), Afinitor Disperz (Everolimus), Alimta (PEMETREXED), Alkeran Injection (Melphalan Injection), Alkeran Tablets (Melphalan), Aredia (Pamidronate), Arimidex (Anastrozole), Aromasin (Exemestane), Arranon (Nelarabine), Arzerra (Ofatumumab Injection), Avastin (Bevacizumab), Bexxar (Tositumomab), BiCNU (Carmustine), Blenoxane (Bleomycin), Bosulif (Bosutinib), Busulfex Injection (Busulfan Injection), Campath (Alemtuzumab), Camptosar (Irinotecan), Caprelsa (Vandetanib), Casodex (Bicalutamide), CeeNU (Lomustine), CeeNU Dose Pack (Lomustine), Cerubidine (Daunorubicin), Clolar (Clofarabine Injection), Cometriq (Cabozantinib), Cosmegen (Dactinomycin), CytosarU (Cytarabine), Cytoxan (Cytoxan), Cytoxan Injection (Cyclophosphamide Injection), Dacogen (Decitabine), DaunoXome (Daunorubicin Lipid Complex Injection), Decadron (Dexamethasone), DepoCyt (Cytarabine Lipid Complex Injection), Dexamethasone Intensol (Dexamethasone), Dexpak Taperpak (Dexamethasone), Docefrez (Docetaxel), Doxil (Doxorubicin Lipid Complex Injection), Droxia (Hydroxyurea), DTIC (Decarbazine), Eligard (Leuprolide), Ellence (Ellence (epirubicin)), Eloxatin (Eloxatin (oxaliplatin)), Elspar (Asparaginase), Emcyt (Estramustine), Erbitux (Cetuximab), Erivedge (Vismodegib), Erwinaze (Asparaginase Erwinia chrysanthemi), Ethyol (Amifostine), Etopophos (Etoposide Injection), Eulexin (Flutamide), Fareston (Toremifene), Faslodex (Fulvestrant), Femara (Letrozole), Firmagon (Degarelix Injection), Fludara (Fludarabine), Folex (Methotrexate Injection), Folotyn (Pralatrexate Injection), FUDR (FUDR (floxuridine)), Gemzar (Gemcitabine), Gilotrif (Afatinib), Gleevec (Imatinib Mesylate), Gliadel Wafer (Carmustine wafer), Halaven (Eribulin Injection), Herceptin (Trastuzumab), Hexalen (Altretamine), Hycamtin (Topotecan), Hycamtin (Topotecan), Hydrea (Hydroxyurea), Iclusig (Ponatinib), Idamycin PFS (Idarubicin), Ifex (Ifosfamide), Inlyta (Axitinib), Intron A alfab (Interferon alfa-2a), Iressa (Gefitinib), Istodax (Romidepsin Injection), Ixempra (Ixabepilone Injection), Jakafi (Ruxolitinib), Jevtana (Cabazitaxel Injection), Kadcyla (Ado-trastuzumab Emtansine), Kyprolis (Carfilzomib), Leukeran (Chlorambucil), Leukine (Sargramostim), Leustatin (Cladribine), Lupron (Leuprolide), Lupron Depot (Leuprolide), Lupron DepotPED (Leuprolide), Lysodren (Mitotane), Marqibo Kit (Vincristine Lipid Complex Injection), Matulane (Procarbazine), Megace (Megestrol), Mekinist (Trametinib), Mesnex (Mesna), Mesnex (Mesna Injection), Metastron (Strontium-89 Chloride), Mexate (Methotrexate Injection), Mustargen (Mechlorethamine), Mutamycin (Mitomycin), Mylleran (Busulfan), Mylotarg (Gemtuzumab Ozogamicin), Navelbine (Vinorelbine), Neosar Injection (Cyclophosphamide Injection), Neulasta (filgrastim), Neulasta (pegfilgrastim), Neupogen (filgrastim), Nexavar (Sorafenib), Nilandron (Nilandron (nilutamide)), Nipent (Pentostatin), Nolvadex (Tamoxifen), Novantrone (Mitoxantrone), Oncaspar (Pegaspargase), Oncovin (Vincristine), Ontak (Denileukin Diftitox), Onxol (Paclitaxel Injection), Panretin (Alitretinoin), Paraplatin (Carboplatin), Perjeta (Pertuzumab Injection), Platinol (Cisplatin), Platinol (Cisplatin Injection), PlatinolAQ (Cisplatin), PlatinolAQ (Cisplatin Injection), Pomalyst (Pomalidomide), Prednisone Intensol (Prednisone), Proleukin (Aldesleukin), Purinethol (Mercaptopurine), Reclast (Zoledronic acid), Revlimid (Lenalidomide), Rheumatrex (Methotrexate), Rituxan (Rituximab), RoferonA alfaa (Interferon alfa-2a), Rubex (Doxorubicin), Sandostatin (Octreotide), Sandostatin LAR Depot (Octreotide), Soltamox (Tamoxifen), Sprycel (Dasatinib), Sterapred (Prednisone), Sterapred DS (Prednisone), Stivarga (Regorafenib), Supprelin LA (Histrelin Implant), Sutent (Sunitinib), Sylatron (Peginterferon Alfa-2b Injection (Sylatron)), Synribo (Omacetaxine Injection), Tabloid (Thioguanine), Taflinar (Dabrafenib), Tarceva (Erlotinib), Targretin Capsules (Bexarotene), Tasigna (Decarbazine), Taxol (Paclitaxel Injection), Taxotere (Docetaxel), Temodar (Temozolomide), Temodar (Temozolomide Injection), Tepadina (Thiotepa), Thalomid (Thalidomide), TheraCys BCG (BCG), Thioplex (Thiotepa), TICE BCG (BCG), Toposar (Etoposide Injection), Torisel (Temsirolimus), Treanda (Bendamustine hydrochloride), Trelstar (Triptorelin Injection), Trexall (Methotrexate), Trisenox (Arsenic trioxide), Tykerb (lapatinib), Valstar (Valrubicin Intravesical), Vantas (Histrelin Implant), Vectibix (Panitumumab), Velban (Vinblastine), Velcade (Bortezomib), Vepesid (Etoposide), Vepesid (Etoposide Injection), Vesanoid (Tretinoin), Vidaza (Azacitidine), Vincasar PFS (Vincristine), Vincrex (Vincristine), Votrient (Pazopanib), Vumon (Teniposide), Wellcovorin IV (Leucovorin Injection), Xalkori (Crizotinib), Xeloda (Capecitabine), Xtandi (Enzalutamide), Yervoy (Ipilimumab Injection), Zaltrap (Ziv-aflibercept Injection), Zanosar (Streptozocin), Zelboraf (Vemurafenib), Zevalin (Ibritumomab Tiuxetan), Zoladex (Goserelin), Zolinza (Vorinostat), Zometa (Zoledronic acid), Zortress (Everolimus), Zytiga (Abiraterone), Nimotuzumab and immune checkpoint inhibitors such as nivolumab, pembrolizumab/MK-3475, pidilizumab and AMP-224 targeting PD-1; and BMS-935559, MEDI4736, MPDL3280A and MSB0010718C targeting PD-L1 and those targeting CTLA-4 such as ipilimumab.

Radiotherapy means the use of radiation, usually X-rays, to treat illness. X-rays were discovered in 1895 and since then radiation has been used in medicine for diagnosis and investigation (X-rays) and treatment (radiotherapy). Radiotherapy may be from outside the body as external radiotherapy, using X-rays, cobalt irradiation, electrons, and more rarely other particles such as protons. It may also be from within the body as internal radiotherapy, which uses radioactive metals or liquids (isotopes) to treat cancer.

Still further aspects include combining the antibodies described herein with other anticancer therapies for synergistic or additive benefit.

The schedule of treatment with the combinations can foresee that the antibdoy is administered concomitantly, before and/or after any of the "partner" therapeutic agent identified above.

Combination therapies can be utilized for advanced stage of disease but also, prospectively, in the adjuvant and neo-adjuvant setting.

The present invention shall now be disclosed in details by way of illustration and example, for illustrative but not limitative purposes, according, but not limited, to some of its preferred embodiments, with particular reference to the figures of the enclosed drawings FIG. 1: Nucleotide and amino acid sequence of Ch2EF VH. Amino acid residues are shown in single letter code. The signal peptide sequence is in italics. The N-terminal amino acid residue (Q) of the mature VH is double-underlined. CDR sequences are according to the definition of Kabat et al. (Kabat, Wu et al. 1991) and are underlined FIG. 2: Nucleotide and amino acid sequence of Ch2EF VL. The signal peptide sequence is in italics. The N-terminal amino acid residue (D) of the mature VL is double-underlined. CDR sequences are underlined.

FIG. 3: Nucleotide and amino acid sequence of Ch2G10 VH. The sequence of the signal peptide is in italics. The N-terminal amino acid residue (Q) of the mature VH is double-underlined. The CDR sequences are underlined.

FIG. 4: Nucleotide and amino acid sequence of Ch2G10 VL. The sequence of the signal peptide is in italics. The N-terminal amino acid residue (E) of the mature VL is double-underlined. The CDR sequences are underlined.

FIG. 5: Nucleotide and amino acid sequence of Hu2EF VH4. The sequence of the signal peptide is in italics. The N-terminal amino acid residue (Q) of the mature VH is double-underlined. The CDR sequences are underlined.

FIG. 6: Nucleotide and amino acid sequence of Hu2EF VH5. The sequence of the signal peptide is in italics. The N-terminal amino acid residue (Q) of the mature VH is double-underlined. The CDR sequences are underlined.

FIG. 7: Nucleotide and amino acid sequence of Hu2EF VH7. The sequence of the signal peptide is in italics. The N-terminal amino acid residue (Q) of the mature VH is double-underlined. The CDR sequences are underlined.

FIG. 8: Nucleotide and amino acid sequence of Hu2EF VL1. The sequence of the signal peptide is in italics. The N-terminal amino acid residue (D) of the mature VL is double-underlined. The CDR sequences are underlined.

FIG. 9: Nucleotide and amino acid sequence of Hu2EF VL2. The sequence of the signal peptide is in italics. The N-terminal amino acid residue (D) of the mature VL is double-underlined. The CDR sequences are underlined.

FIG. 10: Nucleotide and amino acid sequence of Hu2G10 VH1. The sequence of the signal peptide is in italics. The N-terminal amino acid residue (Q) of the mature VH is double-underlined. The CDR sequences are underlined.

FIG. 11: Nucleotide and amino acid sequence of Hu2G10 VH2. The sequence of the signal peptide is in italics. The N-terminal amino acid residue (Q) of the mature VH is double-underlined. The CDR sequences are underlined.

FIG. 12: Nucleotide and amino acid sequence of Hu2G10 VL1. The sequence of the signal peptide is in italics. The N-terminal amino acid residue (D) of the mature VL is double-underlined. The CDR sequences are underlined.

FIG. 13: Nucleotide and amino acid sequence of Hu2G10 VL2. The sequence of the signal peptide is in italics. The N-terminal amino acid residue (D) of the mature VL is double-underlined. The CDR sequences are underlined.

FIG. 14: Nucleotide and amino acid sequence of Hu2G10 VL3. The sequence of the signal peptide is in italics. The N-terminal amino acid residue (D) of the mature VL is double-underlined. The CDR sequences are underlined.

FIG. 15: Nucleotide and amino acid sequence of the coding region of Hu2EF-7G1 heavy chain. Asterisk "*" indicates the termination codon.

FIG. 16: Nucleotide and amino acid sequence of the coding region of Hu2EF-7 κ light chain. Asterisk "*" indicates the termination codon.

FIG. 17: Nucleotide and amino acid sequence of the coding region of Hu2G10-5 G1 heavy chain. Asterisk "*" indicates the termination codon.

FIG. 18: Nucleotide and amino acid sequence of the coding region of Hu2G10-5 and Hu2G10-6 κ light chain. Asterisk "*" indicates the termination codon.

FIG. 19: Nucleotide and amino acid sequence of the coding region of Hu2G10-6 G1 heavy chain. Asterisk "*" indicates the termination codon.

FIG. 20: Nucleotide and amino acid sequence of the Ch2EF VH synthetic gene flanked by SpeII and HindIII sites (underlined). The signal peptide sequence is in italics. The N-terminal amino acid residue (Q) of the mature VH is double-underlined. CDR sequences are underlined. The intron sequence at the 3' of the coding region is in italics.

FIG. 21: Nucleotide and amino acid sequence of the Ch2EF VL synthetic gene flanked by NheI and EcoRI sites (underlined). The signal peptide sequence is in italics. The N-terminal amino acid residue (D) of the mature VL is double-underlined. CDR sequences are underlined. The intron sequence at the 3' of the coding region is in italics.

FIG. 22: Schematic structure of the vector that was used for pCh2EF, pCh2G10, pHu2EF-4, pHu2EF-5, pHu2EF-7, pHu2G10-1, pHu2G10-2, pHu2G10-3, pHu2G10-4, pHu2G10-5 e pHu2G10-6(collectively Expression Vector). Proceeding clockwise from the SalI site at the top, the plasmid contains the heavy chain transcription unit starting with the human cytomegalovirus (CMV) major immediate early promoter and enhancer (CMV promoter). The CMV promoter is followed by the VH exon, a genomic sequence containing the human G1 heavy chain constant region including the CH1, hinge, CH2 and CH3 exons with the intervening introns, and the polyadenylation site following the CH3 exon. After the heavy chain gene sequence, the light chain transcription unit begins with the CMV promoter, followed by the VL exon and a genomic sequence containing the human κ chain constant region exon (CL) with part of the intron preceding it, and the polyadenylation site following the CL exon. The light chain gene is then followed by the SV40 early promoter (SV40 promoter), the E. coli xanthine guanine phosphoribosyl transferase gene (gpt), and a segment containing the SV40 polyadenylation site (SV40 poly(A) site). Finally, the plasmid contains a part of the plasmid pUC19, comprising the bacterial origin of replication (pUCori) and beta-lactamase gene (beta lactamase). In pHu2EF-7-puro, which is a derivative of pHu2EF-7, the gpt gene is replaced by the puromycin N-acetyltransferase gene for puromycin resistance.

FIG. 23: Humanization of the 2EF VH in M17751. Alignment of the amino acid sequences of mouse 2EF VH, two forms of humanized 2EF VH (Hu2EF VH4 and VH7), and human acceptor M17751.1. Numbers above the sequences indicate the locations according to Kabat et al. (Kabat, Wu et al. 1991). CDR sequences are underlined in 2EF VH. CDR residues in M17751.1 VH are omitted in the figure. The underlined residues in Hu2EF VH4 and VH7 were predicted to be important for the formation of the antigen binding site, and the corresponding mouse residues were retained at these locations FIG. 24: Humanization of the 2EF VH in L02325.1. Alignment of the amino acid sequences of mouse 2EF VH, humanized 2EF VH (Hu2EF VH5), and human acceptor L02325.1 sequences. Numbers above the sequences indicate the locations according to Kabat et al. (Kabat, Wu et al.

1991). CDR sequences are underlined in 2EF VH. CDR residues in L02325.1 VH are omitted in the figure. The underlined residues in Hu2EF VH5 were predicted to be important for the formation of the antigen binding site, and the corresponding mouse residues were retained at these locations.

FIG. 25: Humanization of the 2EF VL in Z46622.1. Alignment of the amino acid sequences of 2EF VL, two forms of humanized 2EF VL (Hu2EF VL1 and VL2) and human acceptor Z46622.1. Numbers above the sequences indicate the positions according to Kabat et al. (Kabat, Wu et al. 1991). CDR sequences are underlined in the 2EFCDRs. CDR residues in Z46622.1 VL are omitted in the figure. The underlined residues in Hu2EF VL1 and VL2 were predicted to be important for the formation of the antigen binding site and the corresponding mouse residues were retained at these locations.

FIG. 26: Nucleotide and amino acid sequence of the Hu2EF VH4 synthetic gene flanked by SpeI and HindIII sites (underlined). The signal peptide sequence is in italics. The N-terminal amino acid residue (Q) of the mature VH is double-underlined. CDR sequences are underlined. The intron sequence at the 3' of the coding region is in italics.

FIG. 27: Nucleotide and amino acid sequence of the Hu2EF VH5 synthetic gene flanked by SpeI and HindIII sites (underlined). The signal peptide sequence is in italics. The N-terminal amino acid residue (Q) of the mature VH is double-underlined. CDR sequences are underlined. The intron sequence at the 3' of the coding region is in italics.

FIG. 28: Nucleotide and amino acid sequence of the Hu2EF VL1 synthetic gene flanked by NheI and EcoRI sites (underlined). The signal peptide sequence is in italics. The N-terminal amino acid residue (D) of the mature VL is double-underlined. CDR sequences are underlined. The intron sequence at the 3' of the coding region is in italics.

FIG. 29: Binding of purified 2EF, Hu2EF-4 and Hu2EF-5 antibodies to the antigen-ELISA assay. An ELISA plate was coated with 0.1 µg/well of human Trop-2-Fc fusion protein (rhTrop2) Each antibody was tested at various concentrations, starting from 5 µg/ml with subsequent serial 2-fold dilutions. The graph shows the absorbance values (Y-axis) for each antibody concentration tested (X-axis).

FIG. 30: Relative affinity of the 2EF, Hu2EF-4 and Hu2EF-5 antibodies for Trop-2-ELISA assay. Binding of biotinylated mouse 2EF antibody to rhTrop-2 was analyzed in the presence of various concentrations of unlabelled competitor antibody (mouse 2EF, Hu2EF-4 or Hu2EF-5). The graph shows the absorbance values (Y-axis) for each competitor antibody concentration tested (X-axis).

Figure 31:
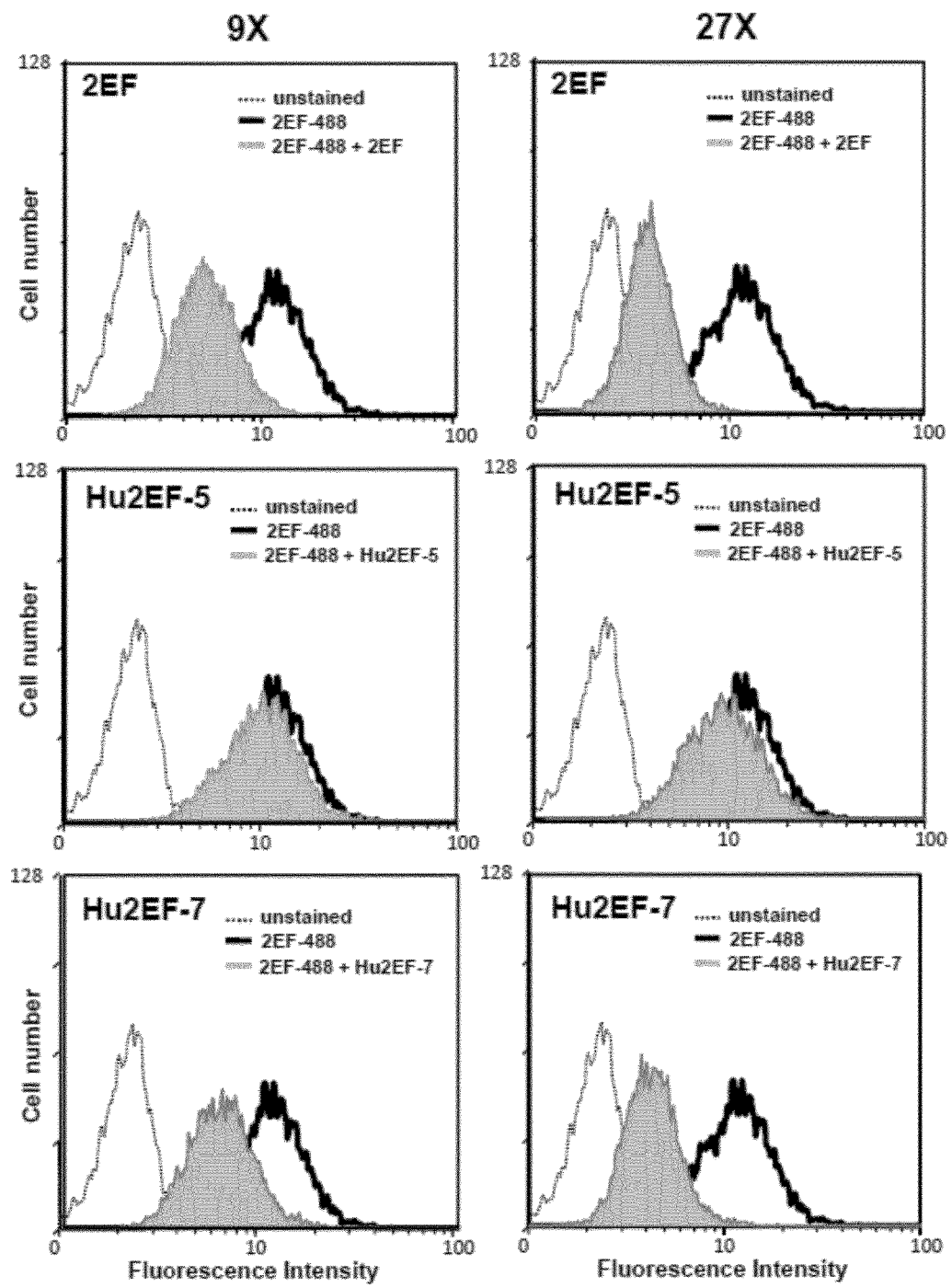

FIG. 31: Relative affinity of the 2EF, Hu2EF-5 and Hu2EF-7 antibodies for native endogenous Trop-2—Flow citometry analysis. Human colon cancer COLO205 cells, which are positive for Trop-2, were incubated with 0.3 µg of 2EF antibody conjugated to Alexa 488 (2EF-488) either alone (thick line) or pre-mixed with 2.7 µg (9X, on the left) or 8.1 µg (27X, on the right) of unlabelled 2EF (gray profile; top), Hu2EF-5 (middle) or Hu2EF-7 (bottom) competitor antibody. The dotted line corresponds to the unstained negative control.

FIG. 32: Binding of the 2EF, Hu2EF-4 and Hu2EF-5 purified antibodies to the antigen—ELISA assay. An ELISA plate was coated with 0.01 µg/well of rhTrop2. Each antibody was tested at various concentrations, starting from 1 µg/ml with subsequent serial 2-fold dilutions. The graph shows the absorbance values (Y-axis) for each antibody concentration tested (X-axis).

FIG. 33: Nucleotide and amino acid sequence of the Hu2EF VH7 synthetic gene flanked by SpeI and HindIII sites (underlined). The signal peptide sequence is in italics. The N-terminal amino acid residue (Q) of the mature VH is double-underlined. CDR sequences are underlined. The intron sequence at the 3' of the coding region is in italics FIG. 34: Nucleotide and amino acid sequence of the Hu2EF VL2 synthetic gene flanked by NheI and EcoRI sites (underlined). The signal peptide sequence is in italics. The N-terminal amino acid residue (D) of the mature VL is double-underlined. CDR sequences are underlined. The intron sequence at the 3' of the coding region is in italics.

FIG. 35: Binding of the Ch2EF and Hu2EF-7 purified antibodies to the antigen—ELISA assay. An ELISA plate was coated with 0.01 µg/well of rhTrop2. Each antibody was tested at various concentrations, starting from 1 µg/ml with subsequent serial 2-fold dilutions. The graph shows the absorbance values (Y-axis) for each antibody concentration tested (X-axis).

Figure 36:
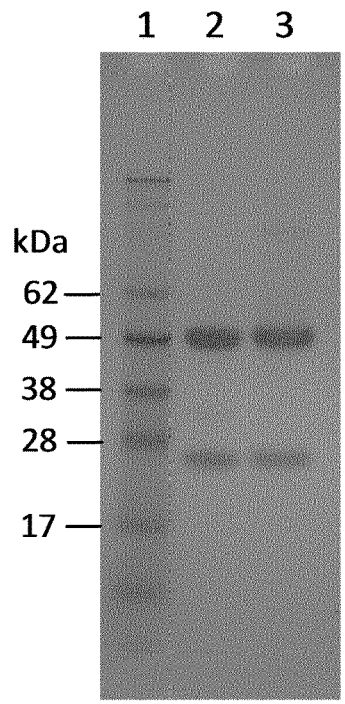

FIG. 36: SDS PAGE analysis of purified Hu2EF-7 antibodies. Antibodies (5 µg/lane) were analysed by SDS PAGE on a 4-20% gradient polyacrylamide gel (Cat #NP0335, Life Technologies) under reducing conditions, and stained with SimplyBlue Safestain (Cat #LC5925, Life Technologies). Lane 1, SeeBluePlus2 Prestained Standard (Cat #LC5925, Life Technologies); lane 2, Hu2EF-7 purified from CHO-K1-Hu2EF-7 2A2.2 cells; lane 3, Hu2EF-7 purified from YB2/0-Hu2EF-7 2D3 cells.

Figure 37:
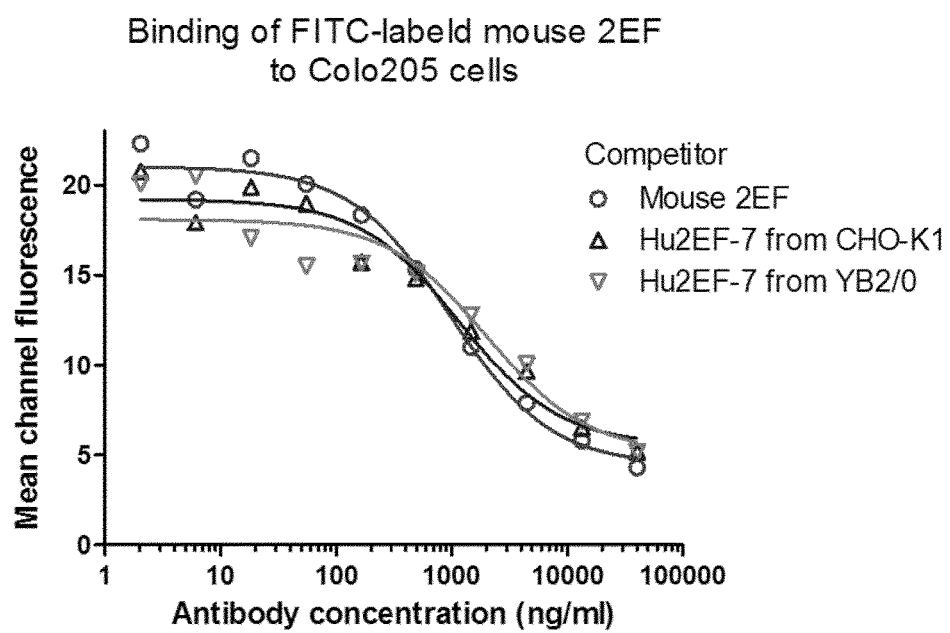

FIG. 37: Relative affinity of the 2EF and Hu2EF-7 antibodies for native Trop-2—Flow citometry analysis. Human colon cancer COLO205 cells, which are positive for Trop-2, were incubated with FITC-labelled 2EF antibody pre-mixed with increasing concentrations of unlabelled Hu2EF-7 purified from CHO-K1 or YB2/0 cells. The graph shows the mean fluorescence values (Y-axis) for each competitor antibody concentration tested (X-axis).

Figure 38:
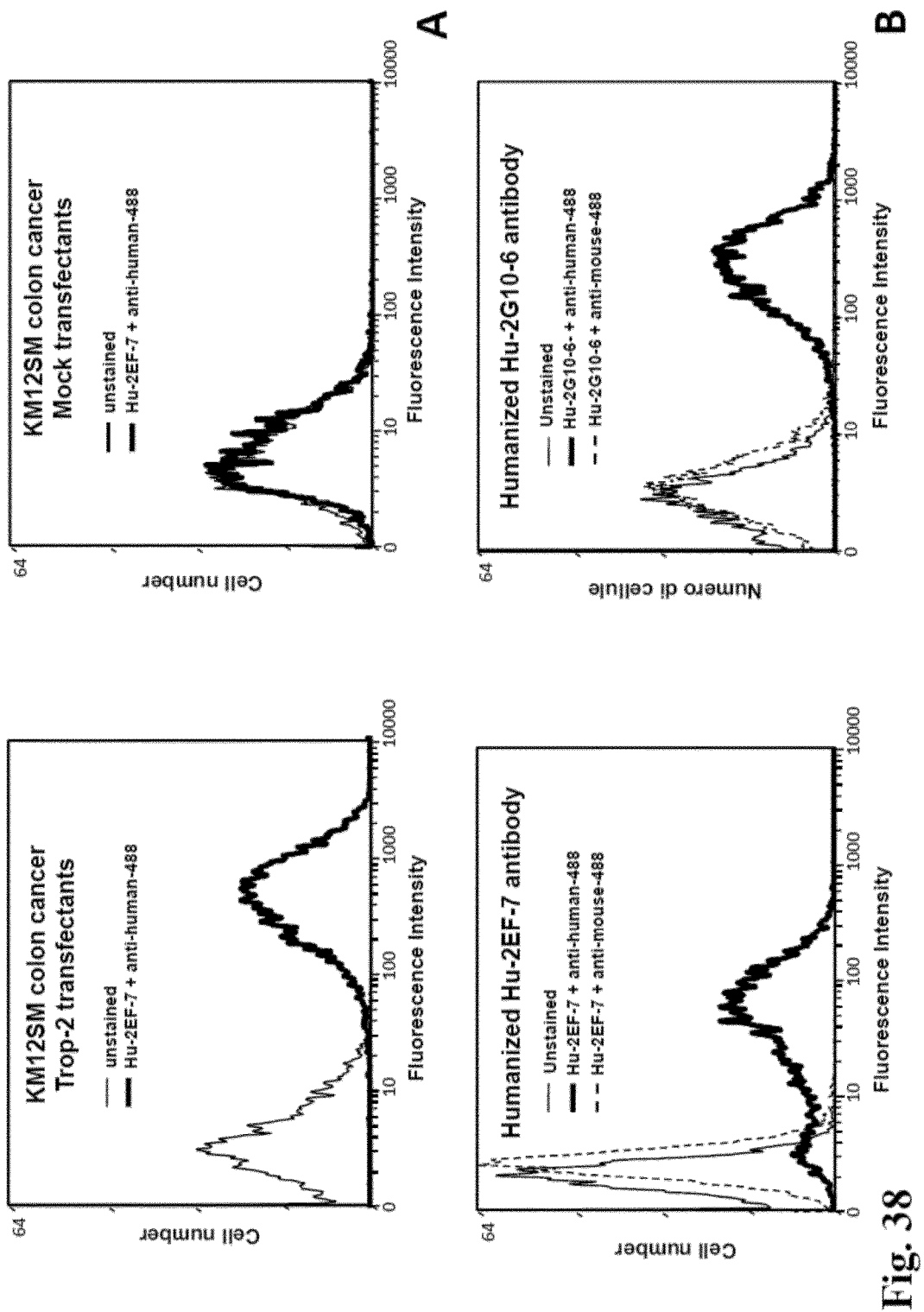

FIG. 38: Specific recognition of Trop-2 by the humanized monoclonal antibodies according to the present invention - analysis by flow cytometry. (A) human metastatic colon cancer KM12SM cells transfected with a vector expressing Trop-2 (left panel) or with the empty vector (right panel) were incubated with the 'humanized anti-Trop-2 monoclonal antibody Hu2EF-7. A subsequent incubation with a goat anti-human antiserum conjugated to Alexa-488 fluorophore (Goat anti-human IgG 488 Cat.A11013 Life Technologies, Carlsbad, Calif.) (thick line) reveals binding of Hu2EF-7 with Trop-2 (left panel) and absence of staining in the absence of Trop-2 (right panel). Unstained negative controls (thin line) are shown for comparison. (B) Human colon cancer HT29 cells (left panel) or breast cancer MCF-7 cells (right panel) expressing Trop-2 were incubated with the humanized Hu-2EF-7 and Hu-2G10-6anti-Trop-2monoclonal antibodies respectively. Binding with Trop-2 was revealed by a subsequent incubation with a goat anti-human antiserum conjugated to Alexa-488 (thick line). On the contrary, the anti-mouse-488 antiserum (Goat anti mouse IgG 488 Cat. A11029 Life Technologies) (dotted line) does not bind the humanized antibodies and does not produce fluorescent signal, and so does the unstained negative control (thin line).

FIG. 39: Nucleotide and amino acid sequence of the Ch2G10 VH synthetic gene flanked by SpeII and HindIII sites (underlined). The signal peptide sequence is in italics. The N-terminal amino acid residue (Q) of the mature VH is double-underlined. CDR sequences are underlined. The intron sequence at the 3' of the coding region is in italics.

FIG. 40: Nucleotide and amino acid sequence of the Ch2G10 VL synthetic gene flanked by NheI and EcoRI sites (underlined). The signal peptide sequence is in italics. The N-terminal amino acid residue (E) of the mature VL is double-underlined. CDR sequences are underlined. The intron sequence at the 3' of the coding region is in italics.

FIG. 41: Humanization of the 2G10 VH in X65888.1. Alignment of the amino acid sequences of mouse 2G10 VH, two forms of humanized 2G10 VH (Hu2G10 VH1 and VH2), and human acceptor X65888.1. Numbers above the sequences indicate the locations according to Kabat et al. (Kabat, Wu et al. 1991). CDR sequences are underlined in 2G10 VH. CDR residues in X65888.1VH are omitted in the figure. The underlined residues in Hu2G10 VH1 and VH2 were predicted to be important for the formation of the antigen binding site, and the corresponding mouse residues were retained at these locations.

FIG. 42: Humanization of the 2G10 VL in AY043146.1. Alignment of the amino acid sequences of mouse 2G10 VL, three forms of humanized 2G10 VL (Hu2G10 VL1, VL2 and VL3), and human acceptor AY043146.1. CDR sequences are underlined in 2G10 VL. CDR residues in AY043146.1VL are omitted in the figure. The underlined residues in Hu2G10 VL1, VL2 and VL3 were predicted to be important for the formation of the antigen binding site, and the corresponding mouse residues were retained at these locations.

FIG. 43: Nucleotide and amino acid sequence of the Hu2G10 VH1 synthetic gene flanked by SpeI and HindIII sites (underlined). The signal peptide sequence is in italics. The N-terminal amino acid residue (Q) of the mature VH is double-underlined. CDR sequences are underlined. The intron sequence at the 3' of the coding region is in italics.

FIG. 44: Nucleotide and amino acid sequence of the Hu2G10 VH2 synthetic gene flanked by SpeI and HindIII sites (underlined). The signal peptide sequence is in italics. The N-terminal amino acid residue (Q) of the mature VH is double-underlined. CDR sequences are underlined. The intron sequence at the 3' of the coding region is in italics.

FIG. 45: Nucleotide and amino acid sequence of the Hu2G10 VL1 synthetic gene flanked by NheI and EcoRI sites (underlined). The signal peptide sequence is in italics. The N-terminal amino acid residue (D) of the mature VL is double-underlined. CDR sequences are underlined. The intron sequence at the 3' of the coding region is in italics.

FIG. 46: Nucleotide and amino acid sequence of the Hu2G10 VL2 synthetic gene flanked by NheI and EcoRI sites (underlined). The signal peptide sequence is in italics. The N-terminal amino acid residue (D) of the mature VL is double-underlined. CDR sequences are underlined. The intron sequence at the 3' of the coding region is in italics.

FIG. 47: Nucleotide and amino acid sequence of the Hu2G10 VL3 synthetic gene flanked by NheI and EcoRI sites (underlined). The signal peptide sequence is in italics. The N-terminal amino acid residue (D) of the mature VL is double-underlined. CDR sequences are underlined. The intron sequence at the 3' of the coding region is in italics.

FIG. 48: SDS PAGE analysis of purified chimeric and humanized 2G10 antibodies. Antibodies (7.5 μg/lane) were analysed by SDS PAGE on a 4-20% gradient polyacrylamide gel under reducing conditions, and stained with Simply-Blue Safestain. Lane 1: Ch2G10; lane 2, Hu2G10-5; lane 3, Hu2G10-6. Lane M: SeeBluePlus2 Prestained Standard.

FIG. 49: Nucleotide and amino acid sequence of the coding region of Ch2G10 G1 heavy chain. Asterisk "*" indicates the termination codon FIG. 50: Nucleotide and amino acid sequence of the coding region of Ch2G10 κ light chain. Asterisk "*" indicates the termination codon.

FIG. 51: Relative affinity of the 2G10, Ch2G10, Hu2G10-5 and Hu2G10-6 antibodies for Trop-2—ELISA assay. Binding of biotinylated mouse 2G10 antibody to rhTrop-2 was analyzed in the presence of various concentrations of unlabelled competitor antibody (Ch2G10, Hu2G10-5 or Hu2G10-6). The graph shows the absorbance values (Y-axis) for each competitor antibody concentration tested (X-axis). The IC50 values were calculated using GraphPad Prism.

Figure 52:
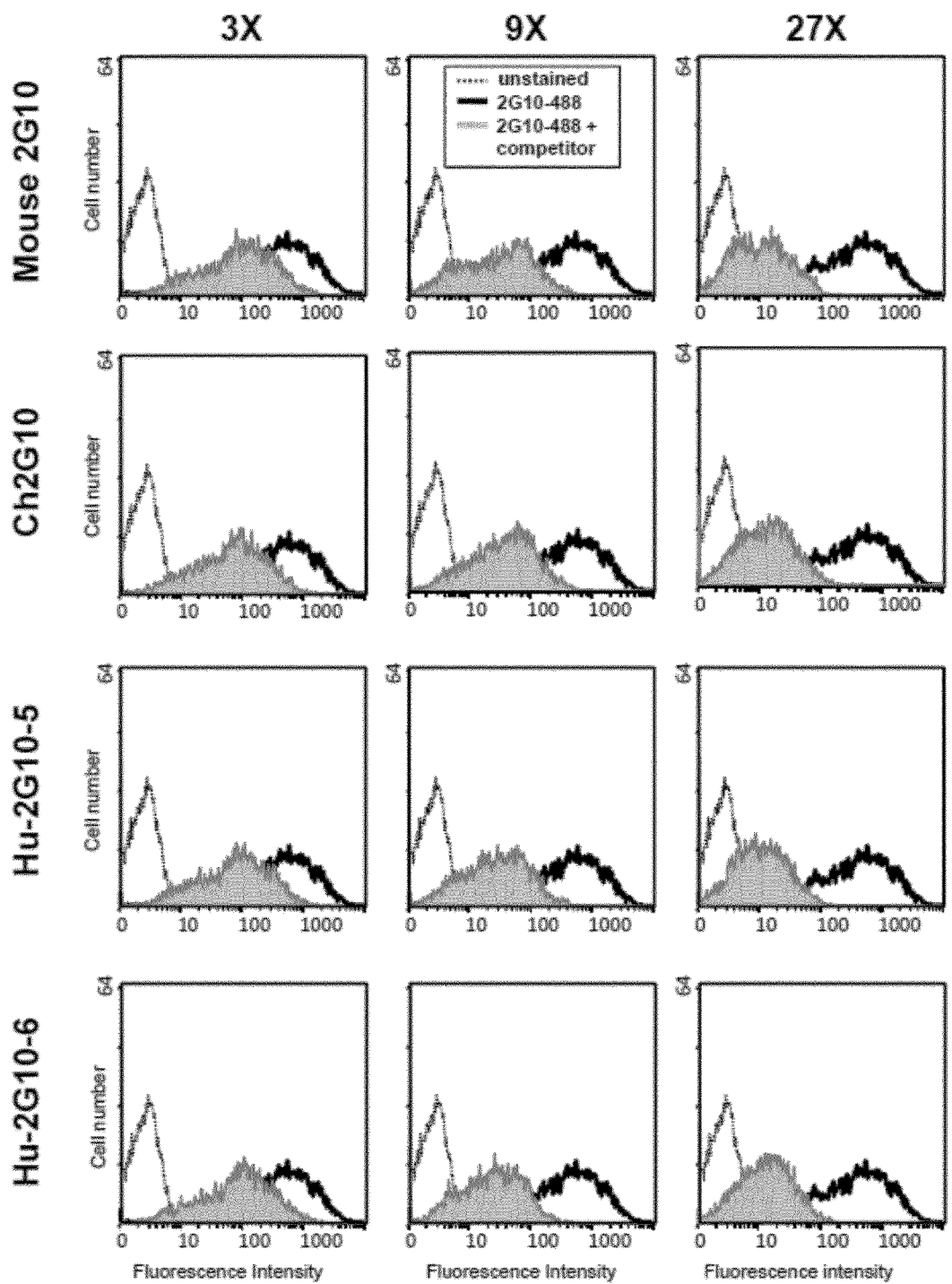

FIG. 52: Relative affinity of the 2G10, Ch2G10, Hu2G10-5 and Hu2G10-6 antibodies for native transfected Trop-2—Flow citometry analysis. Murine MTE 4-14 (Naquet, Lepesant et al. 1989)stably tranfected with Trop-2 were incubated with 0.3 μg of 2G10 antibody conjugated to Alexa 488 (2G10-488) either alone (thick line) or pre-mixed with 0.9 μg (3×, left), 2.7 μg (9×; middle) or 8.1 μg (27×, o right) of unlabelled 2G10 competitor (gray profile), as indicated. The dotted line corresponds to the unstained negative control.

Figure 53:
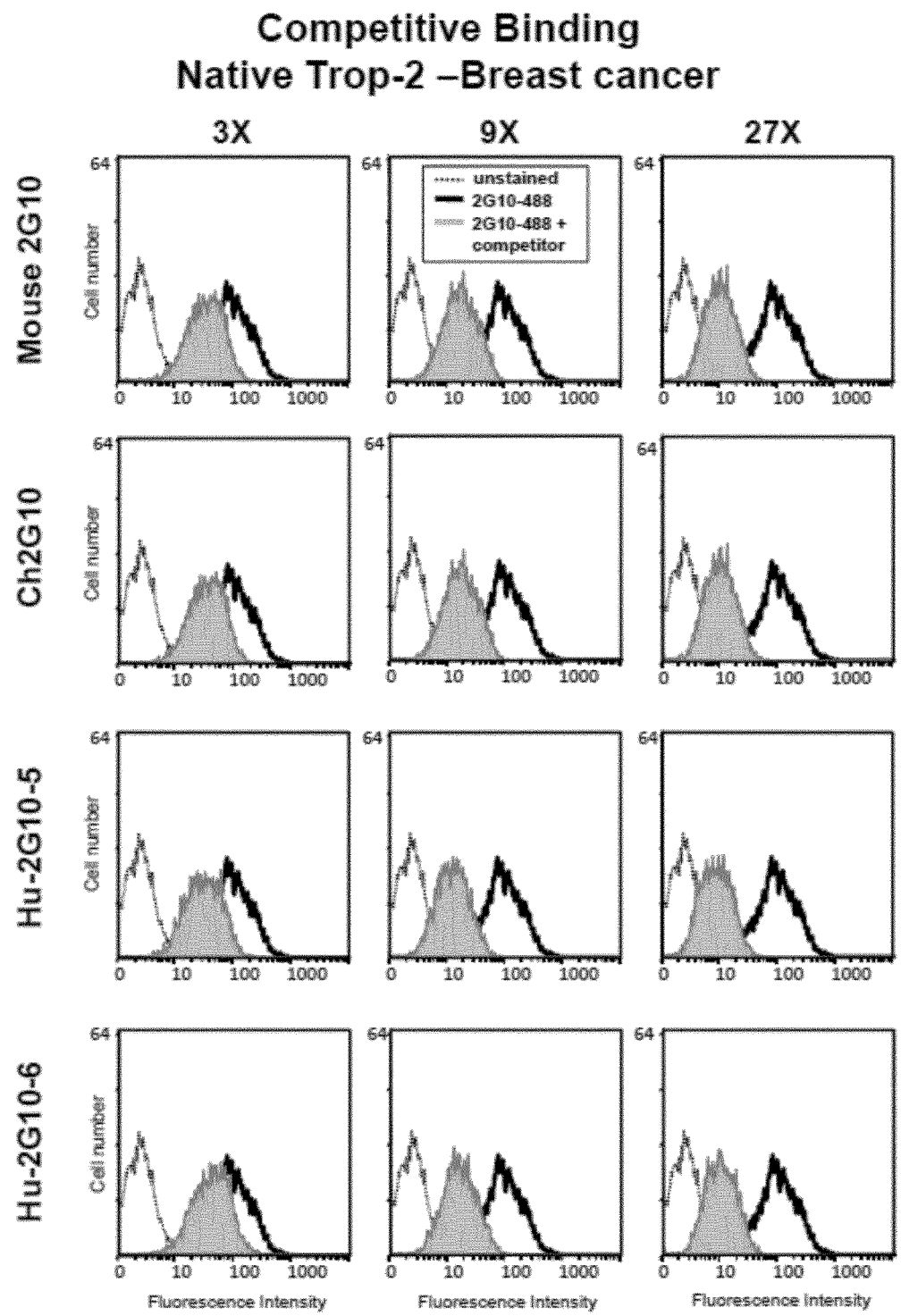

FIG. 53: Relative affinity of the2G10, Ch2G10, Hu2G10-5 and Hu2G10-6 antibodies for native endogenous Trop-2—Flow cytometry analysis. Human breast cancer MCF7 cells, which are positive for Trop-2, were incubated with 0.3 μg of Alexa-488 conjugated 2G10antibody (2G10-488) either alone (thick line) or pre-mixed with 0.9 μg (3X, left), 2.7 μg (9×; middle) or 8.1 μg (27×, right) of unlabelled competitor antibody (gray profile) as indicated. The dotted line corresponds to the unlabelled negative control.

Figure 54:
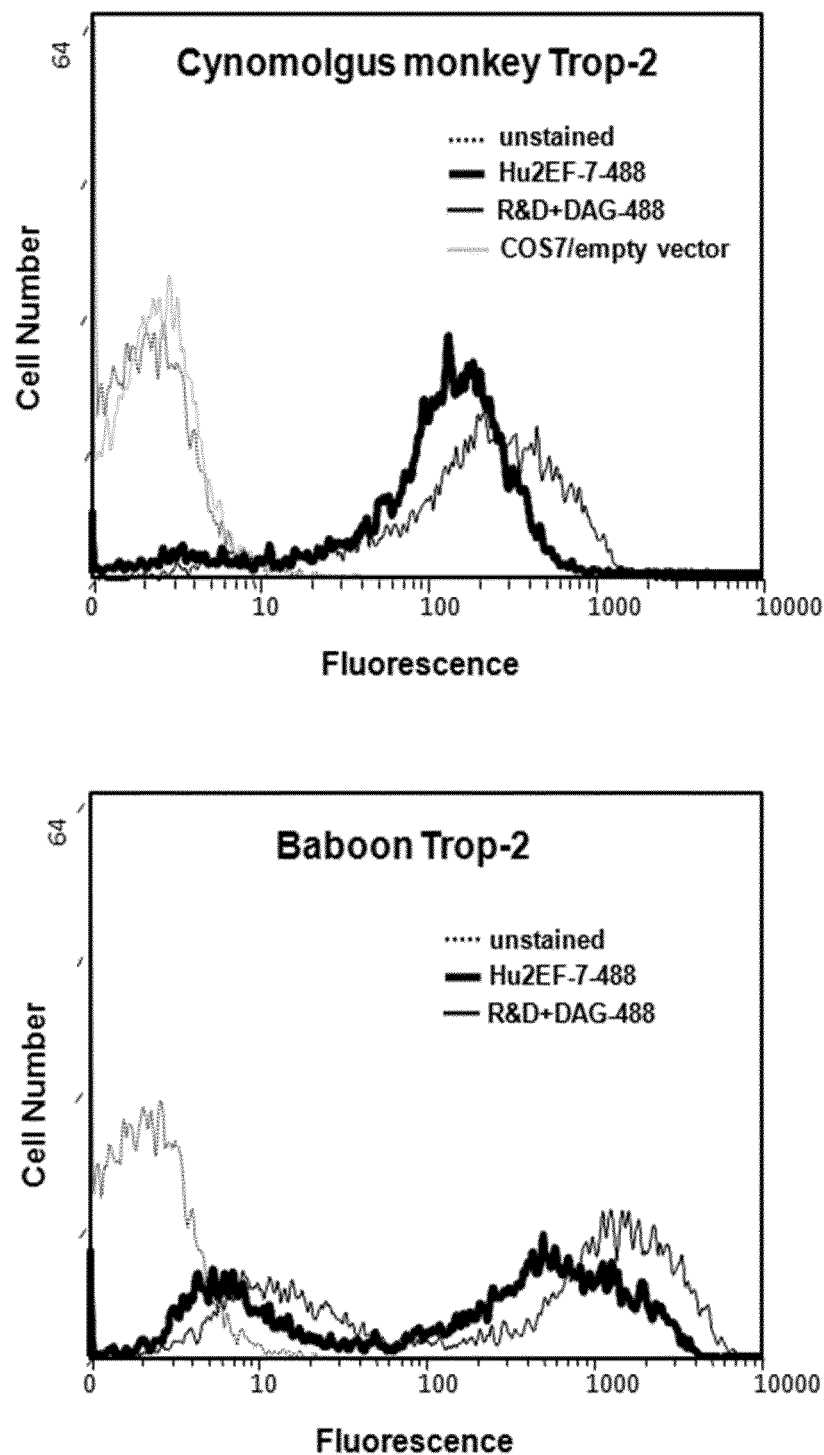

FIG. 54: Hu2EF-7 binds to monkey Trop-2. Flow-sorted COS-7 transfectants expressing the Trop-2 antigen from different monkey species as indicated were stained with the Hu2EF-7 MAb labelled with Alexa-488. Binding specificity was confirmed by the absence of fluorescence signal for negative control mock-transfected cells (top panel). The AF650 anti-Trop-2 polyclonal antibody (pAb) (R&D) revealed with Alexa Fluor-488 donkey anti-goat (DAG) IgG was used as positive control.

FIG. 55: Hu2G10-5 binds to monkey Trop-2. Flow-sorted COS-7 transfectants expressing the Trop-2 antigen from different monkey species as indicated were stained with the Hu2G10-5 MAb labelled with Alexa-488. Binding specificity was confirmed by the absence of fluorescence signal for negative control mock-transfected cells (top panel). The AF650 anti-Trop-2 pAb (R&D) revealed with a donkey-anti-goat (DAG) secondary antibody labelled with Alexa-488 was used as positive control.

Figure 56:
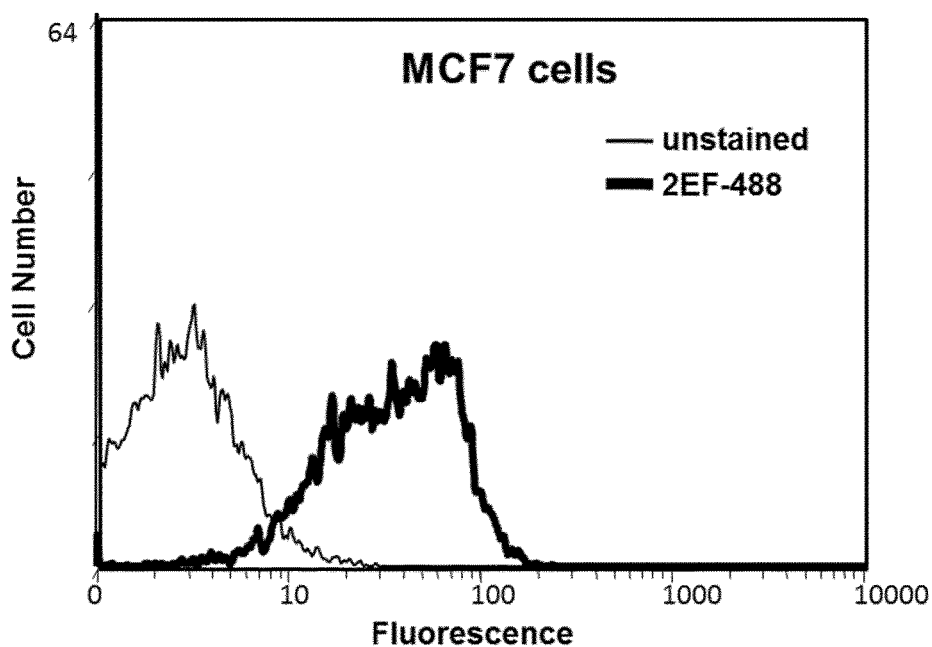

FIG. 56: Trop-2 expression in MCF-7 cells as assesses with the 2EF MAb. Flow cytometry analysis. Staining was performed with the 2EF antibody labeled with Alexa-488.

Figure 57:
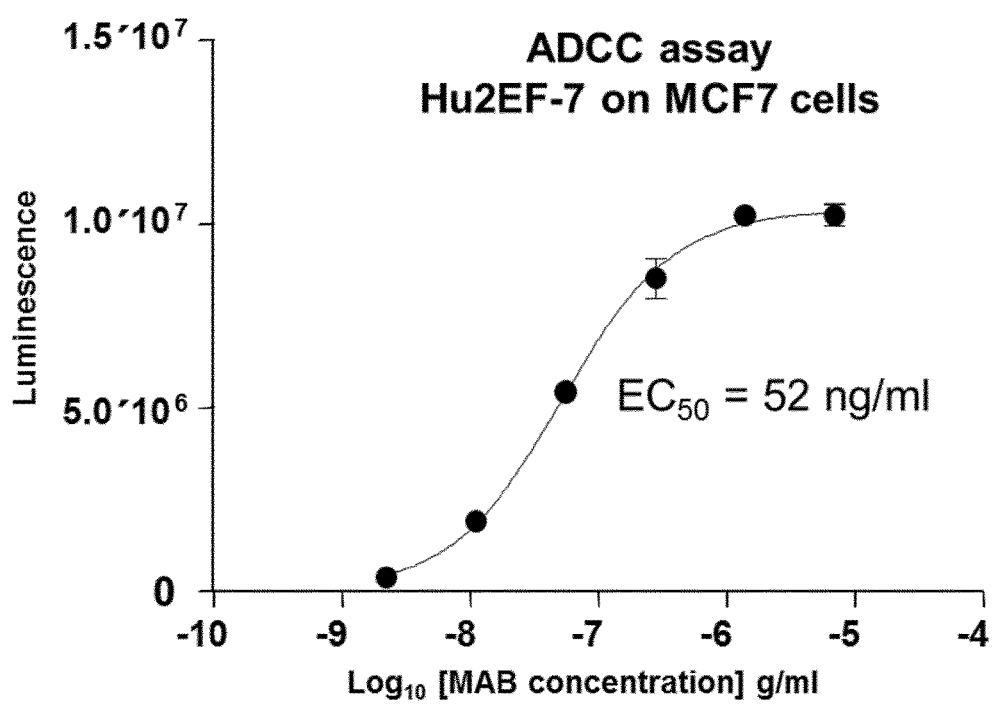

FIG. 57: ADCC response to Hu2EF-7 MAb. MCF-7 target cells were incubated with serial dilutions of the Hu2EF-7 MAb followed by addition of modified Jurkat effector cells (Promega). The E:T ratio was 6:1. After 17 hours of induction at 37° C., Bio-Glo™ Luciferase Assay Reagent (Promega) was added and luminescence was determined using a luminometer. Three replicates were performed for each data point. Data were fitted to a 4 parameter logistic (4PL) non linear regression model to obtain the dose-response curve and the $EC_{50}$ was calculated using GraphPad Prism software. Error bars: ±SEM.

Figure 58:
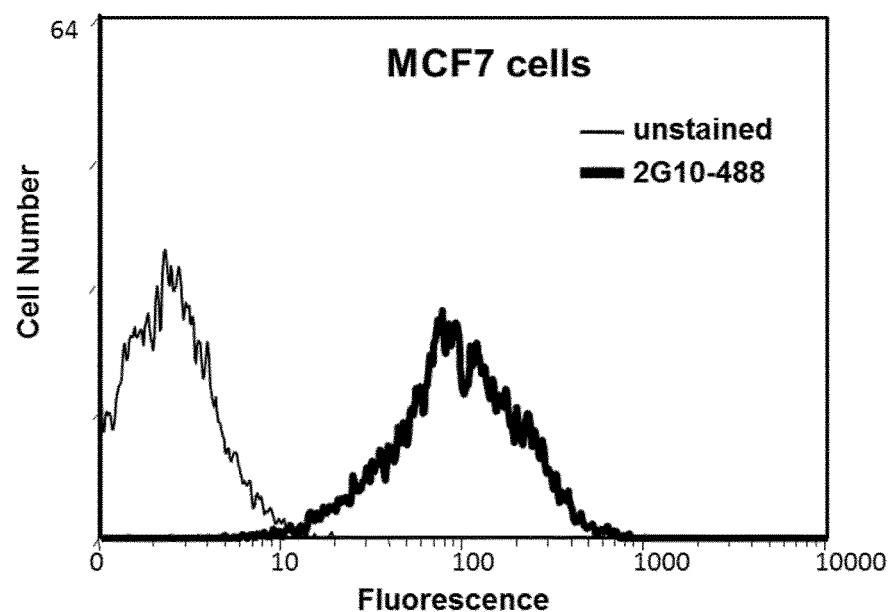

FIG. 58: Trop-2 expression in MCF-7 cells as assessed with the 2G10 MAb. Flow cytometry analysis. Staining was performed with the 2G10 antibody labeled with Alexa-488.

Figure 59:
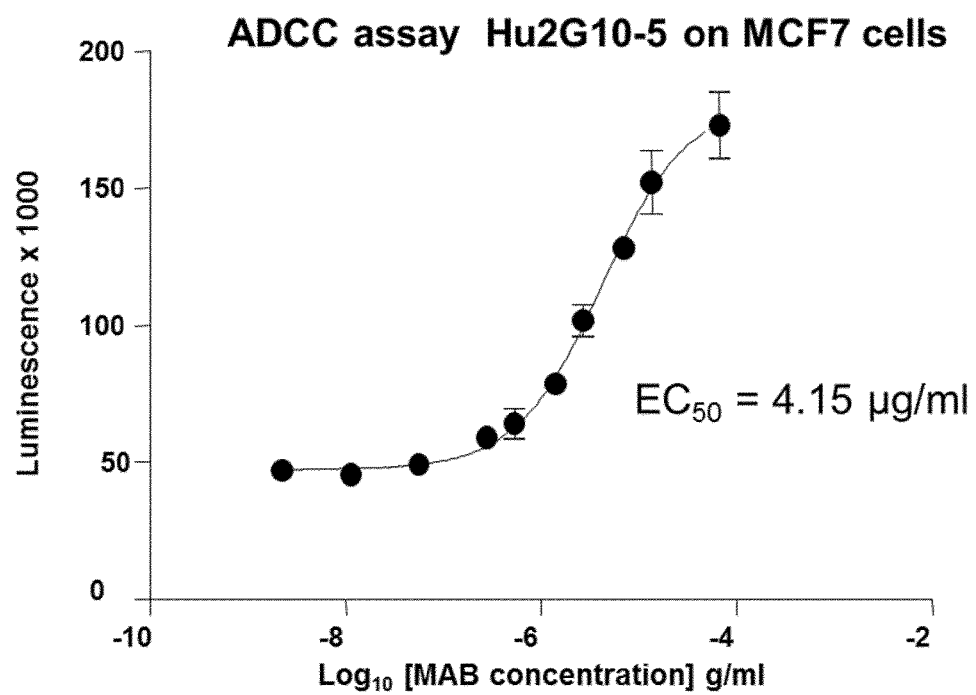

FIG. 59: ADCC response to Hu2G10-5 MAb. MCF-7 target cells were incubated with serial dilutions of the Hu2G10-5 MAb followed by addition of modified Jurkat effector cells. The E:T ratio was 3:1. After 17 hours of induction at 37° C., Bio-Glo™ Luciferase Assay Reagent (Promega) was added and luminescence was determined using a luminometer. Three replicates were performed for each data point. Data were fitted to a 4 parameter logistic (4PL) non linear regression model to obtain the dose-response curve and the $EC_{50}$ was calculated using GraphPad Prism software. Error bars: ±SEM.

Figure 60:
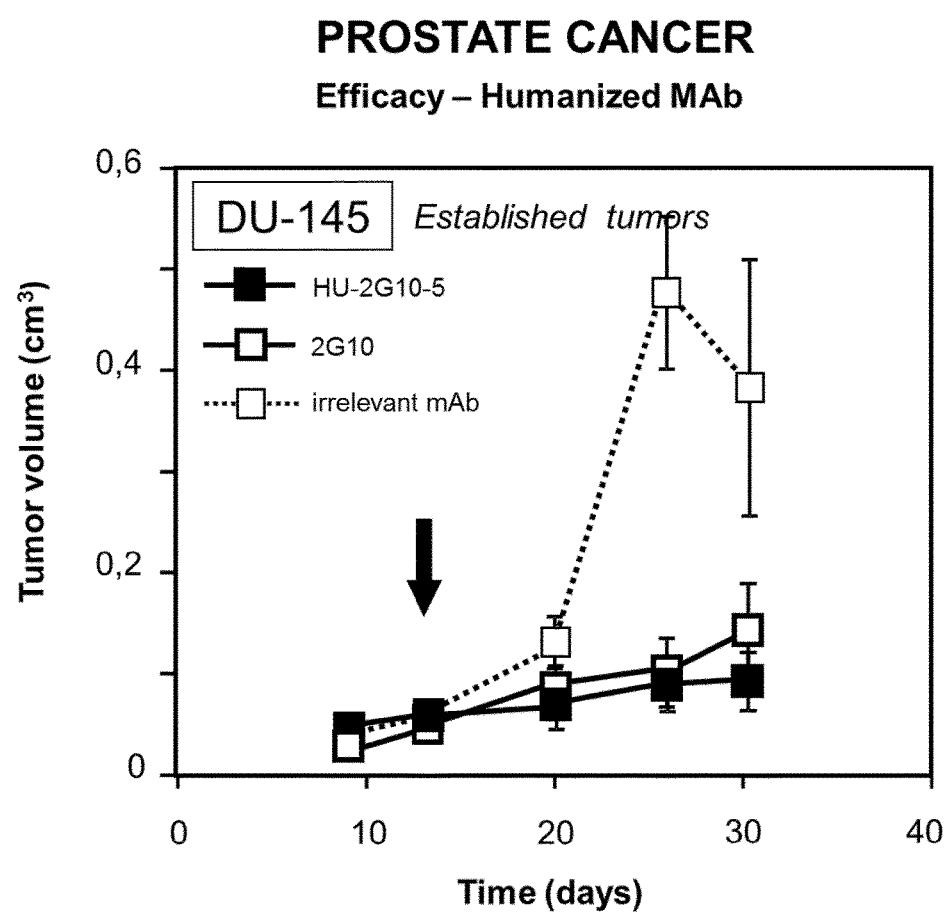

FIG. 60: In vivo efficacy. Inhibition of the growth of the DU-145 prostate cancer cell line as established, already growing tumors by treatment with the mouse 2G10 MAb or the humanized Hu2G10-5 MAb. Tumors treated with an antibody with irrelevant specificity (anti-dansyl: open squares) correspond to dotted lines. Each animal was injected IP with 800 μg purified antibodyonce a week. The vertical arrow indicates the first treatment. Error bars: ±SEM.

KEY TO SEQUENCE LISTING

SEQ ID NO:1 aminoacid sequence of the first heavy-chain CDR (CDRH1) of the 2EF antibody.
SEQ ID NO:2 aminoacid sequence of the second heavy-chain CDR (CDRH2) of the 2EF antibody.
SEQ ID NO:3 aminoacid sequence of the third heavy-chain CDR (CDRH3) of the 2EF antibody.
SEQ ID NO:4 aminoacid sequence of the first light-chain CDR (CDRL1) of the 2EF antibody.
SEQ ID NO:5 aminoacid sequence of the second light-chain CDR (CDRL2) of the 2EF antibody.
SEQ ID NO:6 aminoacid sequence of the third light-chain CDR (CDRL3) of the 2EF antibody.
SEQ ID NO:7 aminoacid sequence of the first heavy-chain CDR (CDRH1) of the 2G10 antibody.
SEQ ID NO:8 aminoacid sequence of the second heavy-chain CDR (CDRH2) of the 2G10antibody.
SEQ ID NO:9 aminoacid sequence of the third heavy-chain CDR (CDRH3) of the 2G10 antibody.
SEQ ID NO:10 aminoacid sequence of the first light-chain CDR (CDRL1) of the 2G10 antibody.
SEQ ID NO:11 aminoacid sequence of the second light-chain CDR (CDRL2) of the 2G10 antibody.
SEQ ID NO:12 aminoacid sequence of the third light-chain CDR (CDRL3) of the 2G10 antibody.
SEQ ID NO:13 nucleotide sequence of the VH of the chimeric Ch2EF antibody.
SEQ ID NO:14 aminoacid sequence of the VH of the chimeric Ch2EF antibody.
SEQ ID NO:15 nucleotide sequence of the VL of the chimeric Ch2EF antibody.
SEQ ID NO:16 aminoacid sequence of the VL of the chimeric Ch2EF antibody.
SEQ ID NO:17 nucleotide sequence of the VH of the chimeric Ch2G10 antibody.
SEQ ID NO:18 aminoacid sequence of the VH of the chimeric Ch2G10 antibody.
SEQ ID NO:19 nucleotide sequence of the VL of the chimeric Ch2G10 antibody.
SEQ ID NO:20 aminoacid sequence of the VL of the chimeric Ch2G10 antibody.
SEQ ID NO:21 nucleotide sequence of the VH version 4 (VH4) of the humanized Hu2EF antibody.
SEQ ID NO:22 aminoacid sequence of the VH version 4 (VH4) of the humanized Hu2EF antibody.
SEQ ID NO:23 nucleotide sequence of the VH version 5 (VH5) of the humanized Hu2EF antibody.
SEQ ID NO:24 aminoacid sequence of the VH version 5 (VH5) of the humanized Hu2EF antibody.
SEQ ID NO:25 nucleotide sequence of the VH version 7 (VH7) of the humanized Hu2EF antibody.
SEQ ID NO:26 aminoacid sequence of the VH version 7 (VH7) of the humanized Hu2EF antibody.
SEQ ID NO:27 nucleotide sequence of the VL version 1 (VL1) of the humanized Hu2EF antibody.
SEQ ID NO:28 aminoacid sequence of the VL version 1 (VL1) of the humanized Hu2EF antibody.
SEQ ID NO:29 nucleotide sequence of the VL version 2 (VL2) of the humanized Hu2EF antibody
SEQ ID NO:30 aminoacid sequence of the VL version 2 (VL2) of the humanized Hu2EF antibody.
SEQ ID NO:31 nucleotide sequence of the VH version 1 (VH1) of the humanized Hu2G10 antibody.
SEQ ID NO:32 aminoacid sequence of the VH version 1 (VH1) of the humanized Hu2G10 antibody.
SEQ ID NO:33 nucleotide sequence of the VH version 2 (VH2) of the humanized Hu2G10 antibody.
SEQ ID NO:34 aminoacid sequence of the VH version 2 (VH2) of the humanized Hu2G10 antibody.
SEQ ID NO:35 nucleotide sequence of the VL version 1 (VL1) of the humanized Hu2G10 antibody.
SEQ ID NO:36 aminoacid sequence of the VL version 1 (VL1) of the humanized Hu2G10 antibody.
SEQ ID NO:37 nucleotide sequence of the VL version 2 (VL2) of the humanized Hu2G10 antibody.
SEQ ID NO:38 aminoacid sequence of the VL version 2 (VL2) of the humanized Hu2G10 antibody.
SEQ ID NO:39 nucleotide sequence of the VL version 3 (VL3) of the humanized Hu2G10 antibody.
SEQ ID NO:40 aminoacid sequence of the VL version 3 (VL3) of the humanized Hu2G10 antibody.
SEQ ID NO:41 nucleotide sequence of the coding region of the gamma-1 heavy chain of the humanized Hu2EF-7 antibody.
SEQ ID NO:42 aminoacid sequence of the gamma-1 heavy chain of the humanized Hu2EF-7 antibody.
SEQ ID NO:43 nucleotide sequence of the coding region of the kappa light chain of the humanized Hu2EF-7 antibody.
SEQ ID NO:44 aminoacid sequence of the kappa light chain of the humanized Hu2EF-7 antibody.
SEQ ID NO:45 nucleotide sequence of the coding region of the gamma-1 heavy chain of the humanized Hu2G10-5 antibody.
SEQ ID NO:46 aminoacid sequence of the gamma-1 heavy chain of the humanized Hu2G10-5 antibody.
SEQ ID NO:47 nucleotide sequence of the coding region of the kappa light chain of the humanized Hu2G10-5 e Hu2G10-6 antibodies.
SEQ ID NO:48 aminoacid sequence of the kappa light chain of the humanized Hu2G10-5 e Hu2G10-6 antibodies.
SEQ ID NO:49 nucleotide sequence of the coding region of the gamma-1 heavy chain of the humanized Hu2G10-6 antibody.
SEQ ID NO:50 aminoacid sequence of the gamma-1 heavy chain of the humanized Hu2G10-6 antibody.
SEQ ID NO:51 forward primer for PCR amplification of 2EF VH from mouse 2EF cDNA.
SEQ ID NO:52 reverse primer for PCR amplification of 2EF VH from mouse 2EF cDNA.
SEQ ID NO:53 reverse primer for PCR amplification of 2EF VH from mouse 2EF cDNA.

SEQ ID NO:54 forward primer for PCR amplification of 2EF VL from mouse 2EF cDNA.
SEQ ID NO:55 reverse primer for PCR amplification of 2EF and 2G10 VL from mouse 2EF and 2G10 cDNAs.
SEQ ID NO:56 reverse primer for PCR amplification of 2EF VL from mouse 2EF cDNA.
SEQ ID NO:57 synthetic gene encoding the VH of the chimeric Ch2EF antibody.
SEQ ID NO:58 synthetic gene encoding the VL of the chimeric Ch2EF antibody.
SEQ ID NO:59 synthetic gene encoding the VH4 of the humanized Hu2EF antibody.
SEQ ID NO:60 synthetic gene encoding the VH5 of the humanized Hu2EF antibody.
SEQ ID NO:61 synthetic gene encoding the VL1 of the humanized Hu2EF antibody.
SEQ ID NO:62 forward primer CMV2 for PCR amplification and sequencing of the coding region of the gamma-1 heavy chain and the kappa light chain of the Ch2EF, Hu2EF-4, Hu2EF-5, Hu2EF-7, Ch2G10, Hu2G10-5 and Hu2G10-6 antibodies in the corresponding expression vectors.
SEQ ID NO:63 reverse primer JNT026 for PCR amplification and sequencing of the coding region of the kappa light chain of the Ch2EF, Hu2EF-4, Hu2EF-5, Hu2EF-7, Ch2G10, Hu2G10-5 and Hu2G10-6 antibodies in the corresponding expression vectors.
SEQ ID NO:64 primer JNT082 for sequencing of gamma-1 heavy chain of the Ch2EF, Hu2EF-4, Hu2EF-5, Hu2EF-7, Ch2G10, Hu2G10-5 and Hu2G10-6 antibodies.
SEQ ID NO:65 primer JNT097 for sequencing of gamma-1 heavy chain of the Ch2EF, Hu2EF-4, Hu2EF-5, Hu2EF-7, Ch2G10, Hu2G10-5 and Hu2G10-6 antibodies.
SEQ ID NO:66 reverse primer JNT098 for PCR amplification and sequencing of the coding region of the gamma-1 heavy chain of the Ch2EF, Hu2EF-4, Hu2EF-5, Hu2EF-7, Ch2G10, Hu2G10-5 and Hu2G10-6 antibodies in the corresponding expression vectors.
SEQ ID NO:67 synthetic gene encoding the VH7 of the humanized Hu2EF-7 antibody.
SEQ ID NO:68 synthetic gene encoding the VL2 of the humanized Hu2EF-7 antibody.
SEQ ID NO:69 reverse primer MCG2A for PCR amplification of 2G10 VH from mouse 2G10 cDNA.
SEQ ID NO:70 forward primer 2G10-L5 for PCR amplification of 2G10 VL from mouse 2G10 cDNA.
SEQ ID NO:71 reverse primer 2G10-L3 for PCR amplification of 2G10 VL from mouse 2G10 cDNA.
SEQ ID NO:72 synthetic gene encoding the VH of the chimeric Ch2G10 antibody.
SEQ ID NO:73 forward primer for PCR amplification of VH from mouse 2. G10 cDNA.
SEQ ID NO:74 reverse primer for PCR amplification of VH from mouse 2G10 cDNA.
SEQ ID NO:75 synthetic gene encoding the VL of the chimeric Ch2G10 antibody.
SEQ ID NO:76 forward primer for PCR amplification of VL from mouse 2G10 cDNA.
SEQ ID NO:77 reverse primer for PCR amplification of VL from mouse 2G10 cDNA.
SEQ ID NO:78 synthetic gene encoding the VH1 of the humanized Hu2G10 antibody.
SEQ ID NO:79 synthetic gene encoding the VH2 of the humanized Hu2G10 antibody.
SEQ ID NO:80 synthetic gene encoding the VL1 of the humanized Hu2G10 antibody.
SEQ ID NO:81 synthetic gene encoding the VL2 of the humanized Hu2G10 antibody.
SEQ ID NO:82 synthetic gene encoding the VL3 of the humanized Hu2G10 antibody.
SEQ ID NO:83 nucleotide sequence of the coding region of the gamma-1 heavy chain of the chimeric Ch2G10 antibody.
SEQ ID NO:84 aminoacid sequence of the gamma-1 heavy chain of the chimeric Ch2G10 antibody.
SEQ ID NO:85 nucleotide sequence of the coding region of the kappa light chain of the chimeric Ch2G10 antibody.
SEQ ID NO:86 aminoacid sequence of the kappa light chain of the chimeric Ch2G10 antibody.
SEQ ID NO: 87 amino acid sequence of human Trop-2.
SEQ ID NO: 88 amino acid sequence of the mature form of the human VH M17751.1 as shown in FIG. 23.
SEQ ID NO: 89 amino acid sequence of the mature form of the human VH L02325.1 as shown in FIG. 24.
SEQ ID NO: 90 amino acid sequence of the mature form of the human VH X65888.1 as shown in FIG. 41.
SEQ ID NO: 91 amino acid sequence of the mature form of the human VL Z46622.1 as shown in FIG. 25.
SEQ ID NO: 92 amino acid sequence of the mature form of the human VL AY043146.1 as shown in FIG. 42.
SEQ ID NO: 93 amino acid sequence of the mature form of the human VH M17751.1.
SEQ ID NO: 94 amino acid sequence of the mature form of the human VH L02325.1.
SEQ ID NO: 95 amino acid sequence of the mature form of the human VH X65888.1.
SEQ ID NO: 96 amino acid sequence of the mature form of the human VL Z46622.1.
SEQ ID NO: 97 amino acid sequence of the mature form of the human VL AY043146.1.

EXAMPLES

Example 1

Material and Methods
1. Construction of Chimeric 2EF IgG1/κ Antibody

Mouse 2EF hybridoma cells (PD 08021, AID-ICLC Genoa) were grown in RPMI-1640 medium containing 20% fetal bovine serum (FBS; HyClone, Logan, UT) at 37° C. in a 7.5% $CO_2$ incubator. Total RNA was extracted from approximately $10^7$ hybridoma cells using TRIzol reagent (Life Technologies, Carlsbad, Calif.) according to the supplier's protocol. Oligo dT-primed cDNA was synthesized using the SMARTer RACE cDNA Amplification Kit (Clontech, Mountain View, Calif.) following the supplier's protocol. The VH and VL cDNAs were amplified by polymerase chain reaction (PCR) with Phusion DNA polymerase (New England Biolabs, Beverly, Mass.) and the following primers:

```
forward primers for 2EF VH:
Universal Primer A Mix provided in the SMARTer
RACE cDNA Amplification Kit
2EF-H5:
                                        (SEQ ID NO: 51)
5'-TACACCTTCACTAACTACTGG-3' reverse primers for 2EF VH:
2EF-H3:
                                        (SEQ ID NO: 52)
5'-CCCAGTTCCTCTGCACAG-3'
```

```
                                         -continued
MCG2b:
                                                            (SEQ ID NO: 53)
5'-GCCAGTGGATAGACTGATGG-3' forward primersfor 2EF VL:
Universal Primer A Mix provided in the SMARTer
RACE cDNA Amplification Kit
2EF-L5:
                                                            (SEQ ID NO: 54)
5'-AGCCAAAGTGTCAGTACATC-3' reverse primersfor 2EF VL:
JNT319:
                                                            (SEQ ID NO: 55)
5'-CTCCCTCTAACACTCATTCCTGTTGAAGC-3'

2EF-L3:
                                                            (SEQ ID NO: 56)
5'-GAATCTCCCGACTGTGCTG-3'
```

The amplified VH and VL cDNAs were gel-purified using the NucleoSpin Extraction II Kit (Macherey-Nagel, Bethlehem, Pa.) and cloned into the pCR4Blunt-TOPO vector (Life Technologies) for sequence determination. DNA sequencing of the variable regions was carried out at Tocore (Menlo Park, Calif.). Several heavy and light chain clones were sequenced and unique sequences homologous to typical mouse heavy and light chain variable regions were identified.

A gene encoding 2EF VH was synthesized as an exon including a splice donor signal at the 3'end of the coding region, a SpeI site at the 5' end of the fragment, and a HindIII site at the 3' end of the fragment (SEQ ID NO: 57; FIG. 20).

Likewise, a gene encoding 2EF VL was synthesized as an exon including a splice donor signal at the 3' end of the coding region, an NheI site at the 5' end of the fragment, and an EcoRI site at the 3' end of the fragment (SEQ ID NO:58; FIG. 21). The splice donor signals of the 2EF VH and VL exons were derived from the mouse germline JH3 and Jκ2 sequences, respectively. The synthesis of the 2EF VH and VL genes was conducted by GenScript USA (Piscataway, N.J.).

The synthesized 2EF VH and VL exons were cloned between SpeI and HindIII sites (for VH) or NheI and EcoRI sites (for VL) of a mammalian expression vector carrying human κ and G1 constant regions for production of chimeric 2EF IgG1/κ antibody (Ch2EF). The schematic structure of the resulting expression vector, pCh2EF, is shown in FIG. 22. The pCh2EF vector carries the Escherichia coligpt gene for selection in mammalian cells.

2. General Scheme of 2EF Antibody Humanization

Designing of humanized 2EF VH and VL amino acid sequences was carried out as follows. First, a three-dimensional molecular model of the mouse 2EF variable regions was constructed using specifically developed approaches. Next, the framework amino acid residues important for the formation of the CDR structure were identified using the molecular model. In parallel, cDNA-derived human VH and VL amino acid sequences with high homology to 2EF VH and VL, respectively, were selected. Lastly, CDR sequences together with framework amino acid residues important for maintaining the CDR structure were grafted from 2EF VH and VL into the corresponding selected human framework sequences.

3. Design of Humanized 2EF VH and VL

Human VH sequences homologous to the mouse 2EF VH frameworks were searched for within the GenBank database, and the VH sequence encoded by the human cDNA with NCBI Accession number M17751.1 was chosen as an acceptor for humanization. The CDR sequences of 2EF VH (SEQ ID NO:1-3) were first transferred to the corresponding positions of M17751.1 VH. Next, at framework positions 48, 68, 70 and 72 (numbering starts from the first aminoacid of VH mature form, after signal peptide removal), where the three-dimensional models suggested significant contact with the CDRs, human amino acid residues were substituted by the corresponding mouse residues. In addition, an amino acid residue at position 44, which is judged to be important for proper formation of the VH-VL interface, thus affecting the structure of the antigen binding site, was replaced by the corresponding residue in the mouse 2EF VH. The amino acid sequence of the resulting humanized VH, Hu2EF VH4 (SEQ ID NO:22), alongside with the 2EF (SEQ ID NO:14) and M17751.1 VH sequences, is shown in FIG. 23.

In addition to Hu2EF VH4, another humanized VH (Hu2EF VH5) was designed using the VH sequence encoded by the human cDNA with NCBI Accession number: L02325.1. The CDR sequences of 2EF VH were first transferred to the corresponding positions of L02325.1 VH. Next, at framework positions 48, 68, 70 and 72, where the three-dimensional model of the 2EF variable regions suggested significant contact with the CDRs, human amino acid residues were substituted by the corresponding mouse residues. The amino acid sequence of the resulting humanized VH, Hu2EF VH5 (SEQ ID NO:24), alongside with the 2EF and L02325.1 VH sequences, is shown in FIG. 24.

Based on the homology search with the 2EF VL framework sequences, the human Vκ region encoded by the cDNA with NCBI Accession number: Z46622.1was chosen as an acceptor for humanization. CDR sequences of 2EF VL (SEQ ID NO:4-6) were first transferred to the corresponding positions of Z46622.1 VL. Next, at position 53, which was indicated as making significant contact with the CDRs, the human amino acid residue in Z46622.1 was substituted with the corresponding murine residue of 2EF VL. The amino acid sequence of the resulting humanized VL, Hu2EF VL1 (SEQ ID NO:28), is shown in FIG. 25 alongside with 2EF and Z46622.1 VL sequences.

4. Construction of Humanized 2EF VH and VL genes

Genes encoding each of the humanized VH4-Hu2EF (SEQ ID NO: 59; FIG. 26), VH5-Hu2EF (SEQ ID NO: 60; FIG. 27) and VL1-Hu2EF (SEQ ID NO: 61; FIG. 28) sequences were designed as exons including a signal peptide, a splice donor signal, and appropriate restriction enzyme sites for subsequent cloning into a mammalian expression vector. The signal peptide sequence and splice donor signal of each gene were derived from the corresponding mouse 2EF VH or VL gene in pCh2EF.

The VL1-Hu2EF gene was synthesized by GenScript USA. VH4-Hu2EF e VH5-Hu2EF were constructed by custom synthesis at GenScript USA followed by modification using site-directed mutagenesis to remove criptic signal sequences. After digestion with SpeI and HindIII (for VH) or NheI and EcoRI (for VL), these genes were subcloned into corresponding sites in a mammalian expression vector for production of humanized IgG1/κ (FIG. 22). As a result, two expression vectors were constructed. The first expression vector, pHu2EF-4, expresses the humanized Hu2EF-4 antibody, which contains IgG1/κ VH4-Hu2EF and VL1-Hu2EF. The second vector, pHu2EF-5, expresses the humanized Hu2EF-5 antibody, which contains VH5-Hu2EF and VL1-Hu2EF.

5. Generation of NS0 stable Transfectants Producing Ch2EF, Hu2EF-4 and Hu2EF-5

To obtain cell lines stably producing Ch2EF, Hu2EF-4 and Hu2EF-5, the expression vectors pCh2EF, pHu2EF-4 and pHu2EF-5, respectively, were introduced into the chromosome of a mouse myeloma cell line NS0 (European Collection of Animal Cell Cultures, Salisbury, Wiltshire, UK). NS0 cells were grown in DME medium containing 10% FBS at 37° C. in a 7.5% $CO_2$ incubator. Stable transfection into NS0 was carried out by electroporation. Before transfection, each expression vector was linearized using FspI. Approximately $10^7$ cells were transfected with 20 µg of linearized plasmid, suspended in DME medium containing 10% FBS, and plated into several 96-well plates. After 48 hr, selection medium(DME medium containing 10% FBS and HT media supplement-Sigma-Aldrich, 0.25 mg/ml xanthine and 1 µg/ml mycophenolic acid) was applied. Approximately 10 days after the beginning of selection, culture supernatants were assayed for antibody production by sandwich ELISA. In a typical experiment, a microtiter plate (Cat. No. 655001, Greiner Bio One, Monroe, N.C.) was coated overnight at 4° C. with 100 µl/well of 1/2,000-diluted goat anti-human IgG Fcγ-chain-specific pAb (Sigma-Aldrich, St. Louis, Mo.) in PBS, washed with Wash Buffer (PBS containing 0.05% Tween 20), and blocked with 200 µl/well of Block Buffer (PBS containing 2% Skim Milk and 0.05% Tween 20) for 0.5 hr at room temperature. After washing with Wash Buffer, 100 µl/well of test samples appropriately diluted in ELISA Buffer (PBS containing 1% Skim Milk and 0.025% Tween 20) were applied to the ELISA plate. An appropriate human or humanized IgG1/κ monoclonal antibody was used as a standard. After incubating the ELISA plate for 1 hr at room temperature and washing with Wash Buffer, bound antibodies were detected using 100 µl/well of 1/2,000-diluted HRP-conjugated goat anti-human κ chain pAb (SouthernBiotech, Birmingham, Ala.). After incubating for 0.5 hr at room temperature and washing with Wash Buffer, color development was initiated by adding 100 µl/well of ABTS substrate (AMRESCO, Solon, Ohio) and stopped with 100 µl/well of 2% oxalic acid. Absorbance was read at 405 nm.

NS0 stable transfectants producing a high level of Ch2EF (NS0-Ch2EF 1E7), Hu2EF-4 (NS0-Hu2EF-4 1B9) and Hu2EF-5 (NS0-Hu2EF-5 1A11) were adapted to growth in serum-free media using Hybridoma SFM (Life Technologies). Frozen cell stocks of these NS0 stable transfectants were made in BamBanker (Cat #302-14681, WAKO Chemicals USA, Richmond, Va.) and stored in liquid nitrogen. These three NS0 stable transfectants were tested with the PCR Mycoplasma Detection Set (Takara Bio USA, Madison, Wis.) and found negative for the presence of mycoplasma.

The authenticity of heavy and light chains produced in NS0-Ch2EF 1E7, NS0-Hu2EF-4 1B9 and NS0-Hu2EF-5 1A11 cells was confirmed by cDNA sequencing. Total RNA was extracted from cells using TRIzol reagent (Life Technologies) and oligo dT-primed cDNA was synthesized using the ProtoScript M-MuLV First Strand cDNA Synthesis Kit (New England Biolabs) following supplier's protocols. The coding region of G1 heavy chain was amplified by PCR using CMV2 and JNT098 as primers and Phusion DNA polymerase. PCR fragments were gel-purified and subjected to sequencing with CMV2, JNT082, JNT097 and JNT098 as primers. Primer sequences are as follows:

```
CMV2
                                  (SEQ ID NO: 62)
5'-GAACCGTCAGATCGCCTGGAGAC-3'
```

```
JNT026
                                 ((SEQ ID NO: 63)
5'-TGAAAGATGAGCTGGAGGAC-3'

JNT082
                                  (SEQ ID NO: 64)
5'-CTTTCTTGTCCACCTTGGTG-3'

JNT097
                                  (SEQ ID NO: 65)
5'-GCTGTCCTACAGTCCTCA-3'

JNT098
                                  (SEQ ID NO: 66)
5'-ACGTGCCAAGCATCCTC-3'
```

Similarly, the coding region of κ light chain was amplified using CMV2 and JNT026. Gel-purified DNA fragments were subjected to sequencing with CMV2 and JNT026 as primers. The obtained nucleotide sequence of the coding region for each VH and VL of Ch2EF, Hu2EF-4 and Hu2EF-5 matched perfectly with the corresponding sequence in the pCh2EF, pHu2EF-4 or pHu2EF-5 vectors.

6. Purification of Mouse 2EF, Ch2EF, Hu2EF-4 and Hu2EF-5 Antibodies

Mouse 2EF hybridoma, and NS0-Ch2EF 1E7, NS0-Hu2EF-4 1B9 and NS0-Hu2EF-5 1A11 cells were expanded in Hybridoma SFM in roller bottles to the density of about $10^6$/ml, fed with $1/10^{th}$ volume of 60 mg/ml of Ultrafiltered Soy Hydrolysate (Irvine Scientific, Santa Ana, Calif.) dissolved in SFM4MAb media (HyClone), and grown further until the cell viability became less than 50%. After centrifugation and filtration, culture supernatant of each cell line was loaded onto a protein-A Sepharose column (HiTrapMabSelectSuRe, GE Healthcare, Piscataway, N.J.). The column was washed with PBS before the antibody was eluted with 0.1 M glycine-HCl (pH 3.0). After neutralization with 1 M Tris-HCl (pH 8), the buffer of eluted antibody was changed to PBS by dialysis. Antibody concentration was determined by measuring absorbance at 280 nm (1 mg/ml=1.4 OD). The yield was 12.9 mg for mouse 2EF, 1.95 mg for Ch2EF, 9.3 mg for Hu2EF-4 and 8.8 mg for Hu2EF-5, starting from 500 ml of culture supernatant.

Purified Ch2EF rapidly formed precipitates during storage in PBS at 4° C. This phenomenon was repeatedly observed with newly purified Ch2EF. No sign of precipitation has been noticed for mouse 2EF, Hu2EF-4 and Hu2EF-5. Ch2EF was therefore usable only right after purification as a control for testing the antigen binding of humanized 2EF antibodies 7. Antigen Binding of Hu2EF-4 and Hu2EF-5

Binding of purified Hu2EF-4 and Hu2EF-5 to the Trop-2 antigen was tested by ELISA. Mouse 2EF was used as a control. In a typical experiment, a microtiter plate was coated overnight at 4° C. with 100 µl/well of 1 µg/ml recombinant human Trop-2-Fc fusion protein (rhTrop2; Cat. #650-T2-100, R&D Systems, Minneapolis, Minn.) in 0.2 M sodium carbonate buffer (pH 9.4), washed with Wash Buffer, blocked with 200 µl/well of Block Buffer for 30 min at room temperature, and then washed with Wash Buffer. Purified test antibodies appropriately diluted in ELISA Buffer (starting at 5 µg/ml and serial 2-fold dilutions) were applied to wells at 100 µl/well and incubated for 60 min at room temperature. After washing with Wash Buffer, bound antibodies were detected using 100 µl/well of 1/2,000-diluted HRP-conjugated goat anti-human κ chain pAb (for Hu2EF-4 and Hu2EF-5) or goat anti-mouse κ chain pAb (for mouse 2EF). Color development and absorbance reading were carried out as described above. As shown in FIG. 29, the binding of Hu2EF-4 and Hu2EF-5 to Trop2 under these conditions was comparable to that of mouse 2EF.

Binding of Hu2EF-4 and Hu2EF-5 to Trop-2 was also analyzed by competitive ELISA. A microtiter plate was coated overnight at 4° C. with rhTrop2 as described above. Then, 100 µl/well of a mixture of a sub-saturating concentration (200 ng/ml) of biotinylated mouse 2EF and various concentrations of a purified competitor antibody (mouse 2EF, Hu2EF-4 and Hu2EF-5; starting from 2 µg/ml with serial 2-fold dilutions) in ELISA buffer was added for a 60 min incubation at room temperature. The ELISA plate was then washed with Wash Buffer, incubated with 100 µl of 1 µg/ml of streptavidin-conjugated HRP in ELISA Buffer for 30 min, and washed with Wash Buffer. Color development and absorbance reading were carried out as described above. Unexpectedly, as shown in FIG. 30, when compared to, both Hu2EF-4 and Hu2EF-5 competed poorly with the murine 2EF for binding to Trop-2 (compare the curves of the competitive binding of the humanized antibodies with the curve of the murine 2EF antibody).

The relative affinity of Hu2EF-4 e Hu2EF-5 for the native Trop-2 antigen was also analysed by means of in-vivo competitive binding measured by flow cytometry on live tumor cells that express surface Trop-2. About $3 \times 10^5$ human colon cancer Colo205 cells were incubated with 0.3 µg/ml of Alexa-488-labelled murine 2EF (2EF-488), either alone or in combination with increasing amounts (2.7 µg or 8.1 µg, 9× and 27× excess respectively)of unlabelled competitor antibody in 200 µl SM buffer (PBS with 10% FBS and 0,01% $NaN_3$). After 20 min at 4° C. cells were washed with 5 ml of SM and resuspended in 500 µl di SM with 0.5 µg/ml propidioiodide to discriminate dead cells). Fluorescence was then analysed by flow cytometry (FACScalibur, FACScan, Becton Dickinson, Sunnyvale, Calif.) as previously described (Alberti, Nutini et al. 1994) (FIG. 31). Also in this experiment the humanized Hu2EF-5 antibody showed a significant loss of affinity for Trop-2 (compare top panels with middle panels in FIG. 31). Simila results were obtained for the Hu2EF-4 antibody.

These data revealed that the humanization procedure that generated the Hu2EF-4 and Hu2EF-5 antibodies caused a significant loss of affinity for the Trop-2 antigen, at variance with what was expected.

Binding of humanized Hu2EF-4 e Hu2EF-5 antibodies to Trop-2 was further analyzed by ELISA with a microtiter plate coated with 100 µl/well of a solution of 0.1 µg/ml of rhTrop2. All other procedures were carried out as described above. In this experiment, Ch2EF and Hu2EF antibodies were used that were transiently expressed in the human embryonic kidney cell line HEK293 transfected by the Lipofectamine 2000 method (Life Technologies). In FIG. 32 the result of the binding of Ch2EF and Hu2EF-5 is shown. When the plate was coated with a lower amount of antigen (0.1 µg/ml rhTrop2 instead of 1 µg/ml), Hu2EF-5 bound to Trop-2 more weakly than Ch2EF.

8. Modification of Humanized 2EF Antibodies

The loss of affinity for Trop-2 that was detected for the humanized Hu2EF-4 e Hu2EF-5 antibodies called for a more in-depth analysis of the three-dimensional model of the 2EF variable regions, by including aminoacid residues and structural determinants that had not been considered in the course of the first study. These analyses suggested the possibility that aminoacid residues in non-canonical positions could unexpectedly influence the structure of the antigen binding site. In particular this was indicated for positions 11, 38, 40 e 43 in the mature VH and positions 4 and 104 in the mature VL of the 2EF antibody. For each of these positions the amino acid residue of the human acceptor sequence was substituted by the corresponding mouse residue by site-directed mutagenesis (see FIG. 23 and FIG. 25 for an overview). The resultant humanized Hu2EF variants have the VH and VL genes carrying one of the following amino acid substitutions: Val to Leu at position 11 in VH (VH-V11L), Arg to Lys at position 38 in VH (VH-R38K), Ala to Arg at position 40 in VH (VH-A4OR), Gln to His at position 43 in VH (VH-Q43H), Met to Leu at position 4 in VL (VL-M4L), and Gln to Gly at position104 in VL (VL-Q104G). Each of these humanized VH (or VL) variants was combined with the unmodified humanized VL (or VH) gene in the mammalian expression vector and using the cloning strategies detailed above (FIG. 22).

The resultant six expression vectors were individually transfected into HEK293 cells as described above and the antibodies produced by each transfectant were purified. Trop-2 antigen binding of these transiently expressed antibodies was analyzed by ELISA using a microtiter plate coated with 100 µl of 0.1 µg/ml rhTrop-2, i.e. in the conditions that had been used before to discriminate the humanized antibodies on the basis of their affinity for the target antigen. Among the four Hu2EF VH variants, only VH-R38K partially improved Trop-2 binding. The Hu2EF VH that carries the R38K mutation was named Hu2EF-VH7 (SEQ ID NO:25-26; FIG. 7 e FIG. 23). As to the humanized VL gene, both VL-M4L and VL-Q104G slightly improved Trop-2 binding. These two mutations were combined in Hu2EF VL1 to generate Hu2EF VL2 (SEQ ID NO: 29-30; FIG. 9 e FIG. 25).

Thus the new vector pHu2EF-7 (FIG. 22) was constructed that carries the Hu2EF VH7 (SEQ ID NO: 67; FIG. 33) and VL2 (SEQ ID NO: 68; FIG. 34) genes. In addition, the gpt gene in pHu2EF-7 was replaced by the gene encoding a puromycin N-acetyltransferase for resistance to puromycin in mammalian cells for generation of pHu2EF-7-puro. The pHu2EF-7 vector was transfected into HEK293 cells using Lipofectamine 2000 as described above, for transient expression of humanized 2EF IgG1/κ antibody carrying the Hu2EF VH7 and VL2 regions (Hu2EF-7). As a control, pCh2EF was also transiently transfected into HEK293 cells. Ch2EF and Hu2EF-7 antibodies in culture supernatants were tested for antigen binding by ELISA using a microtiter plate coated with 100 µl of 0.1 µg/ml of rhTrop2. Ch2EF and Hu2EF-7 showed vey similar binding to Trop-2 (FIG. 35), suggesting that Hu2EF-7 retains the antigen-binding affinity of the mouse 2EF antibody.

9. Expression and Purification of Hu2EF-7

For further analysis of Hu2EF-7, stable transfectants of a Chinese hamster ovary cell line CHO-K1 (ATCC, Manassas, Va.) were generated using pHu2EF-7-puro. CHO-K1 cells were grown in SFM4CHO media (HyClone) at 37° C. in a 7.5% CO2 incubator. Stable transfection into CHO-K1 was carried out by electroporation. Before transfection, pHu2EF-7-puro was linearized using FspI. Approximately $2.5 \times 10^6$ cells were transfected with 20 µg of linearized plasmid, suspended in SFM4CHO media, and plated into several 96-well plates after appropriate dilutions of cells, with the aim to isolate single clones that could produce the Hu2EF-7 antibody with high efficiency. After 48 hr, 10 µg/ml of puromycin was added for isolation of stable transfectants.

Approximately ten days after the initiation of selection, culture supernatants of transfectants were assayed for antibody production. Expression of Hu2EF-7 was measured by sandwich ELISA as described above. In this way a CHO-K1 transfectant was isolated that could produce high levels of Hu2EF-7 (CHO-K1-Hu2EF-7 2A2.2). This clone was expanded in SFM4CHO until the cell viability became less than 50%. Hu2EF-7 was then purified from culture supernatants using a protein A column as described above. In these conditions the yield of Hu2EF-7 from 500 ml of CHO-K1-Hu2EF-7 2A2.2 supernatant was 12.3 mg.

Stable transfectants of a rat myeloma cell line YB2/0 (ATCC, Manassas, Va.) producing Hu2EF-7 were also generated using pHu2EF-7. Electroporation of pHu2EF-7 into YB2/0 cells and selection of cells in mycophenolic acid media were carried out as described in Section 5. A YB2/0 stable transfectant producing a high level of Hu2EF-7 (YB2/0-Hu2EF-7 2D3) was expanded in Hybridoma-SFM containing 2% FBS in a roller bottle, fed with the feed media, and further cultured as described in Section 5. Hu2EF-7 was purified by protein A column chromatography. The yield was 4.0 mg from 500 ml culture supernatant.

Purified Hu2EF-7 antibody was characterized by SDS-PAGE according to standard procedures. Analysis under reducing conditions indicated that each of these antibodies is comprised of a heavy chain with a molecular weight of about 50 kDa and a light chain with a molecular weight of about 25 kDa (FIG. 36).

Authenticity of heavy and light chains produced in CHO-K1-Hu2EF-7 2A2.2 and YB2/0-Hu2EF-7 2D3 cells was confirmed by cDNA sequencing as described in Section 5. The resulting cDNA sequence of the coding regions for each of the Hu2EF-7 heavy and light chains matched perfectly with the corresponding sequence in pHu2EF-7 (FIG. 15 and FIG. 16).

10. Characterization of Hu2EF-7 for Binding to Trop-2

Binding to Trop-2 of the Hu2EF-7 antibody was characterized by flow cytometry. In a first experiment about $3 \times 10^5$ human colon cancer Colo205 cells were incubated with 0.3 µg/ml of Alexa-488-labelled murine 2EF (2EF-488), either alone or in combination with excess amount of an unlabelled competitor antibody, as described in Section 7 (FIG. 31).

In a second experiment approximately $5 \times 10^5$ Colo205 cells were incubated with 3 µg/ml of FITC-labeled mouse 2EF either alone or combined with various concentrations of unlabelled Hu2EF-7 competitor antibodies (produced in two different hosts), starting from 40 µg/mlm with serial 3-fold dilutions in 200 µl SM buffer for 30 min at 4° C. Cells were then processed as described in Section 7 and analyzed by flow citometry. Mean fluorescence values for each concentration of conpetitor antibody are shown in FIG. 37. From the data in FIG. 31 e FIG. 37 it can be seen that the humanized Hu2EF-7 antibody binds Trop-2 in a similar manner to the murine 2EF antibody, thus indicating that the humanization process has virtually retain the affinity and specificity for Trop-2 binding of the murine 2EF antibody. The two cell lines transfected with pHu2EF-7-puro and pHu2EF-7 for antibody production gave similar results.

The specificity of Trop-2 recognition was confirmed with a stringent analysis by flow cytometry, using as a target human colon cancer metastatic KM12SM tcellsransfected with Trop-2 or with the empty vector as a negative control, and stained with Hu2EF-7 plus a goat anti-human antiserum conjugated to Alexa 488 (FIG. 38A). Cells expressing Trop-2 are stained by the antibody, while identical cells without Trop-2 do not give fluorescent signal. Also, as expected from the humanization process, the Hu2EF-7 antibody is not recognized by anti-mouse antisera (FIG. 38B, left).

Thus this inventive approach succeeded in producing a humanized Hu2EF antibody that is able to bind with high affinity specific regions of the Trop-2 antigen, for use in diagnostics and therapy, alone or in combination with another humanized antibody that specifically recognises different regions of the target molecule, such as the 2G10-derived antibody for which we describe below the humanization process.

11. Construction of Chimeric 2G10 IgG1/κ Antibody

Mouse 2G10 hybridoma cells (PD 08020, AID-ICLC Genoa) were grown in RPMI-1640 medium containing 20% fetal bovine serum at 37° C. in a 7.5% $CO_2$ incubator. cDNAs for the VH and VL of the antibody produced by the 2G10 hybridoma were synthesized from total RNA extracted using TRIzol reagent as described in Section 1 using the following primers:

```
forward primers for 2G10 VH:
Universal Primer A Mix and Nested Universal Primer
A provided in the SMARTer RACE cDNA Amplification
Kit;
reverse primers for 2G10 VH:
MCG2A:
                                       (SEQ ID NO: 69)
5'-GCCAGTGGATAGACCGATGG-3';

forward primers for 2G10 VL:
Universal Primer A Mix provided in the SMARTer
RACE cDNA Amplification Kit;
2G10-L5:
                                       (SEQ ID NO: 70)
5'-ACCAGCACTGATATTGATG-3';

reverse primers for 2G10 VL:
JNT319:
                                       (SEQ ID NO: 55)
5'-CTCCCTCTAACACTCATTCCTGTTGAAGC-3';

2G10-L3:
                                       (SEQ ID NO: 71)
CGTGTACGGCAAGTTATCAC.
```

The amplified VH e VL were sequenced as described in Section 1.

A gene encoding 2G10 VH was generated as an exon including a splice donor signal (SEQ ID NO: 72; FIG. 39) by PCR, using the 2G10 VH cDNA as a template and the following primers:

```
forward:
                                       (SEQ ID NO: 73)
5'-GCAACTAGTACCACCATGGAATGGAACTGGGTC-3'
(SpeI site is underlined);

reverse:
                                       (SEQ ID NO: 74)
5'-GGGAAGCTTGAGAGGCCATTCTTACCTGAGGAGACGGTGACTGAGG
T-3' (HindIII site is underlined).
```

Likewise, a gene encoding 2G10 VL was generated as an exon including a splice donor signal (SEQ ID NO: 75; FIG. 40) by PCR, using 2G10 VL cDNA as a template and the following primers:

```
forward:
                                       (SEQ ID NO: 76)
5'-GCTGCTAGCACCACCATGTTCTCACTAGCTCTTCTCC-3'
(NheI site is underlined);

reverse:
                                       (SEQ ID NO: 77)
5'-CGAGAATTCTTTGGATTCTACTTACGTTTGATTTCCAGCTTGG
TC-3' (EcoRI site is underlined).
```

The splice donor signals of the 2G10 VH and VL exons were derived from the mouse germline JH4 and Jκ1 sequences, respectively. PCR-amplified fragments were gel-purified and cloned into the pCR4Blunt-TOPO vector for sequence confirmation. The correct fragments were digested with SpeI and HindIII (for VH) or NheI and EcoRI (for VL), gel-purified, and cloned into a mammalian expression vector carrying human G1 and κ constant regions for production of chimeric 2G10 IgG1/κ antibody (Ch2G10). The schematic structure of the resulting expression vector, pCh2G10, is shown in FIG. 22.

12. General Scheme of 2G10 Antibody Humanization

Designing of humanized 2G10 VH and VL amino acid sequences was carried out as follows. First, a three-dimensional molecular model of the mouse 2G10 variable regions was constructed using specifically developed approaches. Next, the framework amino acid residues important for the formation of the CDR structure were identified using the molecular model. In parallel, human VH and VL amino acid sequences with high homology to 2G10 VH and VL, respectively, were selected. Lastly, CDR sequences together with framework amino acid residues important for maintaining the CDR structure were grafted from 2G10 VH and VL into the corresponding selected human framework sequences.

13. Design of Humanized 2G10 VH and VL Genes

Human VH sequences homologous to the 2G10 VH frameworks were searched for within the GenBank database, and the VH sequence encoded by the human cDNA with NCBI Accession number: X65888.1 was chosen as an acceptor for humanization (X65888.1-VH). The CDR sequences of 2G10 VH (SEQ ID NO: 7-9) were first transferred to the corresponding positions of X65888.1-VH. Next, at framework positions 27, 30, 37, 48, 49, 67, 68, 70 and 72 (numbering from the first aminoacid of the mature form), where the three-dimensional model of the 2G10 variable regions suggested significant contact with the CDRs, the human amino acid residues were substituted with the corresponding mouse residues. The resulting humanized amino acid sequence Hu2G10 VH1 (SEQ ID NO: 32), alongside with the 2G10 and X65888.1-VH sequences, is shown in FIG. 41.

While Lys at position 67 and Ala at position 68 in mouse 2G10 VH, both of which are located closely to the CDRs, were predicted to be important for the formation of the CDR structure, amino acid residues in the human acceptor X65888.1-VH are Arg at position 67 and Val at position 68 (FIG. 41), which are similar to the corresponding mouse residues for molecular property and structure. Therefore, in order to further reduce potential immunogenicity, a second humanized VH (Hu2G10 VH2) was designed (SEQ ID NO: 34; FIG. 41), in which the aminoacid residues of the human acceptor are maintained at position 67 and 68, i.e. Arg and Val, respectively.

Based on the GenBank homology search with the 2G10 VL framework sequences, the human Vκ region encoded by the cDNA with NCBI Accession number: AY043146.1 was chosen as an acceptor for humanization. CDR sequences of 2G10 VL were first transferred to the corresponding positions of AY043146.1 VL (SEQ ID NO: 10-12). Next, at positions 49 and 67, where the three-dimensional model of the 2G10 variable regions indicated significant contact with the CDRs, the human amino acid residues were substituted with the corresponding residues of the mouse 2G10 VL. The amino acid sequence of the resulting humanized Hu2G10 VL1(SEQ ID NO: 36), is shown in FIG. 42 alongside with 2G10 and AY043146.1 VL sequences.

Although Tyr at position 67 in mouse 2G10 VL was predicted to be important for the formation of the CDR structure, further analysis of the three-dimensional model of the 2G10 variable regions suggested a possibility that this Tyr at position 67 could be replaced with Ser, a residue located at the corresponding position in the human acceptor AY043146.1 VL, without affecting antigen binding. Therefore in order to further reduce potential immunogenicity, a second humanized VL (Hu2G10 VL2) (SEQ ID NO: 38; FIG. 42) was designed, derived from Hu2G10 VL1, in which the Ser at position 67 in the human acceptor sequence is maintained.

14. Construction of Humanized 2G10 VH and VL Genes

Genes encoding each of Hu2G10 VH1, VH2, VL1 and VL2 were designed as exons, each including a signal peptide, a splice donor signal, and appropriate restriction enzyme sites for subsequent cloning into a mammalian expression vector (FIG. 22).The signal peptide sequence and splice donor signal of each gene were derived from the corresponding mouse 2G10 VH or VL gene in pCh2G10 (SEQ ID 72; FIG. 39).

The Hu2G10 VH1, VH2, VL1 and VL2 genes (SEQ ID NO: 78-81; FIG. 43-46) were synthesized by GenScript. After digestion with SpeI and HindIII (for VH) or NheI and EcoRI (for VL), these genes were subcloned into corresponding sites in a mammalian expression vector for production of human IgG1/κ(FIG. 22). As a result, four expression vectors were constructed. The first expression vector, pHu2G10-1, expresses the humanized 2G10 IgG1/κ antibody containing VH1 and VL1 (Hu2G10-1).The second vector, pHu2G10-2, expresses humanized 2G10 antibody containing VH1 and VL2 (Hu2G10-2). The third vector, pHu2G10-3, expresses humanized 2G10 antibody containing Hu2G10 VH2 and VL1 (Hu2G10-3). The fourth vector, pHu2G10-4, expresses humanized 2G10 antibody containing Hu2G10 VH2 and VL2 (Hu2G10-4).

15. Transient Expression and Characterization of Chimeric and Humanized 2G10 IgG1/κ Antibodies The expression vectors pCh2G10, pHu2G10-1, pHu2G10-2, pHu2G10-3 and pHu2G10-4 were individually transfected into the human embryonic kidney cell line HEK293 using Lipofectamine 2000 reagent according to the manufacturer's protocol.

Expression levels of transiently expressed antibodies were measured by sandwich ELISA as described in Section 5. Trop-2 binding of purified antibodies was tested by ELISA as described.

Binding of Hu2G10-1 and Hu2G10-3 to Trop-2 was slightly weaker than that of Ch2G10, whereas the binding of Hu2G10-2 and Hu2G10-4 was substantially lower than that of Ch2G10, indicating the importance of the amino acid residue at position 67 in VL for the proper formation of the antigen binding site. It was therefore concluded that the design of humanized 2G10 VL and/or VH had to be improved.

16. Design of Additional Humanized 2G10 VL Genes

As already seen during 2EF humanization, in order to avoid a significant loss of affinity there was the need for further detailed analyses of the three-dimensional model of the 2G10 variable regions, taking into consideration amino-acid residues and structural determinants that had not been considered during the first round of humanization. These analyses suggested that amino acid residues at non-canonical positions 2, 22, 42, 64, 72 and 85 in 2G10 VL could influence the structure of the antigen binding site. At each of these positions in Hu2G10 VL1, the human amino acid residue was substituted by the corresponding mouse residue by site-directed mutagenesis. The resultant variant Hu2G10 VL1 genes carry one of the following amino acid substitutions: Ile to Thr at position 2 (I2T), Thr to Arg at position 22

(T22R), Lys to Glu at position 42 (K42E), Gly to Ser at position 64 (G64S), Thr to Val at position 72 (T72V) and Thr to Asp at position 85 (T85D). Each of these VL variants was introduced into pHu2G10-1 for expression with Hu2G10 VH1.

The resultant six expression vectors, together with pCh2G10 and pHu2G10-1, were transiently transfected into HEK293 cells as described above. Binding of transiently expressed antibodies to Trop-2 was analyzed by ELISA as described above. Among the six Hu2G10 VL1 variants, only I2T improved Trop-2 binding substantially. The Hu2G10 VL1-I2T variant, which was renamed Hu2G10 VL3 (SEQ ID NO: 40), was therefore chosen for further characterization. Alignment of amino acid sequences for Hu2G10 VL1, VL2 and VL3 is shown in FIG. 42.

The expression vector carrying the Hu2G10 VH1 and VL3 genes (SEQ ID NO: 82; FIG. 47), was designated pHu2G10-5, and the corresponding antibody was named Hu2G10-5. The Hu2G10 VL3 gene was also introduced into pHu2G10-3; this new vector, which expresses the Hu2G10 VH2 and VL3 genes, was named pHu2G10-6, and Hu2G10-6 the corresponding antibody.

17. Generation of NS0 Stable Transfectants Producing Ch2G10, Hu2G10-5 and Hu2G10-6

The expression vectors pCh2G10, pHu2G10-5 and pHu2G10-6 were stably transfected into mouse myeloma NS0 cells as described in Section 5. Approximately 10 days after the initiation of selection, culture supernatants of each transfectant were assayed for antibody production by sandwich ELISA as described.

The NS0-Ch2G10 1A6, NS0-Hu2G10-5 B8 and NS0-Hu2G10-6 C9 stable transfectants, producing high levels of the corresponding antibodies, were adapted to growth in serum-free medium using Hybridoma SFM (Life Technologies). In addition, another NS0 stable transfectant producing a high level of Hu2G10-5 (NS0-Hu2G10 C10) was adapted to Hybridoma SFM. Frozen cell stocks of these NS0 stable transfectants were made in BamBanker and stored in liquid nitrogen.

NS0-Hu2G10-5 B8 and NS0-Hu2G10-6 C9 were tested with the PCR Mycoplasma Detection Set (Takara Bio USA, Madison, Wis.) and found negative for the presence of mycoplasma.

18. Purification of Ch2G10, Hu2G10-5 and Hu2G10-6

The stable NS0 transfectants generated as described above were used for the production of the corresponding antibodies in serum-free medium, as described in section 6. Antibodies were purified from supernatants by affinity cromatography on Protein A as described. The yield was 3.4 mg for Ch2G10 (from 1,000 ml), 1.9 mg for Hu2G10-5 (from 500 ml) and 18.2 mg for Hu2G10-6 (from 500 ml).

Purified Ch2G10, Hu2G10-5 and Hu2G10-6 antibodies were characterized by SDS-PAGE according to standard procedures. Analysis under reducing conditions indicated that each of these antibodies is comprised of a heavy chain with a molecular weight of about 50 kDa and a light chain with a molecular weight of about 25 kDa (FIG. 48). The purity of each antibody was higher than 95% as estimated from SDS-PAGE.

19. Analysis of Heavy and Light Chain mRNA

The authenticity of heavy and light chains produced in NS0-Ch2G10 1A6, NS0-Hu2G10-5 B8 and NS0-Hu2G10-6 C9 cells was confirmed by cDNA sequencing as described in Section 5. The sequences thus obtained of the coding regions for each of Ch2G10, Hu2G10-5, Hu2G10-6 heavy and light chains matched perfectly the corresponding sequences in the pCh2G10(SEQ ID NO: 83-86; FIG. 49-50), pHu2G10-5 (SEQ ID NO: 45-48; FIG. 17-18) and pHu2G10-6 (SEQ ID NO: 47-50; FIG. 18-19) vectors.

20. Characterization of Hu2G10-5 and Hu2G10-6 for Binding to Trop-2

Binding of purified Hu2G10-5 and Hu2G10-6 antibodies to Trop-2 was compared to that of Ch2G10 by competitive ELISA as described in Section 7, using a mixture of mouse 2G10 antibody (0.25 µg/ml) and competitor Ch2G10 or Hu2G10-5 or Hu2G10-6 antibodies (starting from 20 µg/ml with serial 2-fold dilutions) in ELISA buffer, 100 µl/well in duplicate. After incubating overnight at 4° C. and washing with Wash Buffer, the ELISA plate was incubated with 100 µl/well of HRP-conjugated goat anti-mouse κ chain (SouthernBiotech), 1/2,000-diluted in ELISA buffer, for 60 min at room temperature, and washed with Wash Buffer. Color development and absorbance measurement were carried out as described above. The $IC_{50}$ value of each competitor antibody was calculated using GraphPad Prism (GraphPad Software, San Diego, Calif.). The data are presented in FIG. 51 and show that the Hu2G10-5 and Hu2G10-6 antibodies compete similarly to CH2G10 for binding to Trop-2.

The binding to Trop-2 of the purified Ch2G10, Hu2G10-5 and Hu2G10-6 antibodies was also characterized by flow cytometry using alive cells that express native surface Trop-2 (either ndogenous or transfected). Approximately $3 \times 10^5$ murine MTE 4-14 cells transfected with Trop-2, or human breast cancer MCF7 cells expressing Trop-2 were incubated with 0.3 µg of murine 2G10 antibody conjugated with Alexa 488, either alone or pre-mixed with increasing amounts of unlabeled competitor antibody as described. The cells were then washed and analyzed by flow cytometry as described. Staining profiles are shown in FIG. 52 and FIG. 53.

The results of these analyses demonstrate that the Ch2G10, Hu2G10-5 and Hu2G10-6 antibody binding to the Trop-2 antigen is similar to that of the 2G10 antibody. This indicates that the humanization process has largely retained the 'affinity and specificity for the' antigen of the murine 2G10 antibody. Moreover, as expected from the humanization process, the humanized antibodies are not recognized by anti-mouse antisera (FIG. 38B, right; similar results were obtained for Hu2G10-5).

Example 2

MAb Binding to Monkey Trop-2.
Materials and Methods
Cells

The monkey fibroblast COS-7 cells were grown in DMEM medium with 10% FBS and 1% P/S at 37° C. and 5% CO2. Transfection was performed with Lipofectamine 2000 (Invitrogen) according to the manufacturer's instructions. COS-7 stable transfectants were selected with 400 µg/ml G418 for 12 days.

Plasmids

Primate Trop-2 sequences were retrieved from Genbank (www.ncbi.nlm.nih.gov/genbank/). Protein sequence were aligned using the Clustal Omega multialignment programme (www.ebi.ac.uk/Tools/msa/clustalo/). ORFs for cynomolgus monkey (*Macacafascicularis*), baboon (*Papioanubis*) and marmoset (*Callithrix jacchus*) TROP2 were synthesised by GenScript and inserted into the pAEYFP mammalian expression vector between the HindIII and the KpnI sites. The pAEYFP vector (CMV promoter) was derived from pEYFP-N1 (Clontech) by removal of the EYFP coding sequence. All syntetic constructs were sequence-verified.

Flow Cytometry Immunofluorescence Analysis and Cell Sorting.

Cell analyses and sorts were performed as described (Alberti, Nutini et al. 1994), using the FACSCalibur or the FACSCanto II and the FACSAria III flow cytometers/cell sorters (BD Biosciences). To improve the detection of transfectants stained with Alexa-488 labelled MAbs, subtraction of cell autofluorescence and displacement of Alexa-488-stained cells in the red channel were performed as described (Alberti, Parks et al. 1987; Alberti, Bucci et al. 1991).

Antibodies

The humanized Hu2EF-7 and Hu2G10-5 MAbs and the goat AF650 anti-Trop-2 pAb (R&D Systems) were used for flow cytometry analyses. The T16 anti-Trop-2 MAb (Alberti and Herzenberg 1988; Alberti, Miotti et al. 1992) was used for flow cytometry sorting of Trop-2 expressing cells. Preliminary tests on transient transfectants showed comparable recognition of the monkey Trop-2 antigen by the T16 Mab and the AF650 pAb. Antibodies were either directly conjugated to Alexa Fluor 488 or revealed with secondary Alexa Fluor-488 donkey anti-goat (DAG) IgG (Invitrogen).

Results

Mammalian expression vectors for cynomolgus monkey (*Macacafascicularis*), baboon (*Papioanubis*) and marmoset (*Callithrix jacchus*) Trop-2 were transfected into the monkey fibroblast COS-7 cell line. Human Trop-2 was included as positive control. The empty vector was used as negative control. COS-7 stable transfectants were obtained and enriched for higher level of Trop-2 expression by flow citometry as described. Binding of the Hu2EF-7 and Hu2G10-5 MAbs to the monkey Trop-2 antigen was tested by flow cytometry using the COS-7 transfectants as target. Both Hu2EF-7 and Hu2G10 were able to bind the monkey Trop-2 antigen with high efficiency (FIG. 54,55). Control COS-7/empty vector showed no binding.

Example 3

In Vitro ADCC, with Human Cells as Effectors.

Materials and Methods

Cells

Engineered Jurkat cells (effector cells) were purchased as part of the ADCC Reporter Bioassay, Core Kit (Cat. No. G7010, Promega) and used according to the manufacturer's protocol.

The MCF7 breast cancer cell line (target cells) was growth in RPMI medium with 10% FBS and 1% P/S at 37° C. and 5% CO2

ADCC Assay

The assay was performed according to the manufacturer's protocol. Briefly, MCF7 target cells (12500 cells/well) were seeded in a white, flat-bottom 96-well assay plate (Cat. No. 655001, Corning) in 100 μl RPMI medium with 10% FBS and 1% P/S. The day after, 4 μg of purified Hu2EF-7 or 37.6 μg of purified Hu2G10-5 were diluted in 200 μl ADCC assay buffer (96% RPMI 1640 with L-glutamine, 4% low IgG FBS); from this starting concentration five-fold serial dilutions were prepared in ADCC assay buffer. These MAb concentrations were chosen in preliminary experiments as the ones able to give a full dose-response curve. The medium was removed from the assay plate and 25 μl of each MAbdiluition were added to different wells of the assay plate, with increasing serial diluitions arranged column-wise. Three non-clustered replica wells were arranged for each MAbdiluition. One series of wells received no MAb (negative control). Only the 60 inner wells were used to avoid edge effects. The Jurkat effector cells were then added to each well (75,000 cells/well in 25 μl of ADCC assay buffer; effector to target cell ratio E:T=6:1). After 17 hours at 37° C., 5% CO2, the plate was equilibrated at RT, 75 μl of Bio-Glo Luciferase Assay Reagent (Cat. No. G7941, Promega) were added to each well and after 5 min the plate was read in a Veritas microplate luminometer (Turner Biosystems), with 0.5 s integration time. Luminescence values were plotted against the Log10 [MAB concentration]. Data were fitted to a 4 parameter logistic (4PL) non linear regression model to obtain the dose-response curve and the EC50 was calculated with the GraphPad Prism software.

Results

ADCC of the humanized Hu2EF-7 and Hu2G10-5 MAbs were measured using Jurkat cells stably expressing the V158 (high affinity) FcγRIIIa receptor and a NFAT response element upstream of firefly luciferase as effector cells. ADCC causes NFAT pathway activation with expression of the luciferase reported gene; the luciferase activity is quantified by a luminescence assay. MCF7 breast cancer cells were used as target cells. MCF7 endogenously express Trop-2 at levels which correspond to the average observed in corresponding primary human cancers (FIG. 55, 57). Different amounts of purified MAb were added to monolayers of MCF7 target cells in white 96-well assay plates (three replicas for data point). Engineered Jurkat effector cells were then added, with a ratio of effector cell to target cell of 6 to 1. Luciferase expression was quantified after 17 hours. Luminescence value were plotted against MAb concentration and a full dose-response curve was obtained (FIG. 56, 58). The EC50 for the Hu2EF-MAb under these assay conditions was 52 ng/ml (40-68 ng/ml 95% confidence interval), thus comparable to widely used anticancer therapeutic MABs. As a comparison, representative EC50 reported for therapeutic MAbs under these same assay conditions are 10.0 ng/ml for trastuzumab/SK-BR-3 target cells, 15.6 ng/ml for cetuximab/A431 target cells. The EC50 for the Hu2G10-5 MAb under these assay conditions was 4.15 μg/ml (2.96-5.83 μg/ml 95% confidence interval), indicating that the two humanized anti-Trop-2 MABs differs greatly in their ability to elicit an ADCC response on target cells, Hu2EF-7 being much more effective than Hu2G10-5.

Example 4

In Vivo Antitumorefficacy of the Humanized Hu2G10-5 MAb

Efficacy in tumor growth inhibition of the Hu2G10-5 MAB was assayed on prostate cancer DU-145 cells (FIG. 60), as compared with that of the murine 2G10.

Tumor cell lines were injected subcutaneously in nude mice. Mice were treated i.p with 800 μg (total) of the indicated mAbs. once a week, starting on already growing (established) tumors. The arrow indicates the beginning of the treatment.

The humanized antibody retains full anti-tumor efficacy in vivo.

REFERENCES

Afif, W., E. V. Loftus, Jr., et al. (2010). "Clinical utility of measuring infliximab and human anti-chimeric antibody concentrations in patients with inflammatory bowel disease." *Am J Gastroenterol* 105(5): 1133-9.

Alberti, S., C. Bucci, et al. (1991). "Immunofluorescence analysis in flow cytometry: better selection of antibody-labeled cells after fluorescence overcompensation in the red channel." *J. Histochem. Cytochem.* 39(5): 701-6.

Alberti, S. and L. A. Herzenberg (1988). "DNA methylation prevents transfection of genes for specific surface antigens." *Proc. Natl. Acad. Sci. USA* 85: 8391-4.

Alberti, S., S. Miotti, et al. (1992). "Biochemical characterization of Trop-2, a cell surface molecule expressed by human carcinomas: formal proof that the monoclonal antibodies T16 and MOv-16 recognize Trop-2." *Hybridoma* 11: 539-5.

Alberti, S., M. Nutini, et al. (1994). "DNA methylation prevents the amplification of TROP1, a tumor associated cell surface antigen gene." Proc. Natl. Acad. Sci. USA 91: 5833-7.

Alberti, S., D. R. Parks, et al. (1987). "A single laser method for subtraction of cell autofluorescence in flow cytometry." *Cytometry* 8: 114-9.

Ali, Z., A. L. Aloisi, et al. (2013). "Trop-2 recruits ADAM10 to signaling platforms as an activatory switch for cancer growth." submitted.

Ambrogi, F., M. Fornili, et al. (2014). "Trop-2 is a determinant of breast cancer survival." *PLoS One* 9(5): e96993.

Basu, A., D. M. Goldenberg, et al. (1995). "The epithelial/ carcinoma antigen EGP-1, recognized by monoclonal antibody RS7-3G11, is phosphorylated on serine 303." *Int J Cancer* 62(4): 472-9.

Bignotti, E., P. Todeschini, et al. (2010). "Trop-2 overexpression as an independent marker for poor overall survival in ovarian carcinoma patients." *Eur J Cancer* 46(5): 944-53.

Bosco, J. L., S. Antonsen, et al. (2011). "Metformin and incident breast cancer among diabetic women: a population-based case-control study in Denmark." *Cancer Epidemiol Biomarkers Prev* 20(1): 101-11.

Calabrese, G., C. Crescenzi, et al. (2001). "Assignment of TACSTD1 (alias TROP1, M4S1) to human chromosome 2p21 and refinement of mapping of TACSTD2 (alias TROP2, M1S1) to human chromosome 1p32 by in situ hybridization." *Cytogenet. Cell Genet.* 92(1-2): 164-5.

Ciccarelli, F., A. Acciarito, et al. (2000). "Large and diverse numbers of human diseases with HIKE mutations." *Hum. Mol. Genet.* 9: 1001-7.

Fang, Y. J., Z. H. Lu, et al. (2009). "Elevated expressions of MMPI, TROP2, and survivin are associated with survival, disease recurrence, and liver metastasis of colon cancer." *Int J Colorectal Dis* 24(8): 875-84.

Fong, D., P. Moser, et al. (2008). "High expression of TROP2 correlates with poor prognosis in pancreatic cancer." *Br J Cancer* 99(8): 1290-5.

Fornaro, M., R. Dell'Arciprete, et al. (1995). "Cloning of the gene encoding TROP-2, a cell-surface glycoprotein expressed by human carcinomas." Int. J. Cancer 62: 610-8.

Fradet, Y., C. Cordon-Cardo, et al. (1984). "Cell-surface antigens of human bladder cancer defined by mouse monoclonal antibodies." *Proc. Natl. Acad. Sci. USA* 81: 224-228.

Guerra, E., M. Trerotola, et al. (2013). "The Trop-2 signalling network in cancer growth." *Oncogene* 32: 1594-1600.

Jiang, A., X. Gao, et al. (2013). "Expression and clinical significance of the Trop-2 gene in advanced non-small cell lung carcinoma." *Oncol Lett* 6(2): 375-380.

Kabat, E. A., T. T. Wu, et al. (1991). *Sequences of Proteins of Immunological Interests*, Diane Pub Co.

Khazaeli, M. B., R. M. Conry, et al. (1994). "Human immune response to monoclonal antibodies." *J Immunother Emphasis Tumor Immunol* 15(1): 42-52.

Linnenbach, A. J., B. A. Seng, et al. (1993). "Retroposition in a family of carcinoma-associated antigen genes." *Mol. Cell. Biol.* 13: 1507-1515.

Liu, A. Y., R. R. Robinson, et al. (1987). "Production of a mouse-human chimeric monoclonal antibody to CD20 with potent Fc-dependent biologic activity." *J Immunol* 139(10): 3521-6.

Morrison, S. L., M. J. Johnson, et al. (1984). "Chimeric human antibody molecules: mouse antigen-binding domains with human constant region domains." *Proc Natl Acad Sci USA* 81(21): 6851-5.

Muhlmann, G., G. Spizzo, et al. (2009). "TROP2 expression as prognostic marker for gastric carcinoma." *J Clin Pathol* 62(2): 152-8.

Naquet, P., H. Lepesant, et al. (1989). "Establishment and characterization of mouse thymic epithelial cell lines." *Thymus* 13(3-4): 217-26.

Ohmachi, T., F. Tanaka, et al. (2006). "Clinical significance of TROP2 expression in colorectal cancer." *Clin Cancer Res* 12(10): 3057-63.

Pauli, C., M. Munz, et al. (2003). "Tumor-specific glycosylation of the carcinoma-associated epithelial cell adhesion molecule EpCAM in head and neck carcinomas." *Cancer Lett* 193(1): 25-32.

The invention claimed is:

1. A humanized antibody, or fragments or conjugates thereof, which recognizes and binds the same epitope or epitopes as the antibody 2G10 produced by the hybridoma deposited in the Advanced Biotechnology Center (ABC) with the number PD 08020;
   (a) wherein the humanized antibody comprises (i) a variable domain framework region from a heavy chain of a human antibody or from a human consensus framework; and/or (ii) a variable domain framework region from a light chain of a human antibody or from a human consensus framework; and
   (b) wherein (i) at least one amino acid in the variable domain framework region from the heavy chain is substituted with a corresponding amino acid from a heavy chain of a mouse antibody or mouse consensus framework and/or (ii) at least one amino acid in the variable domain framework region from the light chain is substituted with a corresponding amino acid from a light chain of a mouse antibody or mouse consensus framework; and
   (c) wherein (i) the amino acid substitutions in the heavy chain are:
   F (murine) instead of Y (human) at position 27, and/or
   S (murine) instead of T (human) at position 30, and/or
   L (murine) instead of V (human) at position 37, and/or
   I (murine) instead of M (human) at position 48, and/or
   A (murine) instead of G (human) at position 49, and/or
   L (murine) instead of I (human) at position 70, and/or
   V (murine) instead of R (human) at position 72; and/or
   (ii) the amino acid substitution in the light chain is S (murine) instead of Y (human) at position 49; and
   (d) wherein the humanized antibody comprises (i) a heavy chain complementary determining region (CDRH3) amino acid sequence having the amino acid sequence of SEQ ID NO:9, and a heavy chain complementary determining region (CDRH2) amino acid sequence having the amino acid sequence of SEQ ID NO:8, and a heavy chain complementary determining region (CDRH1) amino acid sequence having the amino acid sequence of SEQ ID NO:7; and (ii) a light chain complementary determining region (CDRL3) amino acid sequence having the amino acid sequence of SEQ ID NO: 12, and a light chain complementary determining region (CDRL2) amino acid sequence having the amino acid sequence of SEQ ID NO: 11, and a light chain complementary determining region (CDRL1) amino acid sequence having the amino acid sequence of SEQ ID NO: 10.

2. A kit for diagnosing tumors and metastases comprising a humanized antibody or fragment or conjugate thereof according to claim 1 and means for detecting tumors and metastases.

3. The humanized antibody, or fragments or conjugates thereof according to claim 1 wherein the amino acid substitutions of the heavy chain of the human antibody further comprise at least one of:

K (murine) instead of R (human) at position 67, and/or
A (murine) instead of V (human) at position 68.

4. The humanized antibody, or fragments or conjugates thereof according to claim 1 wherein the amino acid substitutions of the heavy chain of the human antibody comprise:
F (murine) instead of Y (human) at position 27 and
S (murine) instead of T (human) at position 30 and
L (murine) instead of V (human) at position 37, and
I (murine) instead of M (human) at position 48, and
A (murine) instead of G (human) at position 49, and
L (murine) instead of I (human) at position 70, and
V (murine) instead of R (human) at position 72.

5. The humanized antibody, or fragments or conjugates thereof according to claim 1 wherein the heavy chain of the human antibody (claim 1(a)(i)) comprises the sequence of SEQ ID NO: 90.

6. The humanized antibody, or fragments or conjugates thereof according to claim 1 wherein the amino acid substitutions in the light chain further comprise at least one of:
(i) Y (murine) instead of S (human) at position 67; or
(ii) T (murine) instead of I (human) at position 2 and Y (murine) instead of S (human) at position 67; or
(iii) R (murine) instead of T (human) at position 22 and Y (murine) instead of S (human) at position 67; or
(iv) E (murine) instead of K (human) at position 42 and Y (murine) instead of S (human) at position 67; or
(v) S (murine) instead of G (human) at position 64 and Y (murine) instead of S (human) at position 67; or
(vi) Y (murine) instead of S (human) at position 67 and V (murine) instead of T (human) at position 72; or
(vii) Y (murine) instead of S (human) at position 67, and D (murine) instead of T (human) at position 85.

7. The humanized antibody, or fragments or conjugates thereof according to claim 1 wherein the light chain of the human antibody (claim 1(a)(ii)) has the sequence of SEQ ID NO:92.

8. The humanized antibody, or fragments or conjugates thereof, according to claim 1, comprising a heavy chain variable region amino acid sequence having at least 80% identity to the amino acid sequence selected from the group consisting of amino acid residues 20-138 of SEQ ID NOs: 18, 32, or 34 or fragments thereof and/or a light chain variable region amino acid sequence having at least 80% identity to the amino acid sequence selected from the group consisting of amino add residues 21-127 of SEQ ID NOs: 20, 36, 38 or 40 or fragments thereof, or fragments or conjugates thereof.

9. The humanized antibody, or fragments or conjugates thereof according to claim 8, comprising a heavy chain variable region amino acid sequence comprising amino acid residues 20-138 of SEQ ID NO:32 or SEQ ID NO:34 and a light chain variable region amino acid sequence comprising amino acid residues 21-127 of SEQ ID NO:40.

10. The humanized antibody, or fragments or conjugates thereof, according to claim 8, comprising a heavy chain variable region amino acid sequence having at least 80% identity to the amino acid sequence selected from the group consisting of SEQ ID NOs: 18, 32, or 34 or fragments thereof and/or a light chain variable region amino acid sequence having at least 80% identity to the amino acid sequence selected from the group consisting of SEQ ID NOs: 20, 36, 38 or 40 or fragments thereof, or fragments or conjugates thereof.

11. The humanized antibody, or fragments or conjugates thereof according to claim 10, comprising a heavy chain variable region amino acid sequence comprising SEQ ID NO:32 or SEQ ID NO:34 and a light chain variable region amino acid sequence comprising SEQ ID NO:40.

12. The humanized antibody, or fragments or conjugates thereof according to claim 1 wherein the humanized antibody comprises (i) a variable domain framework region from a heavy chain of a human antibody or from a human consensus framework; and (ii) a variable domain framework region from a light chain of a human antibody or from a human consensus framework.

13. The humanized antibody, or fragments or conjugates thereof according to claim 1 wherein (i) an amino acid in the variable domain framework region from the heavy chain of a human antibody is substituted with the corresponding amino acid from a heavy chain of a mouse antibody or mouse consensus framework and (ii) an amino acid in the variable domain framework region from the light chain of a human antibody is substituted with the corresponding amino acid from a light chain of a mouse antibody or mouse consensus framework.

14. A nucleic acid molecule encoding a humanized antibody or fragments or conjugates thereof according to claim 1, or hybridizing with the nucleic acid, or a degenerate sequence thereof.

15. The nucleic acid molecule according to claim 14 comprising a nucleic acid sequence selected from the group consisting of SEQ ID NO: 17, 19, 31, 33, 35, 37, 39, 45, 47 and 49.

16. An expression vector comprising a nucleic acid encoding the humanized antibody or fragments or conjugates of claim 1.

17. A host cell that produces a humanized antibody or fragments or conjugates thereof according to claim 1.

18. A pharmaceutical composition that comprises a humanized antibody or fragment or conjugate thereof according to claim 1 and an excipient and/or adjuvant and/or carrier and/or diluent that is pharmaceutically acceptable.

* * * * *

SEQUENCE LISTING

```
<160> NUMBER OF SEQ ID NOS: 97

<210> SEQ ID NO 1
<211> LENGTH: 5
<212> TYPE: PRT
<213> ORGANISM: Mus musculus
<220> FEATURE:
<223> OTHER INFORMATION: CDR

<400> SEQUENCE: 1

Asn Tyr Trp Ile Gly
1               5

<210> SEQ ID NO 2
<211> LENGTH: 17
<212> TYPE: PRT
```

```
<213> ORGANISM: Mus musculus
<220> FEATURE:
<223> OTHER INFORMATION: CDR

<400> SEQUENCE: 2

Asp Ile Tyr Pro Gly Gly Gly Tyr Thr Asn Tyr Asn Glu Lys Phe Lys
1               5                   10                  15

Gly

<210> SEQ ID NO 3
<211> LENGTH: 7
<212> TYPE: PRT
<213> ORGANISM: Mus musculus

<400> SEQUENCE: 3

Gly Thr Gly Gly Gly Asp Tyr
1               5

<210> SEQ ID NO 4
<211> LENGTH: 15
<212> TYPE: PRT
<213> ORGANISM: Mus musculus

<400> SEQUENCE: 4

Arg Ala Ser Gln Ser Val Ser Thr Ser Ser Tyr Ser Tyr Met His
1               5                   10                  15

<210> SEQ ID NO 5
<211> LENGTH: 7
<212> TYPE: PRT
<213> ORGANISM: Mus musculus

<400> SEQUENCE: 5

Tyr Ala Ser Asn Leu Glu Ser
1               5

<210> SEQ ID NO 6
<211> LENGTH: 9
<212> TYPE: PRT
<213> ORGANISM: Mus musculus

<400> SEQUENCE: 6

Gln His Ser Trp Glu Ile Pro Tyr Thr
1               5

<210> SEQ ID NO 7
<211> LENGTH: 5
<212> TYPE: PRT
<213> ORGANISM: Mus musculus

<400> SEQUENCE: 7

Ser Ser Tyr Ile Ser
1               5

<210> SEQ ID NO 8
<211> LENGTH: 17
<212> TYPE: PRT
<213> ORGANISM: Mus musculus

<400> SEQUENCE: 8

Trp Ile Tyr Ala Gly Thr Gly Gly Thr Ser Tyr Asn Gln Lys Phe Thr
1               5                   10                  15

Gly
```

<210> SEQ ID NO 9
<211> LENGTH: 10
<212> TYPE: PRT
<213> ORGANISM: Mus musculus

<400> SEQUENCE: 9

His Asn Pro Arg Tyr Tyr Ala Met Asp Tyr
1               5                   10

<210> SEQ ID NO 10
<211> LENGTH: 11
<212> TYPE: PRT
<213> ORGANISM: Mus musculus

<400> SEQUENCE: 10

Ile Thr Ser Thr Asp Ile Asp Asp Met Asn
1               5                   10

<210> SEQ ID NO 11
<211> LENGTH: 7
<212> TYPE: PRT
<213> ORGANISM: Mus musculus

<400> SEQUENCE: 11

Glu Gly Asn Thr Leu Arg Pro
1               5

<210> SEQ ID NO 12
<211> LENGTH: 9
<212> TYPE: PRT
<213> ORGANISM: Mus musculus

<400> SEQUENCE: 12

Leu Gln Ser Asp Asn Leu Pro Tyr Thr
1               5

<210> SEQ ID NO 13
<211> LENGTH: 405
<212> TYPE: DNA
<213> ORGANISM: Mus musculus

<400> SEQUENCE: 13
atggaatgga gcggggtctt tatctttctc ctgtcagtga ctgcaggcgt ccactcccaa    60
gtccagctcc agcagtctgg agctgagctc gtgaggcctg ggacttcagt gaagatgtcc   120
tgcaaggctg ctggatacac cttcactaac tactggatcg gatgggtgaa gcagaggcct   180
ggacatggcc tcgagtggat tggagatatt taccctggag gaggctatac taactacaat   240
gagaagttca gggcaaggc cacactgact gcagacacat cctccagcac agcctacatg   300
cagctcagca gcctgacatc tgaggactct gccatctatt actgtgcaag gaactgga   360 ggcggagact actggggcca agggactctg gtcactgtct ctgca                  405

<210> SEQ ID NO 14
<211> LENGTH: 135
<212> TYPE: PRT
<213> ORGANISM: Mus musculus

<400> SEQUENCE: 14

Met Glu Trp Ser Gly Val Phe Ile Phe Leu Leu Ser Val Thr Ala Gly
1               5                   10                  15

Val His Ser Gln Val Gln Leu Gln Gln Ser Gly Ala Glu Leu Val Arg
            20                  25                  30

Pro Gly Thr Ser Val Lys Met Ser Cys Lys Ala Ala Gly Tyr Thr Phe
         35                  40                  45

Thr Asn Tyr Trp Ile Gly Trp Val Lys Gln Arg Pro Gly His Gly Leu
     50                  55                  60

Glu Trp Ile Gly Asp Ile Tyr Pro Gly Gly Gly Tyr Thr Asn Tyr Asn
 65                  70                  75                  80

Glu Lys Phe Lys Gly Lys Ala Thr Leu Thr Ala Asp Thr Ser Ser Ser
                 85                  90                  95

Thr Ala Tyr Met Gln Leu Ser Ser Leu Thr Ser Glu Asp Ser Ala Ile
             100                 105                 110

Tyr Tyr Cys Ala Arg Gly Thr Gly Gly Gly Asp Tyr Trp Gly Gln Gly
         115                 120                 125

Thr Leu Val Thr Val Ser Ala
     130                 135

<210> SEQ ID NO 15
<211> LENGTH: 393
<212> TYPE: DNA
<213> ORGANISM: Mus musculus

<400> SEQUENCE: 15
atggagacag acacactcct gctatgggtg ctgctgctct gggttccagg ttccactggt    60
gacattgtgc tgacacagtc tcctgcttcc ttagctgtat ctctgggca gagggccacc   120 atctcatgca gggccagcca aagtgtcagt acatctagct atagttatat gcactggtac   180
caacagaaac caggacagcc acccaaactc ctcatcaagt atgcatccaa cctagaatct   240
ggggtccctg ccaggttcag tggcagtggg tctgggacag acttcaccct caacatccat   300
cctgtggagg aggaggatac tgcaacatat tactgtcagc acagttggga gattccgtac   360
acgttcggag gggggaccaa gctggaaata aaa                                393

<210> SEQ ID NO 16
<211> LENGTH: 131
<212> TYPE: PRT
<213> ORGANISM: Mus musculus

<400> SEQUENCE: 16

Met Glu Thr Asp Thr Leu Leu Leu Trp Val Leu Leu Leu Trp Val Pro
 1               5                  10                  15

Gly Ser Thr Gly Asp Ile Val Leu Thr Gln Ser Pro Ala Ser Leu Ala
             20                  25                  30

Val Ser Leu Gly Gln Arg Ala Thr Ile Ser Cys Arg Ala Ser Gln Ser
         35                  40                  45

Val Ser Thr Ser Ser Tyr Ser Tyr Met His Trp Tyr Gln Gln Lys Pro
     50                  55                  60

Gly Gln Pro Pro Lys Leu Leu Ile Lys Tyr Ala Ser Asn Leu Glu Ser
 65                  70                  75                  80

Gly Val Pro Ala Arg Phe Ser Gly Ser Gly Ser Gly Thr Asp Phe Thr
                 85                  90                  95

Leu Asn Ile His Pro Val Glu Glu Glu Asp Thr Ala Thr Tyr Tyr Cys
             100                 105                 110

Gln His Ser Trp Glu Ile Pro Tyr Thr Phe Gly Gly Gly Thr Lys Leu
         115                 120                 125

Glu Ile Lys
     130

<210> SEQ ID NO 17
<211> LENGTH: 414
<212> TYPE: DNA
<213> ORGANISM: Mus musculus

<400> SEQUENCE: 17

```
atggaatgga actgggtcgt tctcttcctc ctgtcattaa ctgcaggtgt ctattcccag      60
ggtcagatgc agcagtctgg agctgagctg gtgaagcctg gggcttcagt gaagctgtcc    120
tgcaagactt ctggcttcac cttcagcagt agctatataa gttggttgaa gcagaagcct    180
cgacagagtc ttgagtggat tgcatggatt tatgctggaa ctggtggtac tagctataat    240
cagaagttca caggcaaggc ccaactgact gtagacacat cctccagcac agcctacatg    300
caactcagca gcctgacatc tgaggactct gccatctatt actgtgcaag acataaccct    360
cgttactatg ctatggacta ctggggtcaa ggaacctcag tcaccgtctc ctca          414
```

<210> SEQ ID NO 18
<211> LENGTH: 138
<212> TYPE: PRT
<213> ORGANISM: Mus musculus

<400> SEQUENCE: 18

```
Met Glu Trp Asn Trp Val Val Leu Phe Leu Leu Ser Leu Thr Ala Gly
1               5                  10                  15

Val Tyr Ser Gln Gly Gln Met Gln Gln Ser Gly Ala Glu Leu Val Lys
            20                  25                  30

Pro Gly Ala Ser Val Lys Leu Ser Cys Lys Thr Ser Gly Phe Thr Phe
        35                  40                  45

Ser Ser Ser Tyr Ile Ser Trp Leu Lys Gln Lys Pro Arg Gln Ser Leu
    50                  55                  60

Glu Trp Ile Ala Trp Ile Tyr Ala Gly Thr Gly Gly Thr Ser Tyr Asn
65                  70                  75                  80

Gln Lys Phe Thr Gly Lys Ala Gln Leu Thr Val Asp Thr Ser Ser Ser
                85                  90                  95

Thr Ala Tyr Met Gln Leu Ser Ser Leu Thr Ser Glu Asp Ser Ala Ile
            100                 105                 110

Tyr Tyr Cys Ala Arg His Asn Pro Arg Tyr Tyr Ala Met Asp Tyr Trp
        115                 120                 125

Gly Gln Gly Thr Ser Val Thr Val Ser Ser
    130                 135
```

<210> SEQ ID NO 19
<211> LENGTH: 381
<212> TYPE: DNA
<213> ORGANISM: Mus musculus

<400> SEQUENCE: 19

```
atgttctcac tagctcttct cctcagtctt cttctcctct gtgtctctga ttctagggca      60
gaaacaactg tgacccagtc tccagcatcc ctgtccatgg ctataggaga aaaagtcacc    120
atcagatgca taaccagcac tgatattgat gatgatatga actggtacca gcagaagcca    180
ggggaacctc ctaagctcct tatttcagaa ggcaatactc ttcgtcctgg agtcccatcc    240
cgattctcca gcagtggcta tggtacagat tttgttttta caattgaaaa catgctctca    300
gaagatgttg cagattacta ctgtttgcaa agtgataact gccgtacac gttcggaggg    360
gggaccaagc tggaaataaa a                                                381
```

<210> SEQ ID NO 20
<211> LENGTH: 127
<212> TYPE: PRT
<213> ORGANISM: Mus musculus

<400> SEQUENCE: 20

Met Phe Ser Leu Ala Leu Leu Ser Leu Leu Leu Leu Cys Val Ser
1               5                   10                  15

Asp Ser Arg Ala Glu Thr Thr Val Thr Gln Ser Pro Ala Ser Leu Ser
            20                  25                  30

Met Ala Ile Gly Glu Lys Val Thr Ile Arg Cys Ile Thr Ser Thr Asp
        35                  40                  45

Ile Asp Asp Asp Met Asn Trp Tyr Gln Gln Lys Pro Gly Glu Pro Pro
50                  55                  60

Lys Leu Leu Ile Ser Glu Gly Asn Thr Leu Arg Pro Gly Val Pro Ser
65                  70                  75                  80

Arg Phe Ser Ser Ser Gly Tyr Gly Thr Asp Phe Val Phe Thr Ile Glu
                85                  90                  95

Asn Met Leu Ser Glu Asp Val Ala Asp Tyr Tyr Cys Leu Gln Ser Asp
            100                 105                 110

Asn Leu Pro Tyr Thr Phe Gly Gly Gly Thr Lys Leu Glu Ile Lys
        115                 120                 125

<210> SEQ ID NO 21
<211> LENGTH: 405
<212> TYPE: DNA
<213> ORGANISM: Artificial sequence
<220> FEATURE:
<223> OTHER INFORMATION: Humanized VH

<400> SEQUENCE: 21
atggaatgga gcggggtctt tatctttctc ctgtcagtga ctgcaggcgt ccactcccaa      60
gtccagctcg tgcagtctgg agctgaagtg aagaaacctg ggcttcagt gaaggtgtcc      120 tgcaaggctt ctggatacac cttcactaac tactggatcg gatgggtcag acaggcccct    180
ggacagggcc tcgagtggat tggagatatt taccctggag gaggctatac taactacaat    240
gagaagttca agggcagagc cacactgact gcagacacat ccgccagcac agcctacatg    300
gagctcagca gcctgagatc tgaggacact gccgtgtatt actgtgcaag aggaactgga    360
ggcggagact actggggcca aggactctg gtcactgtct cttca                     405

<210> SEQ ID NO 22
<211> LENGTH: 135
<212> TYPE: PRT
<213> ORGANISM: Artificial sequence
<220> FEATURE:
<223> OTHER INFORMATION: Humanized VH

<400> SEQUENCE: 22

Met Glu Trp Ser Gly Val Phe Ile Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Trp Ile Gly Trp Val Arg Gln Ala Pro Gly Gln Gly Leu
    50                  55                  60

Glu Trp Ile Gly Asp Ile Tyr Pro Gly Gly Gly Tyr Thr Asn Tyr Asn

```
                  65                  70                  75                  80
Glu Lys Phe Lys Gly Arg Ala Thr Leu Thr Ala Asp Thr Ser Ala Ser
                            85                  90                  95

Thr Ala Tyr Met Glu Leu Ser Ser Leu Arg Ser Glu Asp Thr Ala Val
                100                 105                 110

Tyr Tyr Cys Ala Arg Gly Thr Gly Gly Asp Tyr Trp Gly Gln Gly
            115                 120                 125

Thr Leu Val Thr Val Ser Ser
        130                 135

<210> SEQ ID NO 23
<211> LENGTH: 405
<212> TYPE: DNA
<213> ORGANISM: Artificial sequence
<220> FEATURE:
<223> OTHER INFORMATION: Humanized VH

<400> SEQUENCE: 23
atggaatgga gcggggtctt tatctttctc ctgtcagtga ctgcaggcgt ccactcccaa      60
gtccagctcg tgcagtctgg agctgaagtg aagaaacctg gggcttcagt gaaggtgtcc     120
tgcaaggctt ctggatacac cttcactaac tactggatcg gatgggtcag acaggcccct    180
ggacagggcc tcgagtggat tggagatatt taccctggag gaggctatac taactacaat    240
gagaagttca aggcagagc cacactgact gcagacacat ccaccagcac agcctacatg     300
gagctcagca gcctgagatc tgaggacact gccgtgtatt actgtgcaag aggaactgga   360
ggcggagact actggggcca agggactctg gtcactgtct cttca                    405

<210> SEQ ID NO 24
<211> LENGTH: 135
<212> TYPE: PRT
<213> ORGANISM: Artificial sequence
<220> FEATURE:
<223> OTHER INFORMATION: Humanized VH

<400> SEQUENCE: 24

Met Glu Trp Ser Gly Val Phe Ile Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Trp Ile Gly Trp Val Arg Gln Ala Pro Gly Gln Gly Leu
    50                  55                  60

Glu Trp Ile Gly Asp Ile Tyr Pro Gly Gly Gly Tyr Thr Asn Tyr Asn
65                  70                  75                  80

Glu Lys Phe Lys Gly Arg Ala Thr Leu Thr Ala Asp Thr Ser Thr Ser
                85                  90                  95

Thr Ala Tyr Met Glu Leu Ser Ser Leu Arg Ser Glu Asp Thr Ala Val
                100                 105                 110

Tyr Tyr Cys Ala Arg Gly Thr Gly Gly Asp Tyr Trp Gly Gln Gly
            115                 120                 125

Thr Leu Val Thr Val Ser Ser
        130                 135

<210> SEQ ID NO 25
<211> LENGTH: 405
<212> TYPE: DNA
```

<213> ORGANISM: Artificial sequence
<220> FEATURE:
<223> OTHER INFORMATION: Humanized VH

<400> SEQUENCE: 25

| | |
|---|---:|
| atggaatgga gcggggtctt tatctttctc ctgtcagtga ctgcaggcgt ccactcccaa | 60 |
| gtccagctcg tgcagtctgg agctgaagtg aagaaacctg ggcttcagt gaaggtgtcc | 120 |
| tgcaaggctt ctggatacac cttcactaac tactggatcg gatgggtcag acaggcccct | 180 |
| ggacagggcc tcgagtggat tggagatatt taccctggag gaggctatac taactacaat | 240 |
| gagaagttca aggcagagc cacactgact gcagacacat ccaccagcac agcctacatg | 300 |
| gagctcagca gcctgagatc tgaggacact gccgtgtatt actgtgcaag aggaactgga | 360 |
| ggcggagact actggggcca aggactctg gtcactgtct cttca | 405 |

<210> SEQ ID NO 26
<211> LENGTH: 135
<212> TYPE: PRT
<213> ORGANISM: Artificial sequence
<220> FEATURE:
<223> OTHER INFORMATION: Humanized VH

<400> SEQUENCE: 26

Met Glu Trp Ser Gly Val Phe Ile Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Trp Ile Gly Trp Val Lys Gln Ala Pro Gly Gln Gly Leu
    50                  55                  60

Glu Trp Ile Gly Asp Ile Tyr Pro Gly Gly Gly Tyr Thr Asn Tyr Asn
65                  70                  75                  80

Glu Lys Phe Lys Gly Arg Ala Thr Leu Thr Ala Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Thr Gly Gly Gly Asp Tyr Trp Gly Gln Gly
        115                 120                 125

Thr Leu Val Thr Val Ser Ser
    130                 135

<210> SEQ ID NO 27
<211> LENGTH: 394
<212> TYPE: DNA
<213> ORGANISM: Artificial sequence
<220> FEATURE:
<223> OTHER INFORMATION: Humanized VL

<400> SEQUENCE: 27

| | |
|---|---:|
| atggagacag acacactcct gctgtgggtg ctgctgctct gggttccagg ctccactggc | 60 |
| gacattgtga tgacacagtc tcctgactcc ctggctgtgt ctctggggga gagggccacc | 120 |
| atcaactgca gggccagcca aagtgtcagt acatctagct atagttatat gcactggtac | 180 |
| caacagaaac caggacagcc acccaaactc ctcatcaagt atgcatccaa cctggaatct | 240 |
| ggggtccctg acagattcag tggcagtggg tctgggacag acttcaccct caccatcagc | 300 |
| tccctgcagg ccgaggatgt ggcagtctat tactgtcagc acagttggga gattccctac | 360 | accttcggac aggggaccaa gctggaaatc aaac 394

<210> SEQ ID NO 28
<211> LENGTH: 131
<212> TYPE: PRT
<213> ORGANISM: Artificial sequence
<220> FEATURE:
<223> OTHER INFORMATION: Humanized VL

<400> SEQUENCE: 28

Met Glu Thr Asp Thr Leu Leu Leu Trp Val Leu Leu Trp Val Pro
1               5                   10                  15

Gly Ser Thr Gly Asp Ile Val Met Thr Gln Ser Pro Asp Ser Leu Ala
            20                  25                  30

Val Ser Leu Gly Glu Arg Ala Thr Ile Asn Cys Arg Ala Ser Gln Ser
        35                  40                  45

Val Ser Thr Ser Ser Tyr Ser Tyr Met His Trp Tyr Gln Gln Lys Pro
    50                  55                  60

Gly Gln Pro Pro Lys Leu Leu Ile Lys Tyr Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln His Ser Trp Glu Ile Pro Tyr Thr Phe Gly Gln Gly Thr Lys Leu
        115                 120                 125

Glu Ile Lys
    130

<210> SEQ ID NO 29
<211> LENGTH: 394
<212> TYPE: DNA
<213> ORGANISM: Artificial sequence
<220> FEATURE:
<223> OTHER INFORMATION: Hunanized VL

<400> SEQUENCE: 29
atggagacag acacactcct gctgtgggtg ctgctgctct gggttccagg ctccactggc     60
gacattgtgc tgacacagtc tcctgactcc ctggctgtgt ctctggggga gagggccacc    120
atcaactgca gggccagcca aagtgtcagt acatctagct atagttatat gcactggtac    180
caacagaaac caggacagcc acccaaactc ctcatcaagt atgcatccaa cctggaatct    240
ggggtccctg acagattcag tggcagtggg tctgggacag acttcaccct caccatcagc    300
tccctgcagg ccgaggatgt ggcagtctat tactgtcagc acagttggga gattccctac    360
accttcggag cgggaccaa gctggaaatc aaac    394

<210> SEQ ID NO 30
<211> LENGTH: 131
<212> TYPE: PRT
<213> ORGANISM: Artificial sequence
<220> FEATURE:
<223> OTHER INFORMATION: Humanized VL

<400> SEQUENCE: 30

Met Glu Thr Asp Thr Leu Leu Leu Trp Val Leu Leu Trp Val Pro
1               5                   10                  15

Gly Ser Thr Gly Asp Ile Val Leu Thr Gln Ser Pro Asp Ser Leu Ala
            20                  25                  30

Val Ser Leu Gly Glu Arg Ala Thr Ile Asn Cys Arg Ala Ser Gln Ser
           35                  40                  45

Val Ser Thr Ser Ser Tyr Ser Tyr Met His Trp Tyr Gln Gln Lys Pro
 50                  55                  60

Gly Gln Pro Pro Lys Leu Leu Ile Lys Tyr Ala Ser Asn Leu Glu Ser
65                  70                  75                  80

Gly Val Pro Asp Arg Phe Ser Gly Ser Gly Ser Gly Thr Asp Phe Thr
                 85                  90                  95

Leu Thr Ile Ser Ser Leu Gln Ala Glu Asp Val Ala Val Tyr Tyr Cys
            100                 105                 110

Gln His Ser Trp Glu Ile Pro Tyr Thr Phe Gly Gly Gly Thr Lys Leu
        115                 120                 125

Glu Ile Lys
    130

<210> SEQ ID NO 31
<211> LENGTH: 414
<212> TYPE: DNA
<213> ORGANISM: Artificial sequence
<220> FEATURE:
<223> OTHER INFORMATION: Humanized VH

<400> SEQUENCE: 31
atggaatgga actgggtcgt tctcttcctc ctgtcactga ctgcaggcgt ctattcccaa     60
gtgcagctcg tccagtctgg agctgaagtc aaaaagcctg ggcttcagt gaaagtctcc    120 tgcaaggctt ctggcttcac cttcagcagt agctatatca gttggttgag gcaggcccct    180
ggacagagac ttgagtggat tgcatggatt tatgctggaa ctggcggaac tagctataat    240
cagaagttca caggcaaggc cacactgact gtagacacat ccgccagcac agcctacatg    300
gaactcagca gcctgagatc tgaggacact gccgtctatt actgtgcaag acataaccct    360
cgttactatg ctatggacta ctggggccaa ggaaccacag tcaccgtctc ctca          414

<210> SEQ ID NO 32
<211> LENGTH: 138
<212> TYPE: PRT
<213> ORGANISM: Artificial sequence
<220> FEATURE:
<223> OTHER INFORMATION: Humanized VH

<400> SEQUENCE: 32

Met Glu Trp Asn Trp Val Val Leu Phe Leu Leu Ser Leu Thr Ala Gly
1               5                   10                  15

Val Tyr Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Ser Ser Tyr Ile Ser Trp Leu Arg Gln Ala Pro Gly Gln Arg Leu
    50                  55                  60

Glu Trp Ile Ala Trp Ile Tyr Ala Gly Thr Gly Gly Thr Ser Tyr Asn
65                  70                  75                  80

Gln Lys Phe Thr Gly Lys Ala Thr Leu Thr Val Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg His Asn Pro Arg Tyr Tyr Ala Met Asp Tyr Trp
        115                 120                 125

```
Gly Gln Gly Thr Thr Val Thr Val Ser Ser
        130                 135
```

<210> SEQ ID NO 33
<211> LENGTH: 414
<212> TYPE: DNA
<213> ORGANISM: Artificial sequence
<220> FEATURE:
<223> OTHER INFORMATION: Humanized VH

<400> SEQUENCE: 33

```
atggaatgga actgggtcgt tctcttcctc ctgtcactga ctgcaggcgt ctattcccaa    60
gtgcagctcg tccagtctgg agctgaagtc aaaaagcctg ggcttcagt gaaagtctcc    120
tgcaaggctt ctggcttcac cttcagcagt agctatatca gttggttgag gcaggcccct   180
ggacagagac ttgagtggat tgcatggatt tatgctggaa ctggcggaac tagctataat   240
cagaagttca caggcagagt cacactgact gtagacacat ccgccagcac agcctacatg   300
gaactcagca gcctgagatc tgaggacact gccgtctatt actgtgcaag acataaccct   360
cgttactatg ctatggacta ctggggccaa ggaaccacag tcaccgtctc ctca          414
```

<210> SEQ ID NO 34
<211> LENGTH: 138
<212> TYPE: PRT
<213> ORGANISM: Artificial sequence
<220> FEATURE:
<223> OTHER INFORMATION: Humanized VH

<400> SEQUENCE: 34

```
Met Glu Trp Asn Trp Val Val Leu Phe Leu Leu Ser Leu Thr Ala Gly
1               5                   10                  15

Val Tyr Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Ser Ser Tyr Ile Ser Trp Leu Arg Gln Ala Pro Gly Gln Arg Leu
    50                  55                  60

Glu Trp Ile Ala Trp Ile Tyr Ala Gly Thr Gly Gly Thr Ser Tyr Asn
65                  70                  75                  80

Gln Lys Phe Thr Gly Arg Val Thr Leu Thr Val Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg His Asn Pro Arg Tyr Tyr Ala Met Asp Tyr Trp
        115                 120                 125

Gly Gln Gly Thr Thr Val Thr Val Ser Ser
        130                 135
```

<210> SEQ ID NO 35
<211> LENGTH: 382
<212> TYPE: DNA
<213> ORGANISM: Artificial sequence
<220> FEATURE:
<223> OTHER INFORMATION: Humanized VL

<400> SEQUENCE: 35

```
atgttctcac tggctctgct cctcagtctg ctgctcctct gtgtctctga ttctagagca    60
gacatccaga tgacccagtc tccaagctcc ctgtccgcca gcgtgggaga tagagtcacc   120
atcacatgca tcaccagcac tgatattgat gatgatatga actggtacca gcagaagcca   180
```

```
gggaaagctc ctaagctcct gatttcagaa ggcaatactc tgcgccctgg agtcccatcc      240
cgattctccg gcagtggcta tggaacagat tttaccttta caattagctc cctgcagcca      300
gaagatattg caacctacta ctgtttgcaa agtgataacc tgccctacac cttcggaggg      360
gggaccaaag tcgaaatcaa ac                                                382
```

<210> SEQ ID NO 36
<211> LENGTH: 127
<212> TYPE: PRT
<213> ORGANISM: Artificial sequence
<220> FEATURE:
<223> OTHER INFORMATION: Humanized VL

<400> SEQUENCE: 36

```
Met Phe Ser Leu Ala Leu Leu Leu Ser Leu Leu Leu Leu Cys Val Ser
1               5                   10                  15

Asp Ser Arg Ala Asp Ile Gln Met Thr Gln Ser Pro Ser Ser Leu Ser
            20                  25                  30

Ala Ser Val Gly Asp Arg Val Thr Ile Thr Cys Ile Thr Ser Thr Asp
        35                  40                  45

Ile Asp Asp Asp Met Asn Trp Tyr Gln Gln Lys Pro Gly Lys Ala Pro
    50                  55                  60

Lys Leu Leu Ile Ser Glu Gly Asn Thr Leu Arg Pro Gly Val Pro Ser
65                  70                  75                  80

Arg Phe Ser Gly Ser Gly Tyr Gly Thr Asp Phe Thr Phe Thr Ile Ser
                85                  90                  95

Ser Leu Gln Pro Glu Asp Ile Ala Thr Tyr Tyr Cys Leu Gln Ser Asp
            100                 105                 110

Asn Leu Pro Tyr Thr Phe Gly Gly Gly Thr Lys Val Glu Ile Lys
        115                 120                 125
```

<210> SEQ ID NO 37
<211> LENGTH: 382
<212> TYPE: DNA
<213> ORGANISM: Artificial sequence
<220> FEATURE:
<223> OTHER INFORMATION: Humanized VL

<400> SEQUENCE: 37

```
atgttctcac tggctctgct cctcagtctg ctgctcctct gtgtctctga ttctagagca      60
gacatccaga tgacccagtc tccaagctcc ctgtccgcca gcgtgggaga tagagtcacc      120
atcacatgca tcaccagcac tgatattgat gatgatatga actggtacca gcagaagcca      180
gggaaagctc ctaagctcct gatttcagaa ggcaatactc tgcgccctgg agtcccatcc      240
cgattctccg gcagtggctc tggaacagat tttaccttta caattagctc cctgcagcca      300
gaagatattg caacctacta ctgtttgcaa agtgataacc tgccctacac cttcggaggg      360
gggaccaaag tcgaaatcaa ac                                                382
```

<210> SEQ ID NO 38
<211> LENGTH: 127
<212> TYPE: PRT
<213> ORGANISM: Artificial sequence
<220> FEATURE:
<223> OTHER INFORMATION: Humanized VL

<400> SEQUENCE: 38

```
Met Phe Ser Leu Ala Leu Leu Leu Ser Leu Leu Leu Leu Cys Val Ser
1               5                   10                  15
```

```
Asp Ser Arg Ala Asp Ile Gln Met Thr Gln Ser Pro Ser Ser Leu Ser
            20                  25                  30

Ala Ser Val Gly Asp Arg Val Thr Ile Thr Cys Ile Thr Ser Thr Asp
            35                  40                  45

Ile Asp Asp Asp Met Asn Trp Tyr Gln Gln Lys Pro Gly Lys Ala Pro
 50                  55                  60

Lys Leu Leu Ile Ser Glu Gly Asn Thr Leu Arg Pro Gly Val Pro Ser
 65                  70                  75                  80

Arg Phe Ser Gly Ser Gly Ser Gly Thr Asp Phe Thr Phe Thr Ile Ser
                85                  90                  95

Ser Leu Gln Pro Glu Asp Ile Ala Thr Tyr Tyr Cys Leu Gln Ser Asp
            100                 105                 110

Asn Leu Pro Tyr Thr Phe Gly Gly Gly Thr Lys Val Glu Ile Lys
            115                 120                 125
```

<210> SEQ ID NO 39
<211> LENGTH: 382
<212> TYPE: DNA
<213> ORGANISM: Artificial sequence
<220> FEATURE:
<223> OTHER INFORMATION: Humanized VL

<400> SEQUENCE: 39

```
atgttctcac tggctctgct cctcagtctg ctgctcctct gtgtctctga ttctagagca    60
gacacccaga tgacccagtc tccaagctcc ctgtccgcca gcgtgggaga tagagtcacc   120
atcacatgca tcaccagcac tgatattgat gatgatatga actggtacca gcagaagcca   180
gggaaagctc ctaagctcct gatttcagaa ggcaatactc tgcgccctgg agtcccatcc   240
cgattctccg gcagtggcta tggaacagat tttacccttta caattagctc cctgcagcca   300
gaagatattg caacctacta ctgtttgcaa agtgataacc tgccctacac cttcggaggg   360
gggaccaaag tcgaaatcaa ac                                            382
```

<210> SEQ ID NO 40
<211> LENGTH: 127
<212> TYPE: PRT
<213> ORGANISM: Artificial sequence
<220> FEATURE:
<223> OTHER INFORMATION: Humanized VL

<400> SEQUENCE: 40

```
Met Phe Ser Leu Ala Leu Leu Leu Ser Leu Leu Leu Cys Val Ser
 1               5                  10                  15

Asp Ser Arg Ala Asp Thr Gln Met Thr Gln Ser Pro Ser Ser Leu Ser
            20                  25                  30

Ala Ser Val Gly Asp Arg Val Thr Ile Thr Cys Ile Thr Ser Thr Asp
            35                  40                  45

Ile Asp Asp Asp Met Asn Trp Tyr Gln Gln Lys Pro Gly Lys Ala Pro
 50                  55                  60

Lys Leu Leu Ile Ser Glu Gly Asn Thr Leu Arg Pro Gly Val Pro Ser
 65                  70                  75                  80

Arg Phe Ser Gly Ser Gly Tyr Gly Thr Asp Phe Thr Phe Thr Ile Ser
                85                  90                  95

Ser Leu Gln Pro Glu Asp Ile Ala Thr Tyr Tyr Cys Leu Gln Ser Asp
            100                 105                 110

Asn Leu Pro Tyr Thr Phe Gly Gly Gly Thr Lys Val Glu Ile Lys
            115                 120                 125
```

<210> SEQ ID NO 41
<211> LENGTH: 1398
<212> TYPE: DNA
<213> ORGANISM: Artificial sequence
<220> FEATURE:
<223> OTHER INFORMATION: Humanized IgG

<400> SEQUENCE: 41

```
atggaatgga gcggggtctt tatctttctc ctgtcagtga ctgcaggcgt ccactcccaa      60
gtccagctcg tgcagtctgg agctgaagtg aagaaacctg gggcttcagt gaaggtgtcc     120
tgcaaggctt ctggatacac cttcactaac tactggatcg gatgggtcaa acaggccct     180
ggacagggcc tcgagtggat tggagatatt accctggag gaggctatac taactacaat     240
gagaagttca agggcagagc cacactgact gcagacacat ccgccagcac agcctacatg     300
gagctcagca gcctgagatc tgaggacact gccgtgtatt actgtgcaag gaactgga      360
ggcggagact actggggcca agggactctg gtcactgtct cttcagcctc caccaagggc     420
ccatcggtct tccccctggc accctcctcc aagagcacct ctgggggcac agcggccctg     480
ggctgcctgg tcaaggacta cttccccgaa ccggtgacgg tgtcgtggaa ctcaggcgcc     540
ctgaccagcg gcgtgcacac cttcccggct gtcctacagt cctcaggact ctactccctc     600
agcagcgtgg tgaccgtgcc ctccagcagc ttgggcaccc agacctacat ctgcaacgtg     660
aatcacaagc ccagcaacac caaggtggac aagaaagttg agcccaaatc ttgtgacaaa     720
actcacacat gcccaccgtg cccagcacct gaactcctgg ggggaccgtc agtcttcctc     780
ttccccccaa aacccaagga caccctcatg atctcccgga cccctgaggt cacatgcgtg     840
gtggtggacg tgagccacga agaccctgag gtcaagttca actggtacgt ggacggcgtg     900
gaggtgcata atgccaagac aaagccgcgg gaggagcagt acaacagcac gtaccgtgtg     960
gtcagcgtcc tcaccgtcct gcaccaggac tggctgaatg gcaaggagta caagtgcaag    1020
gtctccaaca aagccctccc agcccccatc gagaaaacca tctccaaagc caaagggcag    1080
ccccgagaac acaggtgta cccctgcccc catcccggg atgagctgac caagaaccag    1140
gtcagcctga cctgcctggt caaaggcttc tatcccagcg acatcgccgt ggagtgggag    1200
agcaatgggc agccggagaa caactacaag accacgcctc ccgtgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaatga                                                  1398
```

<210> SEQ ID NO 42
<211> LENGTH: 465
<212> TYPE: PRT
<213> ORGANISM: Artificial sequence
<220> FEATURE:
<223> OTHER INFORMATION: Humanized IgG

<400> SEQUENCE: 42

```
Met Glu Trp Ser Gly Val Phe Ile Phe Leu Leu Ser Val Thr Ala Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asn Tyr Trp Ile Gly Trp Val Lys Gln Ala Pro Gly Gln Gly Leu
```

```
            50                  55                  60
Glu Trp Ile Gly Asp Ile Tyr Pro Gly Gly Gly Tyr Thr Asn Tyr Asn
 65                  70                  75                  80

Glu Lys Phe Lys Gly Arg Ala Thr Leu Thr Ala Asp Thr Ser Ala Ser
                 85                  90                  95

Thr Ala Tyr Met Glu Leu Ser Ser Leu Arg Ser Glu Asp Thr Ala Val
                100                 105                 110

Tyr Tyr Cys Ala Arg Gly Thr Gly Gly Asp Tyr Trp Gly Gln Gly
                115                 120                 125

Thr Leu Val Thr Val Ser Ser Ala Ser Thr Lys Gly Pro Ser Val Phe
                130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
                180                 185                 190

Gln Ser Ser Gly Leu Tyr Ser Leu Ser Ser Val Val Thr Val Pro Ser
                195                 200                 205

Ser Ser Leu Gly Thr Gln Thr Tyr Ile Cys Asn Val Asn His Lys Pro
210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser His Glu Asp
                275                 280                 285

Pro Glu Val Lys Phe Asn Trp Tyr Val Asp Gly Val Glu Val His Asn
                290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
                340                 345                 350

Thr Ile Ser Lys Ala Lys Gly Gln Pro Arg Glu Pro Gln Val Tyr Thr
                355                 360                 365

Leu Pro Pro Ser Arg Asp Glu Leu Thr Lys Asn Gln Val Ser Leu Thr
                370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
                420                 425                 430

Ser Arg Trp Gln Gln Gly Asn Val Phe Ser Cys Ser Val Met His Glu
                435                 440                 445

Ala Leu His Asn His Tyr Thr Gln Lys Ser Leu Ser Leu Ser Pro Gly
                450                 455                 460

Lys
465
```

<210> SEQ ID NO 43
<211> LENGTH: 717
<212> TYPE: DNA
<213> ORGANISM: Artificial sequence
<220> FEATURE:
<223> OTHER INFORMATION: Humanized IgG

<400> SEQUENCE: 43

```
atggagacag acacactcct gctgtgggtg ctgctgctct gggttccagg ctccactggc      60
gacattgtgc tgacacagtc tcctgactcc ctggctgtgt ctctggggga gagggccacc     120
atcaactgca gggccagcca aagtgtcagt acatctagct atagttatat gcactggtac     180
caacagaaac caggacagcc acccaaactc ctcatcaagt atgcatccaa cctggaatct     240
ggggtccctg acagattcag tgcagtgggt tctgggacag acttcaccct caccatcagc     300
tccctgcagg ccgaggatgt ggcagtctat tactgtcagc acagttggga gattccctac     360
accttcggag cgggaccaa gctggaaatc aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc     660
acccatcagg gcctgagctc gcccgtcaca aagagcttca caggggaga gtgttag        717
```

<210> SEQ ID NO 44
<211> LENGTH: 238
<212> TYPE: PRT
<213> ORGANISM: Artificial sequence
<220> FEATURE:
<223> OTHER INFORMATION: Humanized IgG

<400> SEQUENCE: 44

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Asp Ser Leu Ala
            20                  25                  30

Val Ser Leu Gly Glu Arg Ala Thr Ile Asn Cys Arg Ala Ser Gln Ser
        35                  40                  45

Val Ser Thr Ser Ser Tyr Ser Tyr Met His Trp Tyr Gln Gln Lys Pro
    50                  55                  60

Gly Gln Pro Pro Lys Leu Leu Ile Lys Tyr Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln His Ser Trp Glu Ile Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser 180                 185                  190
Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 45
<211> LENGTH: 1407
<212> TYPE: DNA
<213> ORGANISM: Artificial sequence
<220> FEATURE:
<223> OTHER INFORMATION: Humanized IgG

<400> SEQUENCE: 45

```
atggaatgga actgggtcgt tctcttcctc ctgtcactga ctgcaggcgt ctattcccaa      60
gtgcagctcg tccagtctgg agctgaagtc aaaaagcctg ggcttcagt gaaagtctcc     120
tgcaaggctt ctggcttcac cttcagcagt agctatatca gttggttgag gcaggcccct    180
ggacagagac ttgagtggat tgcatggatt tatgctggaa ctggcggaac tagctataat    240
cagaagttca caggcaaggc cacactgact gtagacacat ccgccagcac agcctacatg    300
gaactcagca gcctgagatc tgaggacact gccgtctatt actgtgcaag acataaccct    360
cgttactatg ctatggacta ctggggccaa ggaaccacag tcaccgtctc ctcagcctcc    420
accaagggcc catcggtctt ccccctggca ccctcctcca agagcacctc tgggggcaca    480
gcggccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct gggcaccca gacctacatc    660
tgcaacgtga atcacaagcc cagcaacacc aaggtggaca gaaagttga gcccaaatct    720
tgtgacaaaa ctcacacatg cccaccgtgc ccagcacctg aactcctggg gggaccgtca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca aagccgcggg aggagcagta caacagcacg    960
taccgtgtgg tcagcgtcct caccgtcctg caccaggact ggctgaatgg caaggagtac   1020
aagtgcaagg tctccaacaa agccctccca gcccccatcg agaaaccat ctccaaagcc   1080
aaagggcagc cccgagaacc acaggtgtac accctgcccc catcccggga tgagctgacc   1140
aagaaccagg tcagcctgac ctgcctggtc aaaggcttct atcccagcga catcgccgtg   1200
gagtgggaga gcaatgggca gccggagaac aactacaaga ccacgcctcc cgtgctggac   1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaatga                                      1407
```

<210> SEQ ID NO 46
<211> LENGTH: 468
<212> TYPE: PRT
<213> ORGANISM: Artificial sequence
<220> FEATURE:
<223> OTHER INFORMATION: Humanized IgG

<400> SEQUENCE: 46

```
Met Glu Trp Asn Trp Val Val Leu Phe Leu Ser Leu Thr Ala Gly
1               5                   10                  15

Val Tyr Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
            35                  40                  45

Ser Ser Ser Tyr Ile Ser Trp Leu Arg Gln Ala Pro Gly Gln Arg Leu
50                  55                  60

Glu Trp Ile Ala Trp Ile Tyr Ala Gly Thr Gly Thr Ser Tyr Asn
65                  70                  75                  80

Gln Lys Phe Thr Gly Lys Ala Thr Leu Thr Val Asp Thr Ser Ala Ser
            85                  90                  95

Thr Ala Tyr Met Glu Leu Ser Ser Leu Arg Ser Glu Asp Thr Ala Val
            100                 105                 110

Tyr Tyr Cys Ala Arg His Asn Pro Arg Tyr Tyr Ala Met Asp Tyr Trp
            115                 120                 125

Gly Gln Gly Thr Thr Val Thr Val Ser Ser Ala Ser Thr Lys Gly Pro
            130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
            165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Val Val Thr
            195                 200                 205

Val Pro Ser Ser Ser Leu Gly Thr Gln Thr Tyr Ile Cys Asn Val Asn
210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
            245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
            290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
```

```
                420             425             430
Val Asp Lys Ser Arg Trp Gln Gln Gly Asn Val Phe Ser Cys Ser Val
            435             440             445

Met His Glu Ala Leu His Asn His Tyr Thr Gln Lys Ser Leu Ser Leu
    450             455             460

Ser Pro Gly Lys
465
```

<210> SEQ ID NO 47
<211> LENGTH: 705
<212> TYPE: DNA
<213> ORGANISM: Artificial sequence
<220> FEATURE:
<223> OTHER INFORMATION: Humanized IgG

<400> SEQUENCE: 47

```
atgttctcac tggctctgct cctcagtctg ctgctcctct gtgtctctga ttctagagca      60
gacacccaga tgacccagtc tccaagctcc ctgtccgcca gcgtgggaga tagagtcacc     120
atcacatgca tcaccagcac tgatattgat gatgatatga actggtacca gcagaagcca     180
gggaaagctc ctaagctcct gatttcagaa ggcaatactc tgcgccctgg agtcccatcc     240
cgattctccg gcagtggcta tggaacagat tttacctttá caattagctc cctgcagcca     300
gaagatattg caacctacta ctgtttgcaa agtgataacc tgccctacac cttcggaggg     360
gggaccaaag tcgaaatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga aaacacaaa gtctacgcct gcgaagtcac ccatcagggc     660
ctgagctcgc ccgtcacaaa gagcttcaac aggggagagt gttag                    705
```

<210> SEQ ID NO 48
<211> LENGTH: 234
<212> TYPE: PRT
<213> ORGANISM: Artificial sequence
<220> FEATURE:
<223> OTHER INFORMATION: Humanized IgG

<400> SEQUENCE: 48

```
Met Phe Ser Leu Ala Leu Leu Ser Leu Leu Leu Cys Val Ser
1               5                   10                  15

Asp Ser Arg Ala Asp Thr Gln Met Thr Gln Ser Pro Ser Ser Leu Ser
                20                  25                  30

Ala Ser Val Gly Asp Arg Val Thr Ile Thr Cys Ile Thr Ser Thr Asp
            35                  40                  45

Ile Asp Asp Asp Met Asn Trp Tyr Gln Gln Lys Pro Gly Lys Ala Pro
        50                  55                  60

Lys Leu Leu Ile Ser Glu Gly Asn Thr Leu Arg Pro Gly Val Pro Ser
65                  70                  75                  80

Arg Phe Ser Gly Ser Gly Tyr Gly Thr Asp Phe Thr Phe Thr Ile Ser
                85                  90                  95

Ser Leu Gln Pro Glu Asp Ile Ala Thr Tyr Tyr Cys Leu Gln Ser Asp
                100                 105                 110

Asn Leu Pro Tyr Thr Phe Gly Gly Gly Thr Lys Val Glu Ile Lys Arg
            115                 120                 125
```

```
Thr Val Ala Ala Pro Ser Val Phe Ile Phe Pro Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
210                 215                 220
Val Thr Lys Ser Phe Asn Arg Gly Glu Cys
225                 230
```

<210> SEQ ID NO 49
<211> LENGTH: 1407
<212> TYPE: DNA
<213> ORGANISM: Artificial sequence
<220> FEATURE:
<223> OTHER INFORMATION: Humanized IgG

<400> SEQUENCE: 49

| | | |
|---|---|---|
| atggaatgga actgggtcgt tctcttcctc ctgtcactga ctgcaggcgt ctattcccaa | 60 |
| gtgcagctcg tccagtctgg agctgaagtc aaaaagcctg ggcttcagt gaaagtctcc | 120 |
| tgcaaggctt ctggcttcac cttcagcagt agctatatca gttggttgag gcaggcccct | 180 |
| ggacagagac ttgagtggat tgcatggatt tatgctggaa ctggcggaac tagctataat | 240 |
| cagaagttca caggcagagt cacactgact gtagacacat ccgccagcac agcctacatg | 300 |
| gaactcagca gcctgagatc tgaggacact gccgtctatt actgtgcaag acataaccct | 360 |
| cgttactatg ctatggacta ctggggccaa ggaaccacag tcaccgtctc ctcagcctcc | 420 |
| accaagggcc catcggtctt ccccctggca ccctcctcca gagcacctc tgggggcaca | 480 |
| gcggccctgg gctgcctggt caaggactac ttccccgaac cggtgacggt gtcgtggaac | 540 |
| tcaggcgccc tgaccagcgg cgtgcacacc ttcccggctg tcctacagtc ctcaggactc | 600 |
| tactccctca gcagcgtggt gaccgtgccc tccagcagct gggcaccca gacctacatc | 660 |
| tgcaacgtga atcacaagcc cagcaacacc aaggtggaca gaaagttga gcccaaatct | 720 |
| tgtgacaaaa ctcacacatg cccaccgtgc ccagcacctg aactcctggg gggaccgtca | 780 |
| gtcttcctct tccccccaaa acccaaggac accctcatga tctcccggac ccctgaggtc | 840 |
| acatgcgtgg tggtggacgt gagccacgaa gaccctgagg tcaagttcaa ctggtacgtg | 900 |
| gacggcgtgg aggtgcataa tgccaagaca agccgcggg aggagcagta acagcacg | 960 |
| taccgtgtgg tcagcgtcct caccgtcctg caccaggact ggctgaatgg caaggagtac | 1020 |
| aagtgcaagg tctccaacaa agccctccca gcccccatcg agaaaaccat ctccaaagcc | 1080 |
| aaagggcagc cccgagaacc acaggtgtac accctgcccc catcccggga tgagctgacc | 1140 |
| aagaaccagg tcagcctgac ctgcctggtc aaaggcttct atcccagcga catcgccgtg | 1200 |
| gagtgggaga gcaatgggca gccggagaac aactacaaga ccacgcctcc cgtgctggac | 1260 |
| tccgacggct ccttcttcct ctacagcaag ctcaccgtgg acaagagcag gtggcagcag | 1320 |
| gggaacgtct tctcatgctc cgtgatgcat gaggctctgc acaaccacta cacgcagaag | 1380 |
| agcctctccc tgtctccggg taaatga | 1407 |

```
<210> SEQ ID NO 50
<211> LENGTH: 468
<212> TYPE: PRT
<213> ORGANISM: Artificial sequence
<220> FEATURE:
<223> OTHER INFORMATION: Humanized IgG

<400> SEQUENCE: 50

Met Glu Trp Asn Trp Val Val Leu Phe Leu Leu Ser Leu Thr Ala Gly
1               5                   10                  15

Val Tyr Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Thr Phe
        35                  40                  45

Ser Ser Ser Tyr Ile Ser Trp Leu Arg Gln Ala Pro Gly Gln Arg Leu
    50                  55                  60

Glu Trp Ile Ala Trp Ile Tyr Ala Gly Thr Gly Gly Thr Ser Tyr Asn
65                  70                  75                  80

Gln Lys Phe Thr Gly Arg Val Thr Leu Thr Val Asp Thr Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg His Asn Pro Arg Tyr Tyr Ala Met Asp Tyr Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365
```

-continued

```
Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 51
<211> LENGTH: 21
<212> TYPE: DNA
<213> ORGANISM: Artificial sequence
<220> FEATURE:
<223> OTHER INFORMATION: oligonucleotide

<400> SEQUENCE: 51
tacaccttca ctaactactg g                                              21

<210> SEQ ID NO 52
<211> LENGTH: 18
<212> TYPE: DNA
<213> ORGANISM: Artificial sequence
<220> FEATURE:
<223> OTHER INFORMATION: oligonucleotide

<400> SEQUENCE: 52
cccagttcct ctgcacag                                                  18

<210> SEQ ID NO 53
<211> LENGTH: 20
<212> TYPE: DNA
<213> ORGANISM: Artificial sequence
<220> FEATURE:
<223> OTHER INFORMATION: oligonucleotide

<400> SEQUENCE: 53
gccagtggat agactgatgg                                                20

<210> SEQ ID NO 54
<211> LENGTH: 20
<212> TYPE: DNA
<213> ORGANISM: Artificial sequence
<220> FEATURE:
<223> OTHER INFORMATION: oligonucleotide

<400> SEQUENCE: 54
agccaaagtg tcagtacatc                                                20

<210> SEQ ID NO 55
<211> LENGTH: 29
<212> TYPE: DNA
<213> ORGANISM: Artificial sequence
<220> FEATURE:
<223> OTHER INFORMATION: oligonucleotide

<400> SEQUENCE: 55
```
ctccctctaa cactcattcc tgttgaagc          29

```
<210> SEQ ID NO 56
<211> LENGTH: 19
<212> TYPE: DNA
<213> ORGANISM: Artificial sequence
<220> FEATURE:
<223> OTHER INFORMATION: oligonucleotide

<400> SEQUENCE: 56
```
gaatctcccg actgtgctg                     19

```
<210> SEQ ID NO 57
<211> LENGTH: 443
<212> TYPE: DNA
<213> ORGANISM: Artificial sequence
<220> FEATURE:
<223> OTHER INFORMATION: Synthetic gene

<400> SEQUENCE: 57
```
actagtgcca ccatggaatg gagcggggtc tttatctttc tcctgtcagt gactgcaggc    60
gtccactccc aagtccagct ccagcagtct ggagctgagc tcgtgaggcc tgggacttca   120
gtgaagatgt cctgcaaggc tgctggatac accttcacta actactggat cgatgggtg    180 aagcagaggc ctggacatgg cctcgagtgg attggagata tttaccctgg aggaggctat   240
actaactaca tgagaagtt caagggcaag gccacactga ctgcagacac atcctccagc    300
acagcctaca tgcagctcag cagcctgaca tctgaggact ctgccatcta ttactgtgca   360
agaggaactg gaggcggaga ctactggggc caagggactc tggtcactgt ctctgcaggt   420
gagtcctaac ttctcccaag ctt                                           443

```
<210> SEQ ID NO 58
<211> LENGTH: 430
<212> TYPE: DNA
<213> ORGANISM: Artificial sequence
<220> FEATURE:
<223> OTHER INFORMATION: Synthetic gene

<400> SEQUENCE: 58
```
gctagcgcca ccatggagac agacacactc ctgctgtggg tgctgctgct ctgggttcca    60
ggctccactg gcgacattgt gctgacacag tctcctgctt ccctggctgt gtctctgggg   120
cagagggcca ccatctcatg cagggccagc caaagtgtca gtacatctag ctatagttat   180
atgcactggt accaacagaa accaggacag ccacccaaac tcctcatcaa gtatgcatcc   240
aacctggaat ctggggtccc tgccagattc agtggcagtg gtctgggac agacttcacc    300 ctcaacatcc atcctgtgga ggaggaggat actgcaacat attactgtca gcacagttgg   360
gagattccct acaccttcgg aggggggacc aagctggaaa tcaaacgtaa gtagtcttct   420
caacgaattc                                                          430

```
<210> SEQ ID NO 59
<211> LENGTH: 443
<212> TYPE: DNA
<213> ORGANISM: Artificial sequence
<220> FEATURE:
<223> OTHER INFORMATION: Synthetic gene

<400> SEQUENCE: 59
```
actagtgcca ccatggaatg gagcggggtc tttatctttc tcctgtcagt gactgcaggc    60
gtccactccc aagtccagct cgtgcagtct ggagctgaag tgaagaaacc tggggcttca   120

```
gtgaaggtgt cctgcaaggc ttctggatac accttcacta actactggat cggatgggtc    180
agacaggccc ctggacaggg cctcgagtgg attggagata tttaccctgg aggaggctat    240
actaactaca atgagaagtt caagggcaga gccacactga ctgcagacac atccgccagc    300
acagcctaca tggagctcag cagcctgaga tctgaggaca ctgccgtgta ttactgtgca    360
agaggaactg gaggcggaga ctactggggc caagggactc tggtcactgt ctcttcaggt    420
gagtcctaac ttctcccaag ctt                                            443

<210> SEQ ID NO 60
<211> LENGTH: 443
<212> TYPE: DNA
<213> ORGANISM: Artificial sequence
<220> FEATURE:
<223> OTHER INFORMATION: Synthetic gene

<400> SEQUENCE: 60
actagtgcca ccatggaatg gagcggggtc tttatctttc tcctgtcagt gactgcaggc     60
gtccactccc aagtccagct cgtgcagtct ggagctgaag tgaagaaacc tggggcttca    120
gtgaaggtgt cctgcaaggc ttctggatac accttcacta actactggat cggatgggtc    180
agacaggccc ctggacaggg cctcgagtgg attggagata tttaccctgg aggaggctat    240
actaactaca atgagaagtt caagggcaga gccacactga ctgcagacac atccaccagc    300
acagcctaca tggagctcag cagcctgaga tctgaggaca ctgccgtgta ttactgtgca    360
agaggaactg gaggcggaga ctactggggc caagggactc tggtcactgt ctcttcaggt    420
gagtcctaac ttctcccaag ctt                                            443

<210> SEQ ID NO 61
<211> LENGTH: 430
<212> TYPE: DNA
<213> ORGANISM: Artificial sequence
<220> FEATURE:
<223> OTHER INFORMATION: Synthetic gene

<400> SEQUENCE: 61
gctagcgcca ccatggagac agacacactc ctgctgtggg tgctgctgct ctgggttcca     60
ggctccactg gcgacattgt gatgacacag tctcctgact ccctggctgt gtctctgggg    120
gagagggcca ccatcaactg cagggccagc caaagtgtca gtacatctag ctatagttat    180
atgcactggt accaacagaa accaggacag ccacccaaac tcctcatcaa gtatgcatcc    240
aacctggaat ctggggtccc tgacagattc agtggcagtg gtctgggac agacttcacc     300 ctcaccatca gctccctgca ggccgaggat gtggcagtct attactgtca gcacagttgg    360
gagattccct acaccttcgg acaggggacc aagctggaaa tcaaacgtaa gtagtcttct    420
caacgaattc                                                           430

<210> SEQ ID NO 62
<211> LENGTH: 24
<212> TYPE: DNA
<213> ORGANISM: Artificial sequence
<220> FEATURE:
<223> OTHER INFORMATION: oligonucleotide

<400> SEQUENCE: 62
gaaccgtcag atcgcctgga gacg                                            24

<210> SEQ ID NO 63
```

```
<211> LENGTH: 20
<212> TYPE: DNA
<213> ORGANISM: Artificial sequence
<220> FEATURE:
<223> OTHER INFORMATION: oligonucleotide

<400> SEQUENCE: 63
tgaaagatga gctggaggac                                              20

<210> SEQ ID NO 64
<211> LENGTH: 20
<212> TYPE: DNA
<213> ORGANISM: Artificial sequence
<220> FEATURE:
<223> OTHER INFORMATION: oligonucleotide

<400> SEQUENCE: 64
ctttcttgtc caccttggtg                                              20

<210> SEQ ID NO 65
<211> LENGTH: 17
<212> TYPE: DNA
<213> ORGANISM: Artificial sequence
<220> FEATURE:
<223> OTHER INFORMATION: oligonucleotide

<400> SEQUENCE: 65
gctgtcctac agtcctc                                                 17

<210> SEQ ID NO 66
<211> LENGTH: 18
<212> TYPE: DNA
<213> ORGANISM: Artificial sequence
<220> FEATURE:
<223> OTHER INFORMATION: oligonucleotide

<400> SEQUENCE: 66
acgtgccaag catcctcg                                                18

<210> SEQ ID NO 67
<211> LENGTH: 443
<212> TYPE: DNA
<213> ORGANISM: Artificial sequence
<220> FEATURE:
<223> OTHER INFORMATION: Synthetic gene

<400> SEQUENCE: 67
actagtgcca ccatggaatg gagcggggtc tttatctttc tcctgtcagt gactgcaggc     60
gtccactccc aagtccagct cgtgcagtct ggagctgaag tgaagaaacc tggggcttca    120
gtgaaggtgt cctgcaaggc ttctggatac accttcacta actactgat cggatgggtc    180 agacaggccc ctggacaggg cctcgagtgg attggagata tttaccctgg aggaggctat    240
actaactaca atgagaagtt caagggcaga gccacactga ctgcagacac atccaccagc    300
acagcctaca tggagctcag cagcctgaga tctgaggaca ctgccgtgta ttactgtgca    360
agaggaactg gaggcggaga ctactggggc caagggactc tggtcactgt ctcttcaggt    420
gagtcctaac ttctcccaag ctt                                           443

<210> SEQ ID NO 68
<211> LENGTH: 430
<212> TYPE: DNA
<213> ORGANISM: Artificial sequence
<220> FEATURE:
<223> OTHER INFORMATION: Synthetic gene
```

<400> SEQUENCE: 68

```
gctagcgcca ccatggagac agacacactc ctgctgtggg tgctgctgct ctgggttcca    60
ggctccactg gcgacattgt gctgacacag tctcctgact ccctggctgt gtctctgggg   120
gagagggcca ccatcaactg cagggccagc caaagtgtca gtacatctag ctatagttat   180
atgcactggt accaacagaa accaggacag ccacccaaac tcctcatcaa gtatgcatcc   240
aacctggaat ctggggtccc tgacagattc agtggcagtg gtctgggac agacttcacc    300
ctcaccatca gctccctgca ggccgaggat gtggcagtct attactgtca gcacagttgg   360
gagattccct acaccttcgg aggcgggacc aagctggaaa tcaaacgtaa gtagtcttct   420
caacgaattc                                                          430
```

<210> SEQ ID NO 69
<211> LENGTH: 20
<212> TYPE: DNA
<213> ORGANISM: Artificial sequence
<220> FEATURE:
<223> OTHER INFORMATION: oligonucleotide

<400> SEQUENCE: 69

```
gccagtggat agaccgatgg                                                20
```

<210> SEQ ID NO 70
<211> LENGTH: 19
<212> TYPE: DNA
<213> ORGANISM: Artificial sequence
<220> FEATURE:
<223> OTHER INFORMATION: oligonucleotide

<400> SEQUENCE: 70

```
accagcactg atattgatg                                                 19
```

<210> SEQ ID NO 71
<211> LENGTH: 20
<212> TYPE: DNA
<213> ORGANISM: Artificial sequence
<220> FEATURE:
<223> OTHER INFORMATION: oligonucleotide

<400> SEQUENCE: 71

```
cgtgtacggc aagttatcac                                                20
```

<210> SEQ ID NO 72
<211> LENGTH: 449
<212> TYPE: DNA
<213> ORGANISM: Artificial sequence
<220> FEATURE:
<223> OTHER INFORMATION: Synthetic gene

<400> SEQUENCE: 72

```
actagtacca ccatggaatg gaactgggtc gttctcttcc tcctgtcatt aactgcaggt    60
gtctattccc agggtcagat gcagcagtct ggagctgagc tggtgaagcc tggggcttca   120
gtgaagctgt cctgcaagac ttctggcttc accttcagca gtagctatat aagttggttg   180
aagcagaagc ctcgacagag tcttgagtgg attgcatgga tttatgctgg aactggtggt   240
actagctata atcagaagtt cacaggcaag gcccaactga ctgtagacac atcctccagc   300
acagcctaca tgcaactcag cagcctgaca tctgaggact ctgccatcta ttactgtgca   360
agacataacc ctcgttacta tgctatggac tactggggtc aaggaacctc agtcaccgtc   420
```
tcctcaggta agaatggcct ctcaagctt                                    449

<210> SEQ ID NO 73
<211> LENGTH: 33
<212> TYPE: DNA
<213> ORGANISM: Artificial sequence
<220> FEATURE:
<223> OTHER INFORMATION: oligonucleotide

<400> SEQUENCE: 73
gcaactagta ccaccatgga atggaactgg gtc                               33

<210> SEQ ID NO 74
<211> LENGTH: 47
<212> TYPE: DNA
<213> ORGANISM: Artificial sequence
<220> FEATURE:
<223> OTHER INFORMATION: oligonucleotide

<400> SEQUENCE: 74
gggaagcttg agaggccatt cttacctgag gagacggtga ctgaggt                47

<210> SEQ ID NO 75
<211> LENGTH: 416
<212> TYPE: DNA
<213> ORGANISM: Artificial sequence
<220> FEATURE:
<223> OTHER INFORMATION: Synthetic gene

<400> SEQUENCE: 75
gctagcacca ccatgttctc actagctctt ctcctcagtc ttcttctcct ctgtgtctct    60
gattctaggg cagaaacaac tgtgacccag tctccagcat ccctgtccat ggctatagga   120
gaaaaagtca ccatcagatg cataaccagc actgatattg atgatgatat gaactggtac   180
cagcagaagc caggggaacc tcctaagctc cttatttcag aaggcaatac tcttcgtcct   240
ggagtcccat cccgattctc cagcagtggc tatggtacag attttgtttt tacaattgaa   300
aacatgctct cagaagatgt tgcagattac tactgtttgc aaagtgataa cttgccgtac   360
acgttcggag gggggaccaa gctggaaatc aaacgtaagt agaatccaaa gaattc      416

<210> SEQ ID NO 76
<211> LENGTH: 37
<212> TYPE: DNA
<213> ORGANISM: Artificial Sequence
<220> FEATURE:
<223> OTHER INFORMATION: oligonucleotide

<400> SEQUENCE: 76
gctgctagca ccaccatgtt ctcactagct cttctcc                           37

<210> SEQ ID NO 77
<211> LENGTH: 45
<212> TYPE: DNA
<213> ORGANISM: Artificial Sequence
<220> FEATURE:
<223> OTHER INFORMATION: oligonucleotide

<400> SEQUENCE: 77
cgagaattct ttggattcta cttacgtttg atttccagct tggtc                  45

<210> SEQ ID NO 78
<211> LENGTH: 449
<212> TYPE: DNA
<213> ORGANISM: Artificial Sequence
<220> FEATURE:
<223> OTHER INFORMATION: Synthetic gene

<400> SEQUENCE: 78

```
actagtacca ccatggaatg gaactgggtc gttctcttcc tcctgtcact gactgcaggc    60
gtctattccc aagtgcagct cgtccagtct ggagctgaag tcaaaaagcc tggggcttca   120
gtgaaagtct cctgcaaggc ttctggcttc accttcagca gtagctatat cagttggttg   180
aggcaggccc ctggacagag acttgagtgg attgcatgga tttatgctgg aactggcgga   240
actagctata atcagaagtt cacaggcaag gccacactga ctgtagacac atccgccagc   300
acagcctaca tggaactcag cagcctgaga tctgaggaca ctgccgtcta ttactgtgca   360
agacataacc ctcgttacta tgctatggac tactggggcc aaggaaccac agtcaccgtc   420
tcctcaggta agaatggcct ctcaagctt                                     449
```

<210> SEQ ID NO 79
<211> LENGTH: 449
<212> TYPE: DNA
<213> ORGANISM: Artificial Sequence
<220> FEATURE:
<223> OTHER INFORMATION: Synthetic gene

<400> SEQUENCE: 79

```
actagtacca ccatggaatg gaactgggtc gttctcttcc tcctgtcact gactgcaggc    60
gtctattccc aagtgcagct cgtccagtct ggagctgaag tcaaaaagcc tggggcttca   120
gtgaaagtct cctgcaaggc ttctggcttc accttcagca gtagctatat cagttggttg   180
aggcaggccc ctggacagag acttgagtgg attgcatgga tttatgctgg aactggcgga   240
actagctata atcagaagtt cacaggcaga gtcacactga ctgtagacac atccgccagc   300
acagcctaca tggaactcag cagcctgaga tctgaggaca ctgccgtcta ttactgtgca   360
agacataacc ctcgttacta tgctatggac tactggggcc aaggaaccac agtcaccgtc   420
tcctcaggta agaatggcct ctcaagctt                                     449
```

<210> SEQ ID NO 80
<211> LENGTH: 416
<212> TYPE: DNA
<213> ORGANISM: Artificial Sequence
<220> FEATURE:
<223> OTHER INFORMATION: Synthetic gene

<400> SEQUENCE: 80

```
gctagcacca ccatgttctc actggctctg ctcctcagtc tgctgctcct ctgtgtctct    60
gattctagag cagacatcca gatgacccag tctccaagct ccctgtccgc cagcgtggga   120
gatagagtca ccatcacatg catcaccagc actgatattg atgatgatat gaactggtac   180
cagcagaagc cagggaaagc tcctaagctc ctgatttcag aaggcaatac tctgcgccct   240
ggagtcccat cccgattctc cggcagtggc tatggaacag attttacctt tacaattagc   300
tccctgcagc cagaagatat tgcaacctac tactgtttgc aaagtgataa cctgccctac   360
accttcggag gggggaccaa agtcgaaatc aaacgtaagt agaatccaaa gaattc       416
```

<210> SEQ ID NO 81
<211> LENGTH: 416
<212> TYPE: DNA
<213> ORGANISM: Artificial Sequence
<220> FEATURE:
<223> OTHER INFORMATION: Synthetic gene

```
<400> SEQUENCE: 81
gctagcacca ccatgttctc actggctctg ctcctcagtc tgctgctcct ctgtgtctct    60
gattctagag cagacatcca gatgacccag tctccaagct ccctgtccgc cagcgtggga   120
gatagagtca ccatcacatg catcaccagc actgatattg atgatgatat gaactggtac   180
cagcagaagc cagggaaagc tcctaagctc ctgatttcag aaggcaatac tctgcgccct   240
ggagtcccat cccgattctc cggcagtggc tctggaacag attttacctt tacaattagc   300
tccctgcagc cagaagatat tgcaacctac tactgtttgc aaagtgataa cctgccctac   360
accttcggag gggggaccaa agtcgaaatc aaacgtaagt agaatccaaa gaattc       416

<210> SEQ ID NO 82
<211> LENGTH: 416
<212> TYPE: DNA
<213> ORGANISM: Artificial Sequence
<220> FEATURE:
<223> OTHER INFORMATION: Synthetic gene

<400> SEQUENCE: 82
gctagcacca ccatgttctc actggctctg ctcctcagtc tgctgctcct ctgtgtctct    60
gattctagag cagacaccca gatgacccag tctccaagct ccctgtccgc cagcgtggga   120
gatagagtca ccatcacatg catcaccagc actgatattg atgatgatat gaactggtac   180
cagcagaagc cagggaaagc tcctaagctc ctgatttcag aaggcaatac tctgcgccct   240
ggagtcccat cccgattctc cggcagtggc tatggaacag attttacctt tacaattagc   300
tccctgcagc cagaagatat tgcaacctac tactgtttgc aaagtgataa cctgccctac   360
accttcggag gggggaccaa agtcgaaatc aaacgtaagt agaatccaaa gaattc       416

<210> SEQ ID NO 83
<211> LENGTH: 1407
<212> TYPE: DNA
<213> ORGANISM: Artificial Sequence
<220> FEATURE:
<223> OTHER INFORMATION: Synthetic IGg

<400> SEQUENCE: 83
atggaatgga actgggtcgt tctcttcctc ctgtcattaa ctgcaggtgt ctattcccag    60
ggtcagatgc agcagtctgg agctgagctg gtgaagcctg ggcttcagt gaagctgtcc   120 tgcaagactt ctggcttcac cttcagcagt agctatataa gttggttgaa gcagaagcct   180
cgacagagtc ttgagtggat tgcatggatt tatgctggaa ctggtggtac tagctataat   240
cagaagttca caggcaaggc caactgact gtagacacat cctccagcac agcctacatg   300
caactcagca gcctgacatc tgaggactct gccatctatt actgtgcaag acataaccct   360
cgttactatg ctatggacta ctggggtcaa ggaacctcag tcaccgtctc ctcagcctcc   420
accaagggcc catcggtctt ccccctggca ccctcctcca agagcacctc tgggggcaca   480
gcggccctgg gctgcctggt caaggactac ttccccgaac cggtgacggt gtcgtggaac   540
tcaggcgccc tgaccagcgg cgtgcacacc ttcccggctg tcctacagtc ctcaggactc   600
tactccctca gcagcgtggt gaccgtgccc tccagcagct gggcaccca gacctacatc   660 tgcaacgtga atcacaagcc cagcaacacc aaggtggaca agaaagttga gcccaaatct   720
tgtgacaaaa ctcacacatg cccaccgtgc ccagcacctg aactcctggg gggaccgtca   780
gtcttcctct tccccccaaa acccaaggac accctcatga tctcccggac ccctgaggtc   840
acatgcgtgg tggtggacgt gagccacgaa gaccctgagg tcaagttcaa ctggtacgtg   900
```

```
gacggcgtgg aggtgcataa tgccaagaca aagccgcggg aggagcagta caacagcacg    960
taccgtgtgg tcagcgtcct caccgtcctg caccaggact ggctgaatgg caaggagtac   1020
aagtgcaagg tctccaacaa agccctccca gcccccatcg agaaaaccat ctccaaagcc   1080
aaagggcagc cccgagaacc acaggtgtac accctgcccc catcccggga tgagctgacc   1140
aagaaccagg tcagcctgac ctgcctggtc aaaggcttct atcccagcga catcgccgtg   1200
gagtgggaga gcaatgggca gccggagaac aactacaaga ccacgcctcc cgtgctggac   1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaatga                                       1407
```

<210> SEQ ID NO 84
<211> LENGTH: 468
<212> TYPE: PRT
<213> ORGANISM: Artificial Sequence
<220> FEATURE:
<223> OTHER INFORMATION: Synthetic IGg

<400> SEQUENCE: 84

```
Met Glu Trp Asn Trp Val Val Leu Phe Leu Leu Ser Leu Thr Ala Gly
1               5                   10                  15

Val Tyr Ser Gln Gly Gln Met Gln Gln Ser Gly Ala Glu Leu Val Lys
            20                  25                  30

Pro Gly Ala Ser Val Lys Leu Ser Cys Lys Thr Ser Gly Phe Thr Phe
        35                  40                  45

Ser Ser Ser Tyr Ile Ser Trp Leu Lys Gln Lys Pro Arg Gln Ser Leu
    50                  55                  60

Glu Trp Ile Ala Trp Ile Tyr Ala Gly Thr Gly Gly Thr Ser Tyr Asn
65                  70                  75                  80

Gln Lys Phe Thr Gly Lys Ala Gln Leu Thr Val Asp Thr Ser Ser Ser
                85                  90                  95

Thr Ala Tyr Met Gln Leu Ser Ser Leu Thr Ser Glu Asp Ser Ala Ile
            100                 105                 110

Tyr Tyr Cys Ala Arg His Asn Pro Arg Tyr Tyr Ala Met Asp Tyr Trp
        115                 120                 125

Gly Gln Gly Thr Ser Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270
```

```
Met Ile Ser Arg Thr Pro Glu Val Thr Cys Val Val Asp Val Ser
        275                 280                 285
His Glu Asp Pro Glu Val Lys Phe Asn Trp Tyr Val Asp Gly Val Glu
    290                 295                 300
Val His Asn Ala Lys Thr Lys Pro Arg Glu Glu Gln Tyr Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Ala Leu Pro Ala Pro
            340                 345                 350
Ile Glu Lys Thr Ile Ser Lys Ala Lys Gly Gln Pro Arg Glu Pro Gln
        355                 360                 365
Val Tyr Thr Leu Pro Pro Ser Arg Asp Glu Leu Thr Lys Asn Gln Val
    370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Lys Leu Thr
            420                 425                 430
Val Asp Lys Ser Arg Trp Gln Gln Gly Asn Val Phe Ser Cys Ser Val
        435                 440                 445
Met His Glu Ala Leu His Asn His Tyr Thr Gln Lys Ser Leu Ser Leu
    450                 455                 460
Ser Pro Gly Lys
465
```

<210> SEQ ID NO 85
<211> LENGTH: 705
<212> TYPE: DNA
<213> ORGANISM: Artificial Sequence
<220> FEATURE:
<223> OTHER INFORMATION: Synthetic IGg

<400> SEQUENCE: 85

```
atgttctcac tagctcttct cctcagtctt cttctcctct gtgtctctga ttctagggca    60
gaaacaactg tgacccagtc tccagcatcc ctgtccatgg ctataggaga aaaagtcacc   120
atcagatgca taaccagcac tgatattgat gatgatatga actggtacca gcagaagcca   180
ggggaacctc ctaagctcct tatttcagaa ggcaatactc ttcgtcctgg agtcccatcc   240
cgattctcca gcagtggcta tggtacagat tttgttttta caattgaaaa catgctctca   300
gaagatgttg cagattacta ctgtttgcaa agtgataact tgccgtacac gttcggaggg   360
gggaccaagc tggaaatcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga gaaacacaaa gtctacgcct gcgaagtcac ccatcagggc   660
ctgagctcgc ccgtcacaaa gagcttcaac aggggagagt gttag              705
```

<210> SEQ ID NO 86
<211> LENGTH: 234
<212> TYPE: PRT
<213> ORGANISM: Artificial Sequence
<220> FEATURE:
<223> OTHER INFORMATION: Synthetic IGg

<400> SEQUENCE: 86

Met Phe Ser Leu Ala Leu Leu Ser Leu Leu Leu Cys Val Ser
1               5                   10                  15

Asp Ser Arg Ala Glu Thr Thr Val Thr Gln Ser Pro Ala Ser Leu Ser
            20                  25                  30

Met Ala Ile Gly Glu Lys Val Thr Ile Arg Cys Ile Thr Ser Thr Asp
        35                  40                  45

Ile Asp Asp Asp Met Asn Trp Tyr Gln Gln Lys Pro Gly Glu Pro Pro
    50                  55                  60

Lys Leu Leu Ile Ser Glu Gly Asn Thr Leu Arg Pro Gly Val Pro Ser
65              70                  75                  80

Arg Phe Ser Ser Ser Gly Tyr Gly Thr Asp Phe Val Phe Thr Ile Glu
                85                  90                  95

Asn Met Leu Ser Glu Asp Val Ala Asp Tyr Tyr Cys Leu Gln Ser Asp
            100                 105                 110

Asn Leu Pro Tyr Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145             150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 87
<211> LENGTH: 323
<212> TYPE: PRT
<213> ORGANISM: Homo sapiens
<220> FEATURE:
<223> OTHER INFORMATION: Human Trop-2

<400> SEQUENCE: 87

Met Ala Arg Gly Pro Gly Leu Ala Pro Pro Pro Leu Arg Leu Pro Leu
1               5                   10                  15

Leu Leu Leu Val Leu Ala Ala Val Thr Gly His Thr Ala Ala Gln Asp
            20                  25                  30

Asn Cys Thr Cys Pro Thr Asn Lys Met Thr Val Cys Ser Pro Asp Gly
        35                  40                  45

Pro Gly Gly Arg Cys Gln Cys Arg Ala Leu Gly Ser Gly Met Ala Val
    50                  55                  60

Asp Cys Ser Thr Leu Thr Ser Lys Cys Leu Leu Leu Lys Ala Arg Met
65              70                  75                  80

Ser Ala Pro Lys Asn Ala Arg Thr Leu Val Arg Pro Ser Glu His Ala
                85                  90                  95

Leu Val Asp Asn Asp Gly Leu Tyr Asp Pro Asp Cys Asp Pro Glu Gly

```
                  100                 105                 110
Arg Phe Lys Ala Arg Gln Cys Asn Gln Thr Ser Val Cys Trp Cys Val
            115                 120                 125

Asn Ser Val Gly Val Arg Arg Thr Asp Lys Gly Asp Leu Ser Leu Arg
        130                 135                 140

Cys Asp Glu Leu Val Arg Thr His His Ile Leu Ile Asp Leu Arg His
145                 150                 155                 160

Arg Pro Thr Ala Gly Ala Phe Asn His Ser Asp Leu Asp Ala Glu Leu
                165                 170                 175

Arg Arg Leu Phe Arg Glu Arg Tyr Arg Leu His Pro Lys Phe Val Ala
            180                 185                 190

Ala Val His Tyr Glu Gln Pro Thr Ile Gln Ile Glu Leu Arg Gln Asn
        195                 200                 205

Thr Ser Gln Lys Ala Ala Gly Asp Val Asp Ile Gly Asp Ala Ala Tyr
    210                 215                 220

Tyr Phe Glu Arg Asp Ile Lys Gly Glu Ser Leu Phe Gln Gly Arg Gly
225                 230                 235                 240

Gly Leu Asp Leu Arg Val Arg Gly Glu Pro Leu Gln Val Glu Arg Thr
                245                 250                 255

Leu Ile Tyr Tyr Leu Asp Glu Ile Pro Pro Lys Phe Ser Met Lys Arg
            260                 265                 270

Leu Thr Ala Gly Leu Ile Ala Val Ile Val Val Val Val Ala Leu
        275                 280                 285

Val Ala Gly Met Ala Val Leu Val Ile Thr Asn Arg Arg Lys Ser Gly
    290                 295                 300

Lys Tyr Lys Lys Val Glu Ile Lys Glu Leu Gly Glu Leu Arg Lys Glu
305                 310                 315                 320

Pro Ser Leu

<210> SEQ ID NO 88
<211> LENGTH: 116
<212> TYPE: PRT
<213> ORGANISM: Homo sapiens
<220> FEATURE:
<221> NAME/KEY: VARIANT
<222> LOCATION: (31)..(35)
<223> OTHER INFORMATION: Xaa is any of the 20 natural amino acids
<220> FEATURE:
<221> NAME/KEY: VARIANT
<222> LOCATION: (50)..(66)
<223> OTHER INFORMATION: Xaa is any of the 20 natural amino acids
<220> FEATURE:
<221> NAME/KEY: VARIANT
<222> LOCATION: (99)..(105)
<223> OTHER INFORMATION: Xaa is any of the 20 natural amino acids
<220> FEATURE:
<223> OTHER INFORMATION: Framework of human VH M17751.1

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Xaa Xaa
            20                  25                  30

Xaa Xaa Xaa Trp Val Arg Gln Ala Pro Gly Gln Arg Leu Glu Trp Met
        35                  40                  45

Gly Xaa Xaa Xaa Xaa Xaa Xaa Xaa Xaa Xaa Xaa Xaa Xaa Xaa Xaa Xaa
    50                  55                  60

Xaa Xaa Arg Val Thr Ile Thr Arg Asp Thr Ser Ala Ser Thr Ala Tyr
65                  70                  75                  80
```

```
Met Glu Leu Ser Ser Leu Arg Ser Glu Asp Thr Ala Val Tyr Tyr Cys
            85                  90                  95

Ala Arg Xaa Xaa Xaa Xaa Xaa Xaa Trp Gly Gln Gly Thr Leu Val
            100                 105                 110

Thr Val Ser Ser
        115

<210> SEQ ID NO 89
<211> LENGTH: 116
<212> TYPE: PRT
<213> ORGANISM: Homo sapiens
<220> FEATURE:
<221> NAME/KEY: VARIANT
<222> LOCATION: (31)..(35)
<223> OTHER INFORMATION: Xaa is any 20 amino acids
<220> FEATURE:
<221> NAME/KEY: VARIANT
<222> LOCATION: (31)..(35)
<223> OTHER INFORMATION: Xaa is any of the 20 natural amino acids
<220> FEATURE:
<221> NAME/KEY: VARIANT
<222> LOCATION: (50)..(66)
<223> OTHER INFORMATION: Xaa is any 20 amino acids
<220> FEATURE:
<221> NAME/KEY: VARIANT
<222> LOCATION: (99)..(105)
<223> OTHER INFORMATION: Xaa is any 20 amino acids
<220> FEATURE:
<223> OTHER INFORMATION: Framework of human VH L02325.1

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Xaa Xaa
            20                  25                  30

Xaa Xaa Xaa Trp Val Arg Gln Ala Pro Gly Gln Gly Leu Glu Trp Met
            35                  40                  45

Gly Xaa Xaa Xaa Xaa Xaa Xaa Xaa Xaa Xaa Xaa Xaa Xaa Xaa Xaa Xaa
        50                  55                  60

Xaa Xaa Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Xaa Xaa Xaa Xaa Xaa Xaa Trp Gly Gln Gly Thr Leu Val
            100                 105                 110

Thr Val Ser Ser
        115

<210> SEQ ID NO 90
<211> LENGTH: 119
<212> TYPE: PRT
<213> ORGANISM: Homo sapiens
<220> FEATURE:
<221> NAME/KEY: VARIANT
<222> LOCATION: (31)..(35)
<223> OTHER INFORMATION: Xaa is any of the 20 natural amino acids
<220> FEATURE:
<221> NAME/KEY: VARIANT
<222> LOCATION: (50)..(66)
<223> OTHER INFORMATION: Xaa is any of the 20 natural amino acids
<220> FEATURE:
<221> NAME/KEY: VARIANT
<222> LOCATION: (99)..(108)
<223> OTHER INFORMATION: Xaa is any of the 20 natural amino acids
<220> FEATURE:
<223> OTHER INFORMATION: Framework of human VH X65888.1
```

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Xaa Xaa
            20                  25                  30

Xaa Xaa Xaa Trp Val Arg Gln Ala Pro Gly Gln Arg Leu Glu Trp Met
        35                  40                  45

Gly Xaa Xaa Xaa Xaa Xaa Xaa Xaa Xaa Xaa Xaa Xaa Xaa
    50                  55                  60

Xaa Xaa Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Xaa Xaa Xaa Xaa Xaa Xaa Xaa Xaa Xaa Trp Gly Gln Gly
            100                 105                 110

Thr Thr Val Thr Val Ser Ser
        115

<210> SEQ ID NO 91
<211> LENGTH: 111
<212> TYPE: PRT
<213> ORGANISM: Homo sapiens
<220> FEATURE:
<221> NAME/KEY: VARIANT
<222> LOCATION: (24)..(38)
<223> OTHER INFORMATION: Xaa is any of the 20 natural amino acids
<220> FEATURE:
<221> NAME/KEY: VARIANT
<222> LOCATION: (54)..(60)
<223> OTHER INFORMATION: Xaa is any of the 20 natural amino acids
<220> FEATURE:
<221> NAME/KEY: VARIANT
<222> LOCATION: (93)..(101)
<223> OTHER INFORMATION: Xaa is any of the 20 natural amino acids
<220> FEATURE:
<223> OTHER INFORMATION: Framework of human VL Z46622.1

<400> SEQUENCE: 91

Asp Ile Val Met Thr Gln Ser Pro Asp Ser Leu Ala Val Ser Leu Gly
1               5                   10                  15

Glu Arg Ala Thr Ile Asn Cys Xaa Xaa Xaa Xaa Xaa Xaa Xaa Xaa
            20                  25                  30

Xaa Xaa Xaa Xaa Xaa Xaa Trp Tyr Gln Gln Lys Pro Gly Gln Pro Pro
        35                  40                  45

Lys Leu Leu Ile Tyr Xaa Xaa Xaa Xaa Xaa Xaa Xaa Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Xaa Xaa Xaa Xaa
                85                  90                  95

Xaa Xaa Xaa Xaa Xaa Phe Gly Gln Gly Thr Lys Leu Glu Ile Lys
            100                 105                 110

<210> SEQ ID NO 92
<211> LENGTH: 107
<212> TYPE: PRT
<213> ORGANISM: Homo sapiens
<220> FEATURE:
<221> NAME/KEY: VARIANT
<222> LOCATION: (24)..(34)
<223> OTHER INFORMATION: Xaa is any of the 20 natural amino acids

```
<220> FEATURE:
<221> NAME/KEY: VARIANT
<222> LOCATION: (50)..(56)
<223> OTHER INFORMATION: Xaa is any of the 20 natural amino acids
<220> FEATURE:
<221> NAME/KEY: VARIANT
<222> LOCATION: (89)..(97)
<223> OTHER INFORMATION: Xaa is any of the 20 natural amino acids
<220> FEATURE:
<223> OTHER INFORMATION: Framework of human VL AY043146.1

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Xaa Xaa Xaa Xaa Xaa Xaa Xaa Xaa
            20                  25                  30

Xaa Xaa Trp Tyr Gln Gln Lys Pro Gly Lys Ala Pro Lys Leu Leu Ile
        35                  40                  45

Tyr Xaa Xaa Xaa Xaa Xaa Xaa Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Xaa Xaa Xaa Xaa Xaa Xaa Xaa
                85                  90                  95

Xaa Phe Gly Gly Gly Thr Lys Val Glu Ile Lys
            100                 105

<210> SEQ ID NO 93
<211> LENGTH: 123
<212> TYPE: PRT
<213> ORGANISM: Homo sapiens
<220> FEATURE:
<223> OTHER INFORMATION: human VH M17751.1

<400> SEQUENCE: 93

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Met Ile Leu Arg Ile Gly His Gly Gln Pro Gln Gly Tyr
            100                 105                 110

Trp Gly Gln Gly Thr Leu Val Thr Val Ser Ser
        115                 120

<210> SEQ ID NO 94
<211> LENGTH: 126
<212> TYPE: PRT
<213> ORGANISM: Homo sapiens
<220> FEATURE:
<223> OTHER INFORMATION: human VH L02325.1

<400> SEQUENCE: 94

Gln Val Gln Leu Val Gln Ser Gly Ala Glu Val Lys Lys Pro Gly Ala
```

```
            1               5                  10                 15
            Ser Val Lys Val Ser Cys Lys Ala Ser Gly Tyr Thr Phe Thr Ser Tyr
                            20                 25                 30

Tyr Ile His Trp Val Arg Gln Ala Pro Gly Gln Gly Leu Glu Trp Met
                            35                 40              45

Gly Ile Ile Asn Pro Ser Gly Ser Thr Asn Tyr Ala Gln Lys Phe
                        50              55                 60

Gln Gly Arg Val Thr Met Thr Arg Asp Thr Ser Thr Ser Thr Val Tyr
            65              70                 75                 80

Met Glu Leu Ser Ser Leu Arg Ser Glu Asp Thr Ala Val Tyr Tyr Cys
                            85                 90                 95

Ala Arg Ala Pro His Gln Arg Thr Arg Ile Ala Ala Arg Pro Gly Glu
                            100                105                110

Gly Asp Ser Trp Gly Gln Gly Thr Leu Val Thr Val Ser Ser
                        115                120                125

<210> SEQ ID NO 95
<211> LENGTH: 124
<212> TYPE: PRT
<213> ORGANISM: Homo sapiens
<220> FEATURE:
<223> OTHER INFORMATION: human VH X65888.1

<400> SEQUENCE: 95

Gln Val Gln Leu Val Gln Ser Gly Ala Glu Val Lys Lys Pro Gly Ala
            1               5                  10                 15

Ser Val Lys Val Ser Cys Lys Ala Ser Gly Tyr Thr Phe Thr Ser Tyr
                            20                 25                 30

Ala Met His Trp Val Arg Gln Ala Pro Gly Gln Arg Leu Glu Trp Met
                            35                 40                 45

Gly Trp Ile Asn Ala Gly Asn Gly Asn Thr Lys Tyr Ser Gln Lys Phe
                        50              55                 60

Gln Gly Arg Val Thr Ile Thr Arg Asp Thr Ser Ala Ser Thr Ala Tyr
            65              70                 75                 80

Met Glu Leu Ser Ser Leu Arg Ser Glu Asp Thr Ala Val Tyr Tyr Cys
                            85                 90                 95

Ala Arg Asp Leu Leu Cys Ser Gly Cys Asp Tyr Tyr Tyr Gly Met Asp
                            100                105                110

Val Trp Gly Gln Gly Thr Thr Val Thr Val Ser Ser
                        115                120

<210> SEQ ID NO 96
<211> LENGTH: 114
<212> TYPE: PRT
<213> ORGANISM: Homo sapiens
<220> FEATURE:
<223> OTHER INFORMATION: human VL Z46622.1

<400> SEQUENCE: 96

Asp Ile Val Met Thr Gln Ser Pro Asp Ser Leu Ala Val Ser Leu Gly
            1               5                  10                 15

Glu Arg Ala Thr Ile Asn Cys Lys Ser Ser Gln Ser Val Leu Tyr Ser
                            20                 25                 30

Ser Asn Asn Lys Asn Tyr Leu Ala Trp Tyr Gln Gln Lys Pro Gly Gln
                            35                 40                 45

Pro Pro Lys Leu Leu Ile Tyr Trp Ala Ser Thr Arg Glu Ser Gly Val
                        50              55                 60
```

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Ser Tyr Thr Phe Gly Gln Gly Thr Lys Leu Glu
                100                 105                 110

Ile Lys

<210> SEQ ID NO 97
<211> LENGTH: 108
<212> TYPE: PRT
<213> ORGANISM: Homo sapiens
<220> FEATURE:
<223> OTHER INFORMATION: human VL AY043146.1

<400> SEQUENCE: 97

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Ser
                 85                  90                  95

Leu Thr Phe Gly Gly Gly Thr Lys Val Glu Ile Lys
                100                 105
```